United States Patent
Attucks

(10) Patent No.: US 10,463,652 B2
(45) Date of Patent: Nov. 5, 2019

(54) BACH1 INHIBITORS IN COMBINATION WITH NRF2 ACTIVATORS AND PHARMACEUTICAL COMPOSITIONS THEREOF

(71) Applicant: vTv Therapeutics LLC, High Point, NC (US)

(72) Inventor: Otis Clinton Attucks, Winston-Salem, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 16/188,652

(22) Filed: Nov. 13, 2018

(65) Prior Publication Data

US 2019/0076410 A1    Mar. 14, 2019

Related U.S. Application Data

(60) Division of application No. 15/584,459, filed on May 2, 2017, now Pat. No. 10,172,840, which is a continuation of application No. PCT/US2015/062096, filed on Nov. 23, 2015.

(60) Provisional application No. 62/085,875, filed on Dec. 1, 2014.

(51) Int. Cl.
C07D 235/04    (2006.01)
A61K 31/437   (2006.01)
A61K 31/56    (2006.01)
A61K 31/428   (2006.01)

(52) U.S. Cl.
CPC .......... *A61K 31/437* (2013.01); *A61K 31/428* (2013.01); *A61K 31/56* (2013.01); *Y02A 50/395* (2018.01)

(58) Field of Classification Search
CPC .... C07D 235/04; A61K 31/437; A61K 31/56; A61K 31/428
USPC ....................................... 548/304.4; 514/303
See application file for complete search history.

(56) References Cited

U.S. PATENT DOCUMENTS

| | | | |
|---|---|---|---|
| 5,561,134 A | 10/1996 | Spada et al. | |
| 6,358,978 B1 | 3/2002 | Ritzeler et al. | |
| 6,509,376 B1 | 1/2003 | Joshi et al. | |
| 6,562,854 B2 | 5/2003 | Church et al. | |
| 7,030,139 B2 | 4/2006 | Cheng et al. | |
| 7,030,150 B2 | 4/2006 | Lackey et al. | |
| 7,238,813 B2 | 7/2007 | Cheung et al. | |
| 7,320,999 B2 | 1/2008 | Joshi et al. | |
| 7,355,052 B2 | 4/2008 | Poitout et al. | |
| 7,407,968 B2 | 8/2008 | Page et al. | |
| 7,413,578 B2 | 8/2008 | Javet et al. | |
| 7,429,608 B2 | 9/2008 | Norman et al. | |
| 7,501,525 B2 | 3/2009 | Poitout et al. | |
| 7,517,893 B2 | 4/2009 | Tidwell et al. | |
| 7,531,553 B2 | 5/2009 | Di Pietro et al. | |
| 7,619,001 B2 | 11/2009 | Joshi et al. | |
| 7,803,840 B2 | 9/2010 | Joshi et al. | |
| 7,816,539 B2 | 10/2010 | Poitout et al. | |
| 7,820,821 B2 | 10/2010 | Mjalli et al. | |
| 7,915,402 B2 | 3/2011 | Anderson et al. | |
| 8,399,514 B2 | 3/2013 | Lukashev et al. | |
| 8,455,544 B2 | 6/2013 | Sporn et al. | |
| 8,524,773 B2 | 9/2013 | Joshi et al. | |
| 8,633,243 B2 | 1/2014 | Walling et al. | |
| 8,759,535 B2 | 6/2014 | Mjalli et al. | |
| 9,447,468 B2 | 9/2016 | Kassis et al. | |
| 2007/0219235 A1 | 9/2007 | Mjalli et al. | |
| 2010/0152170 A1 | 6/2010 | Mjalli et al. | |
| 2011/0201604 A1 | 8/2011 | Mjalli et al. | |
| 2013/0158077 A1 | 6/2013 | Kahrs | |
| 2014/0200212 A1 | 7/2014 | Mjalli et al. | |

FOREIGN PATENT DOCUMENTS

| | | |
|---|---|---|
| AU | 12245/95 | 8/1995 |
| DE | 102005003362 | 7/2006 |
| EP | 0639573 | 2/1995 |
| EP | 0668270 | 8/1995 |
| EP | 1792613 | 6/2007 |
| EP | 1726589 | 10/2008 |
| JP | 2000-038387 | 2/2000 |
| JP | 2003-344971 | 12/2003 |
| JP | 2009-149589 | 7/2009 |
| WO | WO 1995/028160 | 10/1995 |
| WO | WO 1998/045275 | 10/1998 |
| WO | WO 1999/026932 | 6/1999 |
| WO | WO 2000/005223 | 2/2000 |
| WO | WO 2002/044156 | 6/2002 |
| WO | WO 2002/085866 | 10/2002 |
| WO | WO 2002/092575 | 11/2002 |
| WO | WO 2004/035548 | 4/2004 |

(Continued)

OTHER PUBLICATIONS

Alam J and Cook JL. (2007) "How many transcription factors does it take to turn on the heme oxygenase-1 gene?" Am. J. Respir. Cell Mol. Biol. 36:166-174.
Attucks OC, et al. (2014) Induction of Heme Oxygenase I (HMOX1) by HPP-4382: A Novel Modulator of Bach1 Activity. PLoS ONE 9(7): e101044. doi:10.1371/journal.pone.0101044.
Barone, et al., "The Janus face of the heme oxygenase/biliverdin reductase . . . ," Neurobiology of Disease 62:144-159 (2014).
FDA Approved Labeling Text dated Mar. 27, 2013 for TECFIDERA.
Gupta et al., "Neurotherapeutic effects of novel HO-1 inhibitors in vitro and in a transgenic mouse model of Alzheimer's disease" Journal of Neurochemistry, 2014, vol. 131, pp. 778-790.
Hamamura et al., "Induction of heme oxygenase-I by cobalt protoporphyrin enhances the antitumour effect of bortezomib in adult T-cell leukaemia cells," British Journal of Cancer, 97:1099-1105 (2007).

(Continued)

*Primary Examiner* — Niloofar Rahmani
(74) *Attorney, Agent, or Firm* — Samuel B. Rollins

(57) ABSTRACT

The disclosure provides pharmaceutical compositions comprising Bach1 Inhibitors and Nrf2 Activators. The disclosure also provides methods of treating diseases such as psoriasis, multiple sclerosis, and COPD comprising administering a Bach1 Inhibitor and a Nrf2 Activator to a subject in need thereof.

7 Claims, 5 Drawing Sheets

(56) References Cited

FOREIGN PATENT DOCUMENTS

| | | |
|---|---|---|
| WO | WO 2004/085425 | 10/2004 |
| WO | WO 2005/117890 | 12/2005 |
| WO | WO 2006/066879 | 6/2006 |
| WO | WO 2006/081244 | 8/2006 |
| WO | WO 2007/093600 | 8/2007 |
| WO | WO 2007/095124 | 8/2007 |
| WO | WO 2007/095601 | 8/2007 |
| WO | WO 2008/113255 | 9/2008 |
| WO | WO 2008/151437 | 12/2008 |
| WO | WO 2008/153701 | 12/2008 |
| WO | WO 2009/017701 | 2/2009 |
| WO | WO 2009/051796 | 4/2009 |
| WO | WO 2009/071650 | 6/2009 |
| WO | WO 2009/116074 | 9/2009 |
| WO | WO 2009/126635 | 10/2009 |
| WO | WO 2009/126691 | 10/2009 |
| WO | WO 2009/133127 | 11/2009 |
| WO | WO 2009/134850 | 11/2009 |
| WO | WO 2010/003197 | 1/2010 |
| WO | WO 2010/007316 | 1/2010 |
| WO | WO 2010/007317 | 1/2010 |
| WO | WO 2010/007318 | 1/2010 |
| WO | WO 2010/036613 | 4/2010 |
| WO | WO 2010/047982 | 4/2010 |
| WO | WO 2010/065674 | 6/2010 |
| WO | WO 2010/135014 | 11/2010 |
| WO | WO 2013/092269 | 11/2010 |
| WO | 2011103018 * | 8/2011 |
| WO | WO 2011/103018 | 8/2011 |
| WO | WO 2012/094580 | 7/2012 |

OTHER PUBLICATIONS

Kim et al., "The novel Bach1 Inhibitor HPP971 uniquely activates Nrf2 and reduces disease severity in a mouse model of experimental autoimmune encephalomyelitis." Abstract submitted for presentation Sep. 11, 2014 at the Joint ACTRIMS-ECTRIMS Meeting in Boston, MA, Sep. 10-13, 2014.

Kim et al., "The novel Bach1 Inhibitor HPP971 uniquely activates Nrf2 and reduces disease severity in a mouse model of experimental autoimmune encephalomyelitis." Poster presented Sep. 11, 2014 at the Joint ACTRIMS-ECTRIMS Meeting in Boston, MA, Sep. 10-13, 2014.

Kostura et al., "Novel Bach1 Modulators Increase HMOX1 and Suppress Hypertension in the Goldblatt Model of Renovascular Hypertension," American Heart Association Scientific Sessions, Nov. 2013, Poster.

Li B et al. (2013) "Sulforaphane ameliorates the development of experimental autoimmune encephalomyelitis by antagonizing oxidative stress and Th17-related inflammation in mice," Exp. Neurol. 250:239-249. doi: 10.1016/j.expneurol.2013.10.002.

Linker RA et al. (2011) "Fumaric acid esters exert neuroprotective effects in neuroinflammation via activation of the Nrf2 antioxidant pathway," Brain 134:678-692.

Macleod AK et al. (2009) "Characterization of cancer chemopreventive Nrf2-dependent gene battery in human keratinocytes . . . compounds," Carcinogenesis 30 (9); 1571-1580.

Malhotra D et al. (2010) "Global mapping of binding sites for Nrf2 identifies novel targets in cell survival response through ChIP-Seq profiling and network analysis," Nucleic Acids Res 38: 5718-5734.

Medicines in Development for Cancer. Pharmaceutical Research and Manufacturers of America, Washington, DC, pp. 1-103 (2009).

Medicines in Development for Neurological Disorders. Pharmaceutical Research and Manufacturers of America, pp. 1-43 (2008).

Pareek et al. (2011) "Triterpenoid modulation of IL-17 and Nrf-2 expression ameliorates neuroinflammation and promotes remyelination in autoimmune encephalomyelitis," Sci Rep. 1:201.

Satoh T, Mckercher S and Lipton S (2014) "Nrf2/ARE-mediated antioxidant actions of pro-electrophilic drugs," Free Rad Bio Med. 66; 45-57.

Saw et al., "Synergistic anti-inflammatory effects of low doses of curcumin in combination with polyunsaturated fatty acids: Docosahexaenoic acid or eicosapentaenoic acid," Biochemical Pharmacology 79:421-430 (2010).

Suzuki T et al. (2013) "Toward clinical application of the Keap1-Nrf2 pathway," Trends Pharmacol Sci 34; 340-346.

Gopal et al. "Evidence of activation of the Nrf2 pathway in multiple sclerosis patients treated with delayed-release dimethyl fumarate in the Phase 3 DEFINE and CONFIRM studies." Multiple Sclerosis Journal (2017).

* cited by examiner

BACH1 INHIBITORS IN COMBINATION WITH NRF2 ACTIVATORS AND PHARMACEUTICAL COMPOSITIONS THEREOF

BACKGROUND OF THE INVENTION

Cellular damage due to oxidative stress caused by reactive oxygen species (ROS) has been demonstrated to be involved in the onset or progression of various chronic diseases, e.g., cardiovascular disease, including arteriosclerosis and hypertension; diabetes and diabetic related complications, such as glomerular nephropathy; cerebral nerve degenerative diseases, such as Alzheimer's disease, Parkinson's disease, ALS (amyotrophic lateral sclerosis) and multiple sclerosis; asthma, chronic obstructive pulmonary disease, skin diseases, eye diseases, and cancer. Enhancing the capability of protecting from oxidative stress may be useful in treating these diseases. Further, with the varied etiology associated with this diverse set of diseases, a general strategy to mitigate oxidative stress would be beneficial.

The basic biochemistry of a cell generates ROS, including superoxide anions, hydroxyl anions, nitric oxide, peroxynitrite, and hydrogen peroxide. All of these products serve critical cellular signaling needs, but also have deleterious effects if overproduced or left unchecked. Many disease conditions induce persistent levels of ROS that are associated with the establishment of chronic pathophysiologic changes seen within a variety of tissues. These complications, in and of themselves, may be the primary drivers of disease morbidity and mortality.

Under normal physiological conditions, production of ROS are counterbalanced by a well defined and conserved set of cellular pathways that respond to, limit, and repair the damage due to ROS. This adaptive program is largely controlled by two proteins: Kelch like-ECH-associated protein 1 (Keap1) and the transcription factor NFEL2L2 (Nrf2). The Keap1-Nrf2 system has evolved to respond to intracellular oxidative stress; in particular the generation of reactive electrophiles produced from oxidation of endogenous cellular constituents as well as xenobiotics. In the absence of cellular oxidative stress, Nrf2 levels in the cytoplasm are maintained at low basal levels by binding to Keap1 and Cullin 3, which leads to the degradation of Nrf2 by ubiquitination. During periods of oxidative stress, as levels of reactive electrophilic metabolites increase, the ability of Keap1 to target Nrf2 for ubiquitin-dependent degradation is disrupted, thereby increasing Nrf2 protein levels and its transport into the nucleus, resulting in transcription of antioxidant response genes. Nrf2 binds to antioxidant response elements (AREs) found in the promoters of over 200 antioxidant and cytoprotective genes including NAD(P)H dehydrogenase, quinone 1 (NQO1), catalase (CAT), glutamate-cysteine ligase (GCLC), aldoketoreductase family members, thioredoxin reductase (TXNRD1), and heme oxygenase-1 (HMOX1). Activation of the anti-oxidant response via the Keap1-Nrf2 pathway is considered to be protective in nearly every organ system. As described below, various Nrf2 Activators have been and are being developed for treatment of diseases or conditions associated with oxidative stress.

There is, however, another mechanism by which ARE-regulated genes are controlled and that is through Bach1, a transcriptional repressor that binds to ARE promoter elements. Binding of Bach1 to ARE promoter elements results in suppression of Nrf2 activity. Bach1 regulates ARE gene expression by binding to the small Maf proteins and ARE sequences that are also separately bound by Nrf2. Natively, Bach1 may be bound by its ligand, heme, which causes Bach1 to be displaced from the ARE, exported from the nucleus, and degraded. Bach1 and its ligand coordinate the overall intracellular levels of heme and iron with anti-oxidant gene expression. Genetic evidence indicates that Bach1 deletion leads to a significant level of protection in a wide variety of murine disease models. These observations suggest that ARE-regulated genes may be controlled by an intracellular ligand independent of ROS generation, electrophilic reactivity, or elevation of Nrf2 levels in the cell. Thus, agents that target Bach1 and inhibit Bach1 repression may be useful to elevate expression of ARE-regulated genes.

PCT Publication No. WO 2011/103018 ("WO '018") describes substituted fused imidazole derivatives that upregulate expression of HMOX1 in vitro. PCT Publication No. WO 2012/094580 ("WO '580") describes various compounds that modulate cellular oxidative stress including fused imidazole derivatives having a structure similar to or the same as compounds disclosed in WO '018. Paragraphs [0196] to [0198] of WO '580 describe tests that suggest that fused imidazole derivatives similar to those disclosed in WO '018 may directly modulate Bach1 activity so as to inhibit Bach 1's repression of Nrf2 dependent gene transcription.

BRIEF SUMMARY OF THE INVENTION

Disclosed herein are combinations and pharmaceutical compositions comprising Bach1 Inhibitors and Nrf2 Activators (each an "agent" and together "agents"), and methods of using combinations of Bach 1 Inhibitors and Nrf2 Activators for treating oxidative stress and diseases associated with oxidative stress such as psoriasis, asthma, multiple sclerosis, inflammatory bowel disease, and COPD.

According to the present invention, improved treatment results may be obtained in the treatment of autoimmune and/or inflammatory diseases, when a Bach1 Inhibitor and an Nrf2 Activator are used in the treatment of the disease in combination as compared to the treatment with Bach1 Inhibitor or an Nrf2 activator, alone. Co-administration of a Bach1 Inhibitor and an Nrf2 Activator or an administration of a fixed dose combination of a Bach1 Inhibitor and an Nrf2 Activator may result in an improved therapeutic effect (or therapeutic window), which may be more than additive effect, compared to the administration of a Bach1 Inhibitor or Nrf2 Activator, respectively, administered as monotherapy.

DETAILED DESCRIPTION OF THE INVENTION

I. Definitions

Figure 1:
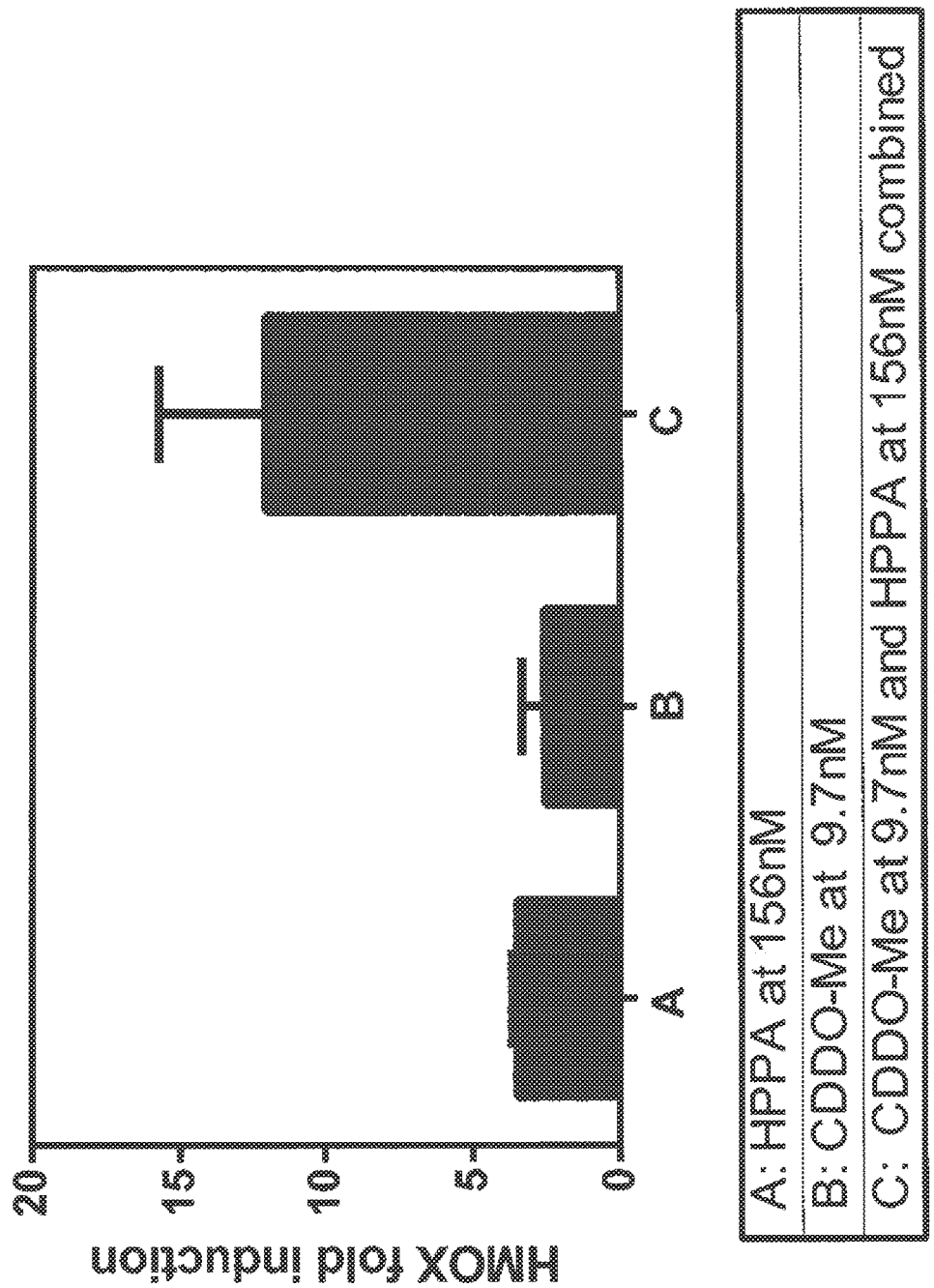
FIG. 1 shows the effect on HMOX induction of HPP-A at 156 nM (bar A); CDDO-Me at 9.7 nm (bar B); and HPP-A at 156 nM and CDDO-Me at 9.7 nm (bar C).

The following definitions are intended to clarify the terms defined. If a particular term used herein is not specifically defined, the term should not be considered to be indefinite. Rather, such undefined terms are to be construed in accordance with their plain and ordinary meaning to a person of ordinary skill in the field(s) of art to which the invention is directed.

As used herein the term "alkyl" refers to a straight or branched chain saturated hydrocarbon having one to ten carbon atoms, which may be optionally substituted, as herein further described, with multiple degrees of substitution being allowed. Examples of "alkyl" as used herein include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl.

The number carbon atoms in an alkyl group is represented by the phrase "$C_{x-y}$ alkyl," which refers to an alkyl group, as herein defined, containing from x to y, inclusive, carbon atoms. Thus, $C_{1-6}$ alkyl represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl.

As used herein, the term "alkylene" refers to a straight or branched chain divalent saturated hydrocarbon radical having from one to ten carbon atoms, which may be optionally substituted as herein further described, with multiple degrees of substitution being allowed. Examples of "alkylene" as used herein include, but are not limited to, methylene, ethylene, n-propylene, 1-methylethylene, 2-methylethylene, dimethylmethylene, n-butylene, 1-methyl-n-propylene, and 2-methyl-n-propylene.

The number of carbon atoms in an alkylene group is represented by the phrase "$C_{x-y}$ alkylene," which refers to an alkylene group, as herein defined, containing from x to y, inclusive, carbon atoms. Similar terminology will apply for other terms and ranges as well. Thus, $C_{1-4}$ alkylene represents an alkylene chain having from 1 to 4 carbons atoms, and, for example, includes, but is not limited to, methylene, ethylene, n-propylene, 1-methylethylene, 2-methylethylene, dimethylmethylene, n-butylene, 1-methyl-n-propylene, and 2-methyl-n-propylene.

As used herein, the term "cycloalkyl" refers to a saturated, three- to ten-membered, cyclic hydrocarbon ring, which may be optionally substituted as herein further described, with multiple degrees of substitution being allowed. Such "cycloalkyl" groups are monocyclic, bicyclic, or tricyclic. Examples of "cycloalkyl" groups as used herein include, but are not limited to, cyclopropyl, cyclobutyl, cyclopentyl, cyclohexyl, cycloheptyl, norbornyl, and adamantyl.

The number of carbon atoms in a cycloalkyl group will be represented by the phrase "$C_{x-y}$ cycloalkyl," which refers to a cycloalkyl group, as herein defined, containing from x to y, inclusive, carbon atoms. Similar terminology will apply for other terms and ranges as well. Thus, $C_{3-10}$ cycloalkyl represents a cycloalkyl group having from 3 to 10 carbons as described above, and for example, includes, but is not limited to, cyclopropyl, cyclobutyl, cyclopentyl, cyclohexyl, cycloheptyl, norbornyl, and adamantyl.

As used herein, the term "heterocycle" or "heterocyclyl" refers to an optionally substituted mono- or polycyclic saturated ring system containing one or more heteroatoms. Such "heterocycle" or "heterocyclyl" groups may be optionally substituted as herein further described, with multiple degrees of substitution being allowed. The term "heterocycle" or "heterocyclyl," as used herein, does not include ring systems that contain one or more aromatic rings. Examples of heteroatoms include nitrogen, oxygen, or sulfur atoms, including N-oxides, sulfur oxides, and sulfur dioxides. Typically, the ring is three- to twelve-membered. Such rings may be optionally fused to one or more of another heterocyclic ring(s) or cycloalkyl ring(s). Examples of "heterocyclic" groups, as used herein include, but are not limited to, tetrahydrofuran, tetrahydropyran, 1,4-dioxane, 1,3-dioxane, piperidine, pyrrolidine, morpholine, tetrahydrothiopyran, and tetrahydrothiophene, where attachment can occur at any point on said rings, as long as attachment is chemically feasible. Thus, for example, "morpholine" refers to morpholin-2-yl, morpholin-3-yl, and morpholin-4-yl.

As used herein, when "heterocycle" or "heterocyclyl" is recited as a possible substituent, the "heterocycle" or "heterocyclyl" group can attach through either a carbon atom or any heteroatom, to the extent that attachment at that point is chemically feasible. For example, "heterocyclyl" would include pyrrolidin-1-yl, pyrrolidin-2-yl, and pyrrolidin-3-yl. When "heterocycle" or "heterocyclyl" groups contain a nitrogen atom in the ring, attachment through the nitrogen atom can alternatively be indicated by using an "-ino" suffix with the ring name. For example, pyrrolidino refers to pyrrolidin-1-yl.

As used herein the term "halogen" refers to fluorine, chlorine, bromine, or iodine.

As used herein, the term "oxo" refers to a >C=O substituent. When an oxo substituent occurs on an otherwise saturated group, such as with an oxo-substituted cycloalkyl group (e.g., 3-oxo-cyclobutyl), the substituted group is still intended to be a saturated group.

As used herein, the term "heteroaryl" refers to a five- to fourteen-membered optionally substituted mono- or polycyclic ring system, which contains at least one aromatic ring and also contains one or more heteroatoms. Such "heteroaryl" groups may be optionally substituted as herein further described, with multiple degrees of substitution being allowed. In a polycyclic "heteroaryl" group that contains at least one aromatic ring and at least one non-aromatic ring, the aromatic ring(s) need not contain a heteroatom. Thus, for example, "heteroaryl," as used herein, would include indolinyl. Further, the point of attachment may be to any ring within the ring system without regard to whether the ring containing the attachment point is aromatic or contains a heteroatom. Thus, for example, "heteroaryl," as used herein, would include indolin-1-yl, indolin-3-yl, and indolin-5-yl. Examples of heteroatoms include nitrogen, oxygen, or sulfur atoms, including N-oxides, sulfur oxides, and sulfur dioxides, where feasible. Examples of "heteraryl" groups, as used herein include, but are not limited to, furyl, thiophenyl, pyrrolyl, oxazolyl, thiazolyl, imidazolyl, isoxazolyl, isothiazolyl, 1,2,4-triazolyl, pyrazolyl, pyridinyl, pyridazinyl, pyrimidinyl, indolyl, isoindolyl, benzo[b]thiophenyl, benzimidazolyl, benzothiazolyl, pteridinyl, and phenazinyl, where attachment can occur at any point on said rings, as long as attachment is chemically feasible. Thus, for example, "thiazolyl" refers to thiazol-2-yl, thiazol-4-yl, and thiaz-5-yl.

As used herein, when "heteroaryl" is recited as a possible substituent, the "heteroaryl" group can attach through either a carbon atom or any heteroatom, to the extent that attachment at that point is chemically feasible.

As used herein, the term "heterocyclylene" refers to an optionally substituted bivalent heterocyclyl group (as defined above). The points of attachment may be to the same ring atom or to different ring atoms, as long as attachment is chemically feasible. The two points of attachment can each independently be to either a carbon atom or a heteroatom, as long as attachment is chemically feasible. Examples include, but are not limited to,

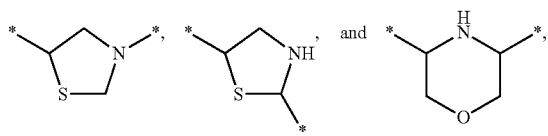

where the asterisks indicate points of attachment.

As used herein, the term "heteroarylene" refers to an optionally substituted bivalent heteroaryl group (as defined above). The points of attachment may be to the same ring atom or to different ring atoms, as long as attachment is chemically feasible. The two points of attachment can each independently be to either a carbon atom or a heteroatom, as long as attachment is chemically feasible. Examples include, but are not limited to,

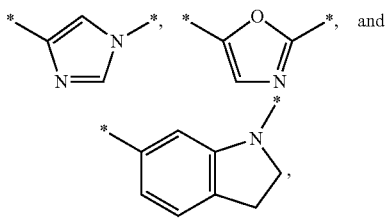

where the asterisks indicate points of attachment.

Various other chemical terms or abbreviations have their standard meaning to the skilled artisan. For example: "hydroxyl" refers to —OH; "methoxy" refers to —OCH$_3$; "cyano" refers to —CN; "amino" refers to —NH$_2$; "methylamino" refers to —NHCH$_3$; "sulfonyl" refers to —SO$_2$—; "carbonyl" refers to —C(O)—; "carboxy" or "carboxyl" refer to —CO$_2$H, and the like. Further, when a name recited multiple moieties, e.g., "methylaminocarbonyl-methyl", an earlier-recited moiety is further from the point of attachment than any later-recited moieties. Thus, a term such as "methylaminocarbonylmethyl" refers to —CH$_2$—C(O)—NH—CH$_3$.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a subject. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the various functional groups represented will be understood to have a point of attachment at the functional group having the hyphen or dash (-) or an asterisk (*). In other words, in the case of —CH$_2$CH$_2$CH$_3$, it will be understood that the point of attachment is the CH$_2$ group at the far left. If a group is recited without an asterisk or a dash, then the attachment point is indicated by the plain and ordinary meaning of the recited group.

When any variable occurs more than one time in any one constituent (e.g., $R^d$), or multiple constituents, its definition on each occurrence is independent of its definition on every other occurrence.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "optionally" means that the subsequently described event(s) may or may not occur.

As used herein, "administer" or "administering" means to introduce, such as to introduce to a subject a compound or composition. The term is not limited to any specific mode of delivery, and can include, for example, intravenous delivery, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

As used herein, "treat" or "treating" or "treatment" can refer to one or more of delaying the progress of a disease or condition, controlling a disease or condition, delaying the onset of a disease or condition, ameliorating one or more symptoms characteristic of a disease or condition, or delaying the recurrence of a disease or condition or characteristic symptoms thereof, depending on the nature of a disease or condition and its characteristic symptoms. "Treat" or "treating" or "treatment" may also refers to inhibiting the disease, either physically, (e.g., stabilization of a discernible symptom), physiologically, (e.g., stabilization of a physical parameter), or both, and to inhibiting at least one physical parameter that may or may not be discernible to the subject. In certain embodiments, "treat" or "treating" or "treatment" refers to delaying the onset of the disease or at least one or more symptoms thereof in a subject which may be exposed to or predisposed to a disease even though that subject does not yet experience or display symptoms of the disease.

As used herein, "subject" may refer any mammal such as, but not limited to, humans. In one embodiment, the subject is a human. In another embodiment, the host is a human who exhibits one or more symptoms characteristic of a disease or condition. The term "subject" does not require one to have any particular status with respect to any hospital, clinic, or research facility (e.g., as an admitted patient, a study participant, or the like). In an embodiment, the subject may be "a subject in need thereof."

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the subject to be treated, and the judgment of the prescribing physician. An appropriate amount in any given instance may be ascertained by those skilled in the art or capable of determination by routine experimentation.

As used herein, the term "compound" includes free acids, free bases, and any salts thereof. Thus, phrases such as "compound of embodiment 1" or "compound of claim 1" refer to any free acids, free bases, and any salts thereof that are encompassed by embodiment 1 or claim 1, respectively.

As used herein, the term "no significant Bach1 inhibitory activity" or "no significant Bach1 inhibitory effect" means that at a concentration of an agent effective to increase cellular levels of free Nrf2 and thereby activate Nrf2 dependent gene transcription, there is no significant level of Bach1 depression.

Bach1 Inhibitor

As used herein, the term "Bach1 Inhibitor" means that after administration the agent inhibits Bach1 repression of Nrf2 dependent gene transcription and elevates expression of one or more ARE-regulated genes.

In an embodiment, a Bach1 inhibitor is a non-naturally occurring agent having a molecular weight less than 2000 daltons. In another embodiment, a Bach1 Inhibitor may also elevate expression of other ARE-regulated genes that are not Nrf2 dependent.

In an embodiment, a Bach1 Inhibitor may be a compound of Formula (I) or a pharmaceutically acceptable salt thereof

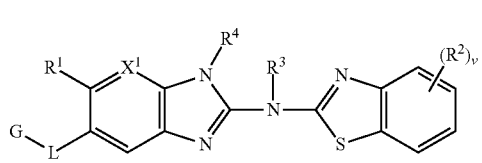

(I)

wherein $X^1$ is =N— or =CH—;

G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, phenyl, heteroaryl, or $NR^hR^k$, where the alkyl, alkylene, cycloalkyl, heterocyclyl, phenyl, and heteroaryl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

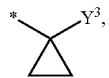

where $Y^3$ is cyclopropyl, —$CF_3$, —$OCF_3$, —$OCH_3$, —$OCH_2CH_3$, —F, —Cl, —OH, —$O(CH_2)_2$—OH, —$O(CH_2)_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —$N(CH_3)_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —$OC(CH_3)_3$, —$NH_2$, —NH—$CH_3$, —NH—$CH_2CH_3$, —$N(CH_3)_2$, —$N(CH_2CH_3)_2$, morpholin-4-yl, 4-methyl-piperazin-1-yl, pyrrolidin-1-yl, or piperazin-1-yl;

L is —$CH_2$—C(O)N($R^6$)—, —C(O)N($R^6$)—, —C(O)—O—, —$SO_2$—, —C(O)—, heteroarylene optionally substituted one or more times with substituents independently selected from $R^x$, or heterocyclylene optionally substituted one or more times with substituents independently selected from $R^x$; or the group -L-G is -cyano;

$R^1$ is hydrogen, $R^a$, phenyl, or heteroaryl, where the phenyl and heteroaryl groups are optionally substituted one or more times with substituents independently selected from IV;

$R^2$ is $R^b$;

$R^3$ is hydrogen, —$C_{1-6}$ alkyl, or —$C_{1-6}$ alkylene-$C_{3-10}$ cycloaklyl, where the alkyl, alkylene, and cycloalkyl groups are optionally substituted one or more times with substituents independently selected from $R^z$;

$R^4$ is —$C_{1-6}$ alkyl or —$C_{1-6}$ alkylene-$C_{3-10}$ cycloaklyl, where the alkyl, alkylene, and cycloalkyl groups are optionally substituted one or more times with substituents independently selected from $R^y$;

$R^6$ is hydrogen, —$C_{1-6}$ alkyl, —$C_{1-6}$ alkylene-$C_{3-10}$ cycloaklyl, where the alkyl, alkylene, and cycloalkyl groups are optionally substituted one or more times with substituents independently selected from IV;

$R^a$ is
a) -halogen,
b) —$C_{1-6}$ alkyl,
c) cycloalkyl,
d) -heterocyclyl,
e) -cyano,
f) —$CF_3$,
g) —$OCF_3$,
h) —O—$R^d$,
i) —$S(O)_w$—$R^d$,
j) —$S(O)_2O$—$R^d$,
k) —$NR^dR^e$,
l) —C(O)—$R^d$,
m) —C(O)—O—$R^d$,
n) —OC(O)—$R^d$,
o) —C(O)$NR^dR^e$,
p) —C(O)-heterocyclyl,
q) —$NR^dC(O)R^e$,
r) —OC(O)$NR^dR^e$,
s) —$NR^dC(O)OR^d$, or
t) —$NR^dC(O)NR^dR^e$,
where the alkyl, cycloalkyl, and heterocyclyl groups are optionally substituted one or more times with substituents independently selected from BY;

$R^b$ is
a) -halogen,
b) —$C_{1-6}$ alkyl,
c) —$C_{3-10}$ cycloalkyl,
d) -heterocyclyl,
e) -phenyl,
f) -heteroaryl,
g) -cyano,
h) —$CF_3$,
i) —$OCF_3$,
j) —O—$R^f$,
k) —$S(O)_w$—$R^f$,
l) —$S(O)_2O$—$R^f$,
m) —$NR^fR^g$,
n) —C(O)—$R^f$,
o) —C(O)—O—$R^f$,
p) —OC(O)—$R^f$,
q) —C(O)$NR^fR^g$,
r) —C(O)-heterocyclyl,
s) —$NR^fC(O)R^g$,
t) —OC(O)$NR^fR^g$,
u) —$NR^fC(O)OR^f$, or v) —NR$^f$C(O)NR$^f$R$^g$,
where the alkyl, cycloalkyl, heterocyclyl, phenyl, and heteroaryl groups are optionally substituted one or more times with substituents independently selected from R$^z$;

R$^c$ is
a) -halogen,
b) —C$_{1-6}$ alkyl,
c) cycloalkyl,
d) -heterocyclyl,
e) -cyano,
f) —CF$_3$,
g) —OCF$_3$,
h) —O—R$^h$,
i) —S(O)$_w$—R$^h$,
j) —S(O)$_2$O—R$^h$,
k) —NR$^h$R$^k$,
l) —C(O)—R$^h$,
m) —C(O)—O—R$^h$,
n) —OC(O)—R$^h$,
o) —C(O)NR$^h$R$^k$,
p) —C(O)-heterocyclyl,
q) —NR$^h$C(O)R$^k$,
r) —OC(O)NR$^h$R$^k$,
s) —NR$^h$C(O)OR$^k$,
t) —NR$^h$C(O)NR$^h$R$^k$,
u) —NR$^h$S(O)$_w$R$^k$,
v) -phenyl,
w) -heteroaryl, or
x) —O—(C$_{1-4}$ alkylene)-O—(C$_{1-4}$ alkylene)-N(R$^h$)C(O)—OR$^k$, where the alkylene, alkyl, cycloalkyl, heterocyclyl, phenyl, and heteroaryl groups are optionally substituted one or more times with substituents independently selected from R$^x$;

R$^d$ and R$^e$ are independently hydrogen, C$_{1-6}$ alkyl, or C$_{3-10}$ cycloalkyl, where the alkyl and cycloalkyl groups are optionally substituted one or more times with substituents independently selected from R$^y$; or, if R$^d$ and R$^e$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^y$;

R$^f$ and R$^g$ are independently hydrogen, C$_{1-6}$ alkyl, C$_{3-10}$ cycloalkyl, phenyl, or heteroaryl, where the alkyl, cycloalkyl, phenyl, and heteroaryl groups are optionally substituted one or more times with substituents independently selected from R$^z$; or, if R$^f$ and R$^g$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^z$;

R$^h$ and R$^k$ are independently hydrogen, C$_{1-6}$ alkyl, C$_{3-10}$ cycloalkyl, heterocyclyl, phenyl, or heteroaryl, where the alkyl, cycloalkyl, heterocyclyl, phenyl, and heteroaryl groups are optionally substituted one or more times with substituents independently selected from R$^x$; or, if R$^h$ and R$^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^x$;

R$^y$ is
a) -halogen,
b) —NH$_2$,
c) -cyano,
d) -carboxy,
e) -hydroxy,
f) -thiol,
g) —CF$_3$,
h) —OCF$_3$,
i) —C(O)—NH$_2$,
j) —S(O)$_2$—NH$_2$,
k) oxo,
l) —C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
m) -heterocyclyl optionally substituted one or more times with one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
n) —C$_{3-10}$ cycloalkyl optionally substituted one or more times with one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
o) —O—C$_{1-6}$ alkyl optionally substituted one or more times with one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
p) —O—C$_{3-10}$ cycloalkyl optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
q) —NH—C$_{1-6}$ alkyl optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
r) —N(C$_{1-6}$ alkyl)$_2$ optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
s) —C(O)—C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
t) —C(O)—O—C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
u) —S—C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
v) —S(O)$_2$—C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$, w) —C(O)—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, x) —C(O)—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, y) —S(O)$_2$—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, z) —S(O)$_2$—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, aa) —NH—C(O)—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, or bb) —NH—S(O)$_2$—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$;

$R^x$ is
a) —$R^y$
b) -phenyl, optionally substituted one or more times with one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
c) -heteroaryl, optionally substituted one or more times with one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

$R^z$ is
a) —$R^y$
b) -phenyl,
c) -heteroaryl;
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

v is an integer from 0 to 4, and
w is an integer from 0 to 2.

Embodiment 2

A compound according to embodiment 1 wherein
G is hydrogen, —$C_{1-8}$ alkyl, —$C_{3-10}$ cycloalkyl, —$C_{1-6}$ alkylene-$C_{3-10}$ cycloaklyl, heterocyclyl, phenyl, heteroaryl, or $NR^hR^k$, where the alkyl, alkylene, cycloalkyl, heterocyclyl, phenyl, and heteroaryl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

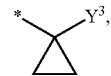

where $Y^3$ is -cyclopropyl, —$CF_3$, —$OCF_3$, —$OCH_3$, —$OCH_2CH_3$, —F, —Cl, —OH, —O($CH_2$)$_2$—OH, —O($CH_2$)$_2$—F, —$SCH_3$, —S(O)$_2$—$CH_3$, —$SCH_2CH_3$, —S(O)$_2CH_2CH_3$, —NH—$CH_3$, —NH—$CH_2CH_3$, —N($CH_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —OC($CH_3$)$_3$, —$NH_2$, —NH—$CH_3$, —NH—$CH_2CH_3$, —N($CH_3$)$_2$, —N($CH_2CH_3$)$_2$, morpholin-4-yl, 4-methyl-piperazin-1-yl, pyrrolidin-1-yl, or piperazin-1-yl;

$R^c$ is
a) -halogen,
b) —$C_{1-6}$ alkyl,
c) cycloalkyl,
d) -heterocyclyl,
e) -cyano,
f) —$CF_3$,
g) —$OCF_3$,
h) —O—$R^h$,
i) —S(O)$_w$—$R^h$,
j) —S(O)$_2$O—$R^h$,
k) —$NR^hR^k$,
l) —C(O)—$R^h$,
m) —C(O)—O—$R^h$,
n) —OC(O)—$R^h$,
o) —C(O)$NR^hR^k$,
p) —C(O)-heterocyclyl,
q) —$NR^h$C(O)$R^k$,
r) —OC(O)$NR^hR^k$,
s) —$NR^h$C(O)$OR^k$,
t) —$NR^h$C(O)$NR^hR^k$,
u) -phenyl,
v) -heteroaryl, or
w) —O—($C_{1-4}$ alkylene)-O—($C_{1-4}$ alkylene)-N($R^h$)C(O)—$OR^k$,
where the alkylene, alkyl, cycloalkyl, heterocyclyl, phenyl, and heteroaryl groups are optionally substituted one or more times with substituents independently selected from $R^x$;

$R^h$ and $R^k$ are independently hydrogen, $C_{1-6}$ alkyl, $C_{3-10}$ cycloalkyl, phenyl, or heteroaryl, where the alkyl, cycloalkyl, phenyl, and heteroaryl groups are optionally substituted one or more times with substituents independently selected from $R^x$; or, if $R^h$ and $R^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from $R^x$; and $R^y$ is
  a) -halogen,
  b) —NH$_2$,
  c) -cyano,
  d) -carboxy,
  e) —C$_{1-6}$ alkyl, optionally substituted one or more times with halogen,
  f) -heterocyclyl, optionally substituted one or more times with halogen,
  g) —C$_{3-10}$ cycloalkyl, optionally substituted one or more times with halogen,
  h) —O—C$_{1-6}$ alkyl, optionally substituted one or more times with halogen,
  i) —O—C$_{3-10}$ cycloalkyl, optionally substituted one or more times with halogen,
  j) -hydroxy,
  k) -thiol,
  l) —CF$_3$,
  m) —OCF$_3$,
  n) —C(O)—C$_{1-6}$ alkyl, optionally substituted one or more times with halogen,
  o) —C(O)—O—C$_{1-6}$ alkyl, optionally substituted one or more times with halogen,
  p) —S—C$_{1-6}$ alkyl, optionally substituted one or more times with halogen, or
  q) —S(O)$_2$—C$_{1-6}$ alkyl, optionally substituted one or more times with halogen.

Embodiment 3

A compound according to embodiment 2, wherein $R^3$ is hydrogen.

Embodiment 4

A compound according to embodiment 2, wherein $R^3$ is methyl.

Embodiment 5

A compound according to any one of embodiments 2 to 4, wherein $X^1$ is =N—.

Embodiment 6

A compound according to any one of embodiments 2 to 4, wherein $X^1$ is =CH—.

Embodiment 7

A compound according to any one of embodiments 2 to 6, wherein
  v is an integer from 0 to 2.

Embodiment 8

A compound according to any one of embodiments 2 to 6, wherein
  v is 0 or 1.

Embodiment 9

A compound according to any one of embodiments 2 to 6, wherein
  v is 1.

Embodiment 10

A compound according to any one of embodiments 2 to 6, wherein
  v is 1, and $R^2$ is attached at either the 5-position or the 6-position of the benzothiazole ring.

Embodiment 11

A compound according to any one of embodiments 2 to 6, wherein
  v is 1, and $R^2$ is attached at the 6-position of the benzothiazole ring.

Embodiment 12

A compound according to any one of embodiments 2 to 68, wherein
  v is 2, and one $R^2$ is attached at the 6-position of the benzothiazole ring.

Embodiment 13

A compound according to any one of embodiments 2 to 6, wherein
  v is 2, and $R^2$ is attached at the 5-position and the 6-position of the benzothiazole ring.

Embodiment 14

A compound according to any one of embodiments 2 to 13, wherein
  $R^2$ is -halogen, —C$_{1-6}$ alkyl, —CF$_3$, —OCF$_3$, —O—R$^f$, or —S(O)$_w$—R$^f$, where the alkyl group is optionally substituted one or more times with substituents independently selected from R$^z$.

Embodiment 15

A compound according to any one of embodiments 2 to 13, wherein
  $R^2$ is -halogen, -methyl, —CF$_3$, —OCF$_3$, —SCF$_3$, —O-heteroaryl, or —S(O)$_2$—CH$_3$.

Embodiment 16

A compound according to any one of embodiments 2 to 13, wherein
  $R^2$ is selected from —F, —CF$_3$, and —OCF$_3$.

Embodiment 17

A compound according to any one of embodiments 2 to 13, wherein
  $R^2$ is —OCF$_3$.

Embodiment 18

A compound according to any one of embodiments 2 to 13, wherein
  $R^2$ is —CF$_3$.

Embodiment 19

A compound according to any one of embodiments 2 to 13, wherein
  $R^2$ is —F.

Embodiment 20

A compound according to any one of embodiments 2 to 13, wherein
  $R^2$ is —Cl.

Embodiment 21

A compound according to any one of embodiments 2 to 20, wherein
R$^4$ is -methyl, -ethyl, -n-propyl, -isopropyl, -n-butyl, -sec-butyl, -isobutyl, -tert-butyl, —(CH$_2$)$_{1-2}$—OCH$_3$, —(CH$_2$)$_{1-2}$—F, —(CH$_2$)$_{1-2}$—Cl, —(CH$_2$)$_{1-2}$—OCF$_3$, —(CH$_2$)$_{1-2}$—NH$_2$, —(CH$_2$)$_{1-2}$—CN, —(CH$_2$)$_{1-2}$—OH, —(CH$_2$)$_{1-2}$—CF$_3$, —(CH$_2$)$_{1-2}$—CO$_2$H, —(CH$_2$)$_{1-2}$—SH, —(CH$_2$)$_{1-2}$—SCH$_3$, —(CH$_2$)$_{1-2}$—S(O)$_2$CH$_3$, —(CH$_2$)$_{1-2}$—OCH$_2$CH$_3$, —(CH$_2$)$_{1-2}$—SCH$_2$CH$_3$, —(CH$_2$)$_{1-2}$—S(O)$_2$CH$_2$CH$_3$, —(CH$_2$)$_{1-2}$—NH—CH$_3$, or —(CH$_2$)$_{1-2}$—N(CH$_3$)$_2$.

Embodiment 22

A compound according to any one of embodiments 2 to 21, wherein
R$^4$ is -methyl, -ethyl, -isopropyl, -isobutyl, —CH$_2$CH$_2$—OCH$_3$, —CH$_2$CH$_2$—F, or CH$_2$CH$_2$—NH$_2$.

Embodiment 23

A compound according to any one of embodiments 2 to 22, wherein
R$^4$ is -methyl, -ethyl, -isopropyl, or -isobutyl.

Embodiment 24

A compound according to any one of embodiments 2 to 23, wherein
R$^4$ is -methyl.

Embodiment 25

A compound according to any one of embodiments 2 to 23, wherein
R$^4$ is -ethyl.

Embodiment 26

A compound according to any one of embodiments 2 to 21, wherein
R$^4$ is —(CH$_2$)$_2$—OCH$_3$, —(CH$_2$)$_2$—F, —(CH$_2$)$_2$—Cl, —(CH$_2$)$_2$—OCF$_3$, —(CH$_2$)$_2$—NH$_2$, —(CH$_2$)$_2$—CN, —(CH$_2$)$_2$—OH, —(CH$_2$)$_2$—CF$_3$, —(CH$_2$)$_2$—CO$_2$H, —(CH$_2$)$_2$—SH, —(CH$_2$)$_2$—SCH$_3$, or —(CH$_2$)$_2$—S(O)$_2$CH$_3$.

Embodiment 27

A compound according to any one of embodiments 2 to 26, wherein
R$^1$ is selected from hydrogen, —OCH$_3$, —F, —Cl, —NH$_2$, -cyano, —OH, —CF$_3$, —OCF$_3$, —SH, —S—C$_{1-6}$ alkyl, —S(O)$_2$—C$_{1-6}$ alkyl, —CO$_2$H, —NH—C$_{1-6}$ alkyl, —N(C$_{1-6}$ alkyl)$_2$, and —NH—C$_{1-6}$ alkyl.

Embodiment 28

A compound according to any one of embodiments 2 to 26, wherein
R$^1$ is selected from —OCH$_3$, —F, —CF$_3$, —OCF$_3$, —N(CH$_3$)$_2$, —N(CH$_2$CH$_3$)$_2$, and —N(CH$_3$)(CH$_2$CH$_3$).

Embodiment 29

A compound according to any one of embodiments 2 to 26, wherein
R$^1$ is selected from hydrogen, —OCH$_3$, and —F.

Embodiment 30

A compound according to any one of embodiments 2 to 26, wherein
R$^1$ is hydrogen.

Embodiment 31

A compound according to any one of embodiments 2 to 30, wherein
G is hydrogen, —C$_{1-8}$ alkyl, —C$_{3-10}$ cycloalkyl, —C$_{1-6}$ alkylene-C$_{3-8}$ cycloalkyl, heterocyclyl, or NR$^h$R$^k$, where the alkyl, alkylene, cycloalkyl, and heterocyclyl groups are optionally substituted one or more times with substituents independently selected from R$^c$; or G is —CH$_2$Y$^3$, —CH$_2$CH$_2$Y$^3$, —CH$_2$CH$_2$CH$_2$Y$^3$, —CH(CH$_3$)CH$_2$Y$^3$, —CH$_2$CH(Y$^3$)CH$_3$, —CH(Y$^3$)CH$_3$, —CH$_2$C(Y$^3$)(CH$_3$)$_2$, —C(Y$^3$)(CH$_3$)$_2$, or

where Y$^3$ is -cyclopropyl, —CF$_3$, —OCF$_3$, —OCH$_3$, —OCH$_2$CH$_3$, —F, —Cl, —OH, —O(CH$_2$)$_2$—OH, —O(CH$_2$)$_2$—F, —SCH$_3$, —S(O)$_2$—CH$_3$, —SCH$_2$CH$_3$, —S(O)$_2$CH$_2$CH$_3$, —NH—CH$_3$, —NH—CH$_2$CH$_3$, —N(CH$_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—CH$_3$, —NH—C(O)—CH$_2$CH$_3$, tetrahydrofuran-2-yl-methyloxy, or —C(O)—Y$^4$, where Y$^4$ is —OH, —OCH$_3$, —OCH$_2$CH$_3$, —OC(CH$_3$)$_3$, —NH$_2$, —NH—CH$_3$, —NH—CH$_2$CH$_3$, —N(CH$_3$)$_2$, —N(CH$_2$CH$_3$)$_2$, morpholin-4-yl, 4-methyl-piperazin-1-yl, pyrrolidin-1-yl, or piperazin-1-yl;

L is —CH$_2$—C(O)N(R$^6$)—, —C(O)N(R$^6$)—, —C(O)—O—, —SO$_2$—, —C(O)—, or heterocyclylene optionally substituted one or more times with substituents independently selected from R$^x$; or the group -L-G is -cyano;

R$^1$ is hydrogen or R$^a$;

R$^c$ is
a) -halogen,
b) —C$_{1-6}$ alkyl,
c) —C$_{3-10}$ cycloalkyl,
d) -heterocyclyl,
e) -cyano,
f) —CF$_3$,
g) —OCF$_3$,
h) —O—R$^h$,
i) —S(O)$_w$—R$^h$,
j) —S(O)$_2$O—R$^h$,
k) —NR$^h$R$^k$,
l) —C(O)—R$^h$,
m) —C(O)—O—R$^h$,
n) —OC(O)—R$^h$, o) —C(O)NR$^h$R$^k$,
p) —C(O)-heterocyclyl,
q) —NR$^h$C(O)R$^k$,
r) —OC(O)NR$^h$R$^k$,
s) —NR$^h$C(O)OR$^k$,
t) —NR$^h$C(O)NR$^h$R$^k$, or
u) —O—(C$_{1-4}$ alkylene)-O—(C$_{1-4}$ alkylene)-N(R$^h$)C(O)—OR$^k$, where the alkylene, alkyl, cycloalkyl, and heterocyclyl groups are optionally substituted one or more times with substituents independently selected from R$^x$;

R$^h$ and R$^k$ are independently hydrogen, C$_{1-6}$ alkyl, or C$_{3-10}$ cycloalkyl, where the alkyl, and cycloalkyl groups are optionally substituted one or more times with substituents independently selected from R$^x$; or, if R$^h$ and R$^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^x$; and R$^x$ is R$^y$.

Embodiment 32

A compound according to any one of embodiments 2 to 31, wherein
-L-G is not -cyano.

Embodiment 33

A compound according to any one of embodiments 2 to 32, wherein
-L-G is —C(O)NR$^h$R$^k$.

Embodiment 34

A compound according to any one of embodiments 2 to 32, wherein
L is —C(O)N(R$^6$)— or —C(O)—O—.

Embodiment 35

A compound according to any one of embodiments 2 to 32, wherein
L is —C(O)N(R$^6$)—.

Embodiment 36

A compound according to any one of embodiments 2 to 32, wherein
L is not —CH$_2$—C(O)N(R$^6$)—.

Embodiment 37

A compound according to any one of embodiments 2 to 32, wherein
L is —C(O)—O—.

Embodiment 38

A compound according to any one of embodiments 2 to 32, wherein
L is —C(O)—.

Embodiment 39

A compound according to any one of embodiments 2 to 32, wherein
L is —S(O)$_2$—.

Embodiment 40

A compound according to any one of embodiments 2 to 30, wherein
L is heteroarylene optionally substituted one or more times with substituents independently selected from IV.

Embodiment 41

A compound according to any one of embodiments 2 to 40, wherein
R$^6$ is hydrogen.

Embodiment 42

A compound according to any one of embodiments 2 to 40, wherein
R$^6$ is hydrogen or -methyl.

Embodiment 43

A compound according to any one of embodiments 2 to 42, wherein
G is hydrogen, —C$_{1-8}$ alkyl, —C$_{3-10}$ cycloalkyl, or —C$_{1-6}$ alkylene-C$_{3-8}$ cycloaklyl, where the alkyl, cycloalkyl, and alkylene groups are optionally substituted one or more times with substituents independently selected from R$^x$.

Embodiment 44

A compound according to any one of embodiments 2 to 42, wherein
G is —H, -methyl, -ethyl, -n-propyl, -isopropyl, -isobutyl, —CH$_2$Y$^3$, —CH$_2$CH$_2$Y$^3$, —CH$_2$CH$_2$CH$_2$Y$^3$, —CH(CH$_3$)CH$_2$Y$^3$, —CH$_2$CH(Y$^3$)CH$_3$, —CH(Y$^3$)CH$_3$, —CH$_2$C(Y$^3$)(CH$_3$)$_2$, or —C(Y$^3$)(CH$_3$)$_2$, where Y$^3$ is -cyclopropyl, —CF$_3$, —OCF$_3$, —OCH$_3$, —OCH$_2$CH$_3$, —F, —OH, —O(CH$_2$)$_2$—OH, —O(CH$_2$)$_2$—F, —SCH$_3$, —S(O)$_2$—CH$_3$, —SCH$_2$CH$_3$, —S(O)$_2$CH$_2$CH$_3$, —NH—CH$_3$, —NH—CH$_2$CH$_3$, —N(CH$_3$)$_2$, —NH—C(O)—CH$_3$, —NH—C(O)—CH$_2$CH$_3$, or C(O)—Y$^4$, where Y$^4$ is —OH, —OCH$_3$, —OCH$_2$CH$_3$, —OC(CH$_3$)$_3$, —NH$_2$, —NH—CH$_3$, —NH—CH$_2$CH$_3$, —N(CH$_3$)$_2$, or —N(CH$_2$CH$_3$)$_2$.

Embodiment 45

A compound according to any one of embodiments 2 to 42, wherein
G is -methyl, -ethyl, -n-propyl, -isopropyl, or -isobutyl, where each is optionally substituted one or more times with substituents independently selected from —CF$_3$, —OCF$_3$, —OCH$_3$, —OCH$_2$CH$_3$, —F, —OH, —O(CH$_2$)$_2$—OH, —O(CH$_2$)$_2$—F, —SCH$_3$, —SCH$_2$CH$_3$, —NH—CH$_3$, —NH—CH$_2$CH$_3$, and —N(CH$_3$)$_2$.

Embodiment 46

A compound according to any one of embodiments 2 to 42, wherein
G is H.

Embodiment 47

A compound according to any one of embodiments 2 to 42, wherein
G is $C_{1-8}$ alkyl optionally substituted one or more times with halogen.

Embodiment 48

A compound according to any one of embodiments 2 to 42, wherein
G is $C_{3-10}$ cycloalkyl optionally substituted one or more times with halogen.

Embodiment 49

A compound according to any one of embodiments 2 to 42, wherein
G is heterocyclyl optionally substituted one or more times with halogen.

Embodiment 50

A compound according to any one of embodiments 2 to 42, wherein
G is —$C_{1-6}$ alkylene-$C_{3-10}$ cycloalkyl optionally substituted one or more times with halogen.

Embodiment 51

A compound according to any one of embodiments 2 to 42, wherein
G is $NR^hR^k$.

Embodiment 52

A compound according to any one of embodiments 2 to 42, wherein
G is —$CH_2$—$R^c$.

Embodiment 53

A compound according to any one of embodiments 2 to 42, wherein
G is —$CH_2CH_2$—$R^c$.

Embodiment 54

A compound according to any one of embodiments 2 to 42, wherein
G is —$CH_2CH_2CH_2$—$R^c$.

Embodiment 55

A compound according to any one of embodiments 2 to 42, wherein
G is —$CH(CH_3)CH_2R^c$.

Embodiment 56

A compound according to any one of embodiments 2 to 42, wherein
G is —$CH_2CH(R^c)CH_3$.

Embodiment 57

A compound according to any one of embodiments 2 to 42, wherein
G is —$CH(R^c)CH_3$.

Embodiment 58

A compound according to any one of embodiments 2 to 42, wherein
G is —$CH_2C(R^c)(CH_3)_2$.

Embodiment 59

A compound according to any one of embodiments 2 to 42, wherein
G is —$C(R^c)(CH_3)_2$.

Embodiment 60

A compound according to any one of embodiments 2 to 42, wherein
G is imidazol-2-yl, thiazol-2yl, oxazol-2-yl, pyrazol1-yl, furan-2yl, thiophen-2-yl, pyrrol-1-yl, 1H-1,2,4-triazolyl-3-yl, 5-methyl-1H-1,2,4-triazolyl-3-yl, —$(CH_2)_{1-3}$-(imidazol-2-yl), —$(CH_2)_{1-3}$-(thiazol-2yl), —$(CH_2)_{1-3}$-(oxazol-2-yl), —$(CH_2)_{1-3}$-(pyrazol1-yl), —$(CH_2)_{1-3}$-(furan-2yl), —$(CH_2)_{1-3}$-(thiophen-2-yl), —$(CH_2)_{1-3}$-(pyrrol-1-yl), —$(CH_2)_{1-3}$-(1H-1,2,4-triazolyl-3-yl), or —$(CH_2)_{1-3}$-(5-methyl-1H-1,2,4-triazolyl-3-yl).

Embodiment 61

A compound according to any one of embodiments 2 to 60, wherein
the compound is in its free (non-salted) form.

Embodiment 62

A compound according to any one of embodiments 2 to 60, wherein
the compound is in the form of a pharmaceutically acceptable salt.

Embodiment 63

A compound according to any one of embodiments 1 to 62, wherein
any "heterocyclyl" group present in the compound is selected from the group consisting of: azetidin-1-yl, azetidin-2-yl, azetidin-3-yl, pyrrolidin-1-yl, pyrrolidin-2-yl, pyrrolidin-3-yl, tetrahydrofuran-2-yl, tetrahydrofuran-3-yl, tetrahydrothiophen-2-yl, tetrahydrothiophen-3-yl, pyrazolidin-1-yl, pyrazolidin-3-yl, pyrazolidin-4-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolodin-5-yl, isothiazolidin-2-yl, isothiazolidin-3-yl, isothiazolidin-4-yl, isothiazolodin-5-yl, 1,3-dioxolan-2-yl, 1,3-dioxolan-4-yl, 1,3-oxathiolan-2-yl, 1,3-oxathiolane-4-yl, 1,3-oxathiolan-5-yl, 1,2-dithiolan-3-yl, 1,2-dithiolan-4-yl, 1,3-dithiolan-2-yl, 1,3-dithiolan-4-yl, piperidin-1-yl, piperidin-2-yl, piperidin-3-yl, piperidin-4-yl, tetrahydropyran-2-yl, tetrahydropyran-3-yl, tetrahydropyran-4-yl, thian-2-yl, thian-3-yl, thian-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl, 1,4-dioxan-2-yl, 1,3-dioxan-2-yl, 1,3-dioxan-4-yl, 1,3-dioxan-5-yl, 1,4- dithian-2-yl, 1,3-dithian-2-yl, 1,3-dithian-4-yl, 1,3-dithian-5-yl, 1,2-dithian-3-yl, 1,2-dithian-4-yl, azepan-1-yl, azepan-2-yl, azepan-3-yl, and azepan-4-yl, where each of these named rings may optionally be substituted one or more times with substituents independently selected from halogen, —$NH_2$, cyano, carboxy, $C_{1-4}$ alkyl, $C_{3-10}$ cycloalkyl, hydroxyl, thiol, —$CF_3$, —$OCF_3$, —O—$C_{1-4}$ alkyl, —NH—$C_{1-4}$ alkyl, —N($C_{1-4}$ alkyl)$_2$, —S—$C_{1-4}$ alkyl, —S(O)$_2$—$C_{1-4}$ alkyl, —C(O)—$C_{1-4}$ alkyl, —C(O)O—$C_{1-4}$ alkyl, —C(O)$NH_2$, —C(O)NH—$C_{1-4}$ alkyl, and —C(O)N($C_{1-4}$alkyl)$_2$, and where any nitrogen atom in any of these named rings may optionally be oxidized when chemically feasible, and where any sulfur atom in any of these named rings may optionally be oxidized once or twice when chemically feasible.

Embodiment 64

A compound according to any one of embodiments 1 to 63, wherein
any "heteroaryl" group present in the compound is selected from the group consisting of: 1H-pyrrol-1-yl, 1H-pyrrol-2-yl, 1H-pyrrol-3-yl, furan-2-yl, furan-3-yl, thiophen-2-yl, thiophen-3-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl, 1H-1,2,4-triazol-5-yl, furazan-3-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1H-indol-1-yl, 1H-indol-2-yl, 1H-indol-3-yl, 2H-isoindol-1-yl, 2H-isoindol-2-yl, quinolin-2-yl, quinolin-3-yl, quinolin-4-yl, isoquinolin-1-yl, isoquinolin-3-yl, isoquinolin-4-yl, benzoxazol-2-yl, benzothiazol-2-yl, 1H-benzimidazol-1-yl, 1H-benzimidazol-2-yl, benzofuran-2-yl, benzofuran-3-yl, benzothiophen-2-yl, and benzothiophen-3-yl, where each of these named rings may optionally be substituted one or more times with substituents independently selected from halogen, —$NH_2$, cyano, carboxy, $C_{1-4}$ alkyl, $C_{3-10}$ cycloalkyl, hydroxyl, thiol, —$CF_3$, —$OCF_3$, —O—$C_{1-4}$ alkyl, —NH—$C_{1-4}$ alkyl, —N($C_{1-4}$ alkyl)$_2$, —S—$C_{1-4}$ alkyl, —S(O)$_2$—$C_{1-4}$ alkyl, —C(O)—$C_{1-4}$ alkyl, —C(O)O—$C_{1-4}$ alkyl, —C(O)$NH_2$, —C(O)NH—$C_{1-4}$ alkyl, —C(O)N($C_{1-4}$alkyl)$_2$, and phenyl.

Embodiment 65

A compound according to any one of embodiments 1 to 64, wherein
any "heteroarylene" group present in the compound is selected from the group consisting of: 1H-pyrrol-2,5-diyl, furan-2,5-diyl, thiophen-2,5-diyl, 1H-imidazol-2,4-diyl, 1H-imidazol-2,5-diyl, oxazol-2,4-diyl, oxazol-2,5-diyl, thiazol-2,4-diyl, thiazol-2,5-diyl, 1H-1,2,4-triazol-3,5-diyl, and 2H-isoindol-1,3-diyl, where each of these named rings may optionally be substituted one or more times with substituents independently selected from halogen, —$NH_2$, cyano, carboxy, —$C_{1-4}$ alkyl, —$C_{3-10}$ cycloalkyl, hydroxyl, thiol, —$CF_3$, —$OCF_3$, —O—$C_{1-4}$ alkyl, —NH—$C_{1-4}$ alkyl, —N($C_{1-4}$ alkyl)$_2$, —S—$C_{1-4}$ alkyl, —S(O)$_2$—$C_{1-4}$ alkyl, —C(O)—$C_{1-4}$ alkyl, —C(O)O—$C_{1-4}$ alkyl, —C(O)$NH_2$, —C(O)NH—$C_{1-4}$ alkyl, —C(O)N($C_{1-4}$ alkyl)$_2$, and phenyl.

Embodiment 66

A compound according to embodiment 1.

Embodiment 67

A compound according to embodiment 66, wherein $R^3$ is hydrogen.

Embodiment 68

A compound according to embodiment 66, wherein $R^3$ is methyl.

Embodiment 69

A compound according to embodiment 66, wherein $R^3$ is ethyl.

Embodiment 70

A compound according to embodiment 66, wherein $R^3$ is isopropyl.

Embodiment 71

A compound according to any one of embodiment 66 to 70, wherein $X^1$ is =N—.

Embodiment 72

A compound according to any one of embodiments 66 to 70, wherein $X^1$ is =CH—.

Embodiment 73

A compound according to any one of embodiments 66 to 72, wherein
v is 0, 1 or 2.

Embodiment 74

A compound according to any one of embodiments 66 to 72, wherein
v is 1 or 2.

Embodiment 75

A compound according to any one of embodiments 66 to 72, wherein
v is 1.

Embodiment 76

A compound according to any one of embodiments 66 to 72, wherein
v is 1, and $R^2$ is attached at either the 5-position or the 6-position of the benzothiazole ring.

Embodiment 77

A compound according to any one of embodiments 66 to 72, wherein v is 1, and $R^2$ is attached at the 6-position of the benzothiazole ring.

Embodiment 78

A compound according to any one of embodiments 66 to 72, wherein
v is 2, and one $R^2$ is attached at the 6-position of the benzothiazole ring.

Embodiment 79

A compound according to any one of embodiments 66 to 72, wherein
v is 2, and $R^2$ is attached at the 5-position and the 6-position of the benzothiazole ring.

Embodiment 80

A compound according to any one of embodiments 66 to 79, wherein
$R^2$ is -halogen, —$C_{1-6}$ alkyl, —$CF_3$, —$OCF_3$, —O—$R^f$, or —$S(O)_w$—$R^f$, where the alkyl group is optionally substituted one or more times with substituents independently selected from $R^z$.

Embodiment 81

A compound according to any one of embodiments 66 to 79, wherein
$R^2$ is -halogen, -methyl, ethyl, isopropyl, —$OCH_3$, —$OCH_2CH_3$, —$OCH(CH_3)_2$, —$CF_3$, —$OCF_3$, —$SCF_3$, —$S(O)_2$—$CH_3$, —O-phenyl, —O-(2-pyridyl), —O-(3-pyridyl), or —O-(4-pyridyl).

Embodiment 82

A compound according to any one of embodiments 66 to 79, wherein
$R^2$ is -halogen, -methyl, ethyl, isopropyl, —$OCH_3$, —$OCH_2CH_3$, —$OCH(CH_3)_2$, —$CF_3$, —$OCF_3$, —$SCF_3$, —$S(O)_2$—$CH_3$, or —O-(3-pyridyl).

Embodiment 83

A compound according to any one of embodiments 66 to 79, wherein
$R^2$ is —Cl, —F, —$CF_3$, or —$OCF_3$.

Embodiment 84

A compound according to any one of embodiments 66 to 79, wherein
$R^2$ is —$OCF_3$.

Embodiment 85

A compound according to any one of embodiments 66 to 79, wherein
$R^2$ is —$CF_3$.

Embodiment 86

A compound according to any one of embodiments 66 to 79, wherein
$R^2$ is —F.

Embodiment 87

A compound according to any one of embodiments 66 to 79, wherein
$R^2$ is —Cl.

Embodiment 88

A compound according to any one of embodiments 66 to 79, wherein
$R^2$ is —$SO_2CH_3$.

Embodiment 89

A compound according to any one of embodiments 66 to 79, wherein
$R^2$ is methyl, ethyl, or isopropyl.

Embodiment 90

A compound according to any one of embodiments 66 to 79, wherein
$R^2$ is methyl.

Embodiment 91

A compound according to any one of embodiments 66 to 79, wherein
$R^2$ is —$OCH_2CH_3$.

Embodiment 92

A compound according to any one of embodiments 66 to 79, wherein
$R^2$ is —O-phenyl.

Embodiment 93

A compound according to any one of embodiments 66 to 79, wherein
$R^2$ is —O-(2-pyridyl), —O-(3-pyridyl), or —O-(4-pyridyl).

Embodiment 94

A compound according to any one of embodiments 66 to 79, wherein
$R^2$ is —O-(3-pyridyl).

Embodiment 95

A compound according to any one of embodiments 66 to 94, wherein
$R^4$ is -methyl, -ethyl, -n-propyl, -isopropyl, -n-butyl, -sec-butyl, -isobutyl, -tert-butyl, —$(CH_2)_{1-2}$—$OCH_3$, —$(CH_2)_{1-2}$—F, —$(CH_2)_{1-2}$—Cl, —$(CH_2)_{1-2}$—$OCF_3$, —$(CH_2)_{1-2}$—$NH_2$, —$(CH_2)_{1-2}$—CN, —$(CH_2)_{1-2}$—OH, —$(CH_2)_{1-2}$—$CF_3$, —$(CH_2)_{1-2}$—$CO_2H$, —$(CH_2)_{1-2}$—SH, —$(CH_2)_{1-2}$—$SCH_3$, —$(CH_2)_{1-2}$—$S(O)_2CH_3$, —$(CH_2)_{1-2}$—$OCH_2CH_3$, —$(CH_2)_{1-2}$—$SCH_2CH_3$, —$(CH_2)_{1-2}$—$S(O)_2CH_2CH_3$, —$(CH_2)_{1-2}$—NH—$CH_3$, or —$(CH_2)_{1-2}$—$N(CH_3)_2$.

Embodiment 96

A compound according to any one of embodiments 66 to 94, wherein
$R^4$ is -methyl, -ethyl, -isopropyl, -isobutyl, —$CH_2CH_2$—$OCH_3$, —$CH_2CH_2$—F, —$CH_2CH_2$—$NH_2$, or —$CH_2CH_2$—NH—$CH_3$.

Embodiment 97

A compound according to any one of embodiments 66 to 94, wherein
$R^4$ is -methyl, -ethyl, -isopropyl, or -isobutyl.

Embodiment 98

A compound according to any one of embodiments 66 to 94, wherein
$R^4$ is methyl.

Embodiment 99

A compound according to any one of embodiments 66 to 94, wherein
$R^4$ is -ethyl.

Embodiment 100

A compound according to any one of embodiments 66 to 94, wherein
$R^4$ is -isopropyl.

Embodiment 101

A compound according to any one of embodiments 66 to 94, wherein
$R^4$ is -isobutyl.

Embodiment 102

A compound according to any one of embodiments 66 to 94, wherein
$R^4$ is —$CH_2CH_2$—$OCH_3$.

Embodiment 103

A compound according to any one of embodiments 66 to 94, wherein
$R^4$ is —$CH_2CH_2$—F.

Embodiment 104

A compound according to any one of embodiments 66 to 94, wherein
$R^4$ is —$CH_2CH_2$—$NH_2$.

Embodiment 105

A compound according to any one of embodiments 66 to 94, wherein
$R^4$ is —$CH_2CH_2$—NH—$CH_3$.

Embodiment 106

A compound according to any one of embodiments 66 to 105, wherein
$R^1$ is hydrogen, —$OCH_3$, —F, —Cl, —$NH_2$, -cyano, —OH, —$CF_3$, —$OCF_3$, —SH, —S—$C_{1-6}$ alkyl, —$S(O)_2$—$C_{1-6}$ alkyl, —$CO_2H$, —NH—$C_{1-6}$ alkyl, —N($C_{1-6}$ alkyl)$_2$, or —NH—$C_{1-6}$ alkyl.

Embodiment 107

A compound according to any one of embodiments 66 to 105, wherein
$R^1$ is —$OCH_3$, —F, —$CF_3$, —$OCF_3$, —N($CH_3$)$_2$, —N($CH_2CH_3$)$_2$, or —N($CH_3$)($CH_2CH_3$).

Embodiment 108

A compound according to any one of embodiments 66 to 105, wherein
$R^1$ is hydrogen, —$OCH_3$, or —F.

Embodiment 109

A compound according to any one of embodiments 66 to 105, wherein
$R^1$ is hydrogen.

Embodiment 110

A compound according to any one of embodiments 66 to 105, wherein
$R^1$ is —F.

Embodiment 111

A compound according to any one of embodiments 66 to 105, wherein
$R^1$ is —$OCH_3$.

Embodiment 112

A compound according to any one of embodiments 66 to 105 wherein
$R^1$ is —N($CH_2CH_3$)$_2$.

Embodiment 113

A compound according to any one of embodiments 66 to 112, wherein
G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, or $NR^hR^k$, where the alkyl, alkylene, cycloalkyl, and heterocyclyl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

where $Y^3$ is cyclopropyl, —$CF_3$, —$OCF_3$, —$OCH_3$, —$OCH_2CH_3$, —F, —Cl, —OH, —$O(CH_2)_2$—OH, —$O(CH_2)_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —N($CH_3$)$_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —$OC(CH_3)_3$, —$NH_2$, —NH—$CH_3$, —NH—$CH_2CH_3$, —N($CH_3$)$_2$, —N($CH_2CH_3$)$_2$, morpholin-4-yl, 4-methyl-piperazin-1-yl, pyrrolidin-1-yl, or piperazin-1-yl;
L is —$CH_2$—C(O)N($R^6$)—, —C(O)N($R^6$)—, —C(O)—O—, —$SO_2$—, —C(O)—, or heterocyclylene optionally substituted one or more times with substituents independently selected from $R^x$; or the group -L-G is -cyano;
$R^1$ is hydrogen or $R^a$;
$R^c$ is
a) -halogen,
b) —$C_{1-6}$ alkyl,
c) cycloalkyl, d) -heterocyclyl,
e) -cyano,
f) —CF$_3$,
g) —OCF$_3$,
h) —O—R$^h$,
i) —S(O)$_w$—R$^h$,
j) —S(O)$_2$O—R$^h$,
k) —NR$^h$R$^k$,
l) —C(O)—R$^h$,
m) —C(O)—O—R$^h$,
n) —OC(O)—R$^h$,
o) —C(O)NR$^h$R$^k$,
p) —C(O)-heterocyclyl,
q) —NR$^h$C(O)R$^k$,
r) —OC(O)NR$^h$R$^k$,
s) —NR$^h$C(O)OR$^k$,
t) —NR$^h$C(O)NR$^h$R$^k$,
u) —NR$^h$S(O)$_w$R$^k$, or
v) —O—(C$_{1-4}$ alkylene)-O—(C$_{1-4}$ alkylene)-N(R$^h$)C(O)—OR$^k$, where the alkylene, alkyl, cycloalkyl, and heterocyclyl groups are optionally substituted one or more times with substituents independently selected from R$^x$;

R$^h$ and R$^k$ independently are hydrogen, C$_{1-6}$ alkyl, C$_{3-10}$ cycloalkyl, or heterocyclyl, where the alkyl, cycloalkyl, and heterocyclyl groups are optionally substituted one or more times with substituents independently selected from R$^x$; or, if R$^h$ and R$^k$ are both attached to the same nitrogen atom, together with that nitrogen atom may optionally form a heterocyclic ring selected from azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^x$; and R$^x$ is R$^y$.

Embodiment 114

A compound according to any one of embodiments 66 to 112, wherein
-L-G is not -cyano.

Embodiment 115

A compound according to any one of embodiments 66 to 112, wherein
L is —C(O)N(R$^6$)—.

Embodiment 116

A compound according to embodiment 115 wherein R$^6$ is hydrogen.

Embodiment 117

A compound according to embodiment 115 wherein R$^6$ is methyl.

Embodiment 118

A compound according to embodiment 117 wherein G is —N(CH$_3$)$_2$.

Embodiment 119

A compound according to any one of embodiments 66 to 112, wherein
-L-G is —C(O)NR$^h$R$^k$.

Embodiment 120

A compound according to embodiment 119, wherein NR$^h$R$^k$ is pyrrolidino, piperidino, piperazino, 4-methylpiperazino, or morpholino, where each of the foregoing is optionally substituted once with —(CH$_2$)$_{1-3}$—OH.

Embodiment 121

A compound according to embodiment 120, wherein NR$^h$R$^k$ is pyrrolidino, 4-(2-hydroxyethyl)-piperazino, or 4-(3-hydroxypropyl)-piperidino.

Embodiment 122

A compound according to embodiment 119, wherein NR$^h$R$^k$ is N[(CH$_2$)$_2$—OH]$_2$.

Embodiment 123

A compound according to any one of embodiments 66 to 114, wherein
L is not —CH$_2$—C(O)N(R$^6$)—.

Embodiment 124

A compound according to any one of embodiments 66 to 123, wherein
L is not heterocyclylene.

Embodiment 125

A compound according to any one of embodiments 66 to 112, wherein
L is —S(O)$_2$—.

Embodiment 126

A compound according to embodiment 125, wherein G is methyl or —CF$_3$.

Embodiment 127

A compound according to any one of embodiments 66 to 112, wherein
L is heteroarylene optionally substituted one or more times with substituents independently selected from R$^x$.

Embodiment 128

A compound according to embodiment 127, wherein -L-G is imidazol-2-yl, 1,2,4-triazol-3-yl, or 5-methyl-1,2,4-triazol-3-yl.

Embodiment 129

A compound according to any one of embodiments 66 to 112, wherein
L is —C(O)—O—.

Embodiment 130

A compound according to embodiment 129, wherein G is hydrogen, or —C$_{1-8}$ alkyl, where the alkyl group is optionally substituted one or more times with substituents independently selected from R$^c$.

Embodiment 131

A compound according to embodiment 130, wherein G is methyl or ethyl.

Embodiment 132

A compound according to embodiment 130, wherein G is hydrogen.

Embodiment 133

A compound according to any one of embodiments 66 to 116, wherein
G is —$C_{1-8}$ alkyl, —$C_{3-10}$ cycloalkyl, —$C_{1-6}$ alkylene-$C_{3-10}$ cycloaklyl, heterocyclyl, or —$C_{1-6}$ alkylene-$C_{3-10}$ heterocyclyl, where the alkyl, alkylene, cycloalkyl, and heterocyclyl groups are optionally substituted one or more times with substituents independently selected from $R^c$.

Embodiment 134

A compound according to embodiment 133, wherein G is —$C_{1-8}$ alkyl optionally substituted one or more times with substituents independently selected from $R^c$.

Embodiment 135

A compound according to embodiment 134, wherein G is methyl, ethyl, isopropyl, n-propyl, n-butyl, sec-butyl, or isobutyl.

Embodiment 136

A compound according to embodiment 134, wherein G is methyl, ethyl, or n-propyl.

Embodiment 137

A compound according to embodiment 134, wherein G is 2-fluoroethyl, 2,2-difluoroethyl, or 2,2,2-trifluoroethyl.

Embodiment 138

A compound according to embodiment 134, wherein G is 2-cyanoethyl.

Embodiment 139

A compound according to embodiment 134, wherein G is —$C_{1-8}$ alkyl substituted once by —C(O)—O—$R^h$.

Embodiment 140

A compound according to embodiment 139, wherein G is —$CH_2$—C(O)—O—$R^h$.

Embodiment 141

A compound according to embodiment 140, wherein $R^h$ is hydrogen or methyl.

Embodiment 142

A compound according to embodiment 139, wherein G is —$CH_2CH_2$—C(O)—O—$R^h$.

Embodiment 143

A compound according to embodiment 142, wherein $R^h$ is hydrogen or methyl.

Embodiment 144

A compound according to embodiment 139, wherein G is —$C(CH_3)_2$—C(O)—O—$R^h$.

Embodiment 145

A compound according to embodiment 144, wherein $R^h$ is hydrogen or methyl.

Embodiment 146

A compound according to embodiment 139, wherein G is —$CH(CH_3)$—C(O)—O—$R^h$.

Embodiment 147

A compound according to embodiment 146, wherein $R^h$ is hydrogen or methyl.

Embodiment 148

A compound according to embodiment 134, wherein G is —$C_{1-8}$ alkyl substituted once by —C(O)$NR^hR^k$.

Embodiment 149

A compound according to embodiment 148, wherein G is $CH_2$—C(O)—$NR^hR^k$.

Embodiment 150

A compound according to embodiment 149, wherein $NR^hR^k$ is methylamino, dimethylamino, or diethylamino.

Embodiment 151

A compound according to embodiment 149, wherein $NR^hR^k$ is thiomorpholino or 1,1-dioxothiomorpholino.

Embodiment 152

A compound according to embodiment 149, wherein $NR^hR^k$ is morpholino, pyrrolidino, piperidino, piperazino, or 4-methylpiperazino.

Embodiment 153

A compound according to embodiment 149, wherein $NR^hR^k$ is pyrrolidino, 3-hydroxy-pyrrolidino, 3-methoxy-pyrrolidino, 3-amino-pyrrolidino, 3-(methylamino)-pyrrolidino, 3-(dimethylamino)-pyrrolidino, 2-(hydroxymethyl)-pyrrolidino, 2-(dimethylaminocarbonyl)-pyrrolidino or 3,4-dihydroxy-pyrrolidino.

Embodiment 154

A compound according to embodiment 149, wherein $NR^hR^k$ is piperazino, 4-methylpiperazino, 4-(methylsulfonyl)-piperazino, or 4-(dimethylaminosulfonyl)-piperazino.

Embodiment 155

A compound according to embodiment 149, wherein $NR^hR^k$ is piperidino, 3-hydroxypiperidino, 4-hydroxypiperidino, 2-(hydroxymethyl)-piperidino, 3-(hydroxymethyl)-piperidino, 4-(hydroxymethyl)-piperidino, 3-methoxy-piperidino, 4-(methoxymethyl)-piperidino, 4-(fluoromethyl)-piperidino, 4-(trifluoromethyl)-piperidino, 4-cyano-piperidino, 4-carbamoyl-piperidino, 4-(methylamino)-piperidino, 4-(dimethylamino)-piperidino, 4-(methylaminomethyl)-piperidino, or 4-(dimethylaminomethyl)-piperidino.

Embodiment 156

A compound according to embodiment 149, wherein $NR^hR^k$ is $NHR^k$, where $R^k$ is 2-hydroxypropyl, 2-(methylsulfonyl)-ethyl, tetrahydrofuran-3-yl, tetrahydropyran-4-yl, 1-methylpiperidin-4-yl, piperidin-3-yl, or 1-methylpiperidin-3-yl.

Embodiment 157

A compound according to embodiment 149, wherein $NR^hR^k$ is $N(CH_3)R^k$, where $R^k$ is 2-hydroxyethyl, tetrahydropyran-4-yl, pyrrolidin-3-yl, 1-methylpyrrolidin-3-yl, or piperazin-3-yl.

Embodiment 158

A compound according to embodiment 149, wherein $NR^hR^k$ is $N(CH_2CH_2OH)_2$.

Embodiment 159

A compound according to embodiment 148, wherein G is —$(CH_2)_{2-3}$—C(O)—$N(CH_3)_2$.

Embodiment 160

A compound according to embodiment 148, wherein G is —$(CH_2)_3$—C(O)-(4-methylpiperazino).

Embodiment 161

A compound according to embodiment 148, wherein G is —CH($CH_3$)—C(O)—$NR^hR^k$, where $NR^hR^k$ is methylamino, dimethylamino, 4-methylpiperazino, or morpholino.

Embodiment 162

A compound according to embodiment 148, wherein G is —C($CH_3$)$_2$—C(O)—$N(CH_3)_2$.

Embodiment 163

A compound according to embodiment 134, wherein G is —CH—[C(O)—$N(CH_3)_2$]—[$CH_2OH$], —CH—[C(O)—$N(CH_3)_2$]—[$(CH_2)_4$—$NH_2$], or —CH—[C(O)—$N(CH_3)_2$]—[$(CH_2)_4$—$N(CH_3)_2$].

Embodiment 164

A compound according to embodiment 134, wherein G is —$C_{1-8}$ alkyl substituted once by —O—$R^h$.

Embodiment 165

A compound according to embodiment 164, wherein G is —$(CH_2)_2$—O—$R^h$.

Embodiment 166

A compound according to embodiment 165, wherein $R^h$ is hydrogen, methyl, or ethyl.

Embodiment 167

A compound according to embodiment 165, wherein $R^h$ is trifluoromethyl, 2-fluoroethyl, 3-fluoropropyl, or 2,2-difluoroethyl.

Embodiment 168

A compound according to embodiment 165, wherein $R^h$ is tetrahydrofuran-2-ylmethyl.

Embodiment 169

A compound according to embodiment 165, wherein $R^h$ is 2-hydroxyethyl.

Embodiment 170

A compound according to embodiment 165, wherein $R^h$ is 3-hydroxypropyl.

Embodiment 171

A compound according to embodiment 165, wherein $R^h$ is 2-methoxyethyl.

Embodiment 172

A compound according to embodiment 165, wherein $R^h$ is 2-(2-hydroxyethoxy)-ethyl.

Embodiment 173

A compound according to embodiment 165, wherein $R^h$ is 2-hydroxypropyl or 1-hydroxyprop-2-yl.

Embodiment 174

A compound according to embodiment 165, wherein $R^h$ is 2-cyanoethyl, 2-(methylcarbonylamino)-ethyl, or 2-(methyl sulfonylamino)-ethyl.

Embodiment 175

A compound according to embodiment 165, wherein $R^h$ is 2-aminoethyl, 2-(methylamino)-ethyl, or 2-(dimethylamino)-ethyl.

Embodiment 176

A compound according to embodiment 165, wherein $R^h$ is carbamoylmethyl.

Embodiment 177

A compound according to embodiment 164, wherein G is —$(CH_2)_3$—O—$R^h$.

Embodiment 178

A compound according to embodiment 177, wherein $R^h$ is hydrogen, methyl, or ethyl.

Embodiment 179

A compound according to embodiment 177, wherein $R^h$ is 2-hydroxyethyl.

Embodiment 180

A compound according to embodiment 164, wherein G is —(CH2)$_4$—OH, —(CH2)$_5$—OH, —CH$_2$C(CH$_3$)$_2$—OH, —CH$_2$C(CH$_3$)$_2$—OCH$_3$, —CH$_2$C(CH$_3$)$_2$—CH$_2$—OH, —CH(CH$_3$)—CH$_2$—OCH$_3$, —(CH$_2$)$_3$C(CH$_3$)$_2$—CH$_2$—OH, —(CH$_2$)$_2$CH(CH$_3$)—CH$_2$—OH, or —(CH$_2$)$_2$CH(CH$_3$)—OH.

Embodiment 181

A compound according to embodiment 164, wherein G is —CH$_2$CH(CH$_3$)—O—R$^h$.

Embodiment 182

A compound according to embodiment 181, wherein $R^h$ is hydrogen, methyl, or ethyl.

Embodiment 183

A compound according to embodiment 134, wherein G is —CH$_2$—CH(OH)—CH$_2$—OH.

Embodiment 184

A compound according to embodiment 134, wherein G is —C$_{1-8}$ alkyl substituted once by —NR$^h$R$^k$.

Embodiment 185

A compound according to embodiment 184, wherein G is —(CH$_2$)$_2$—NR$^h$R$^k$.

Embodiment 186

A compound according to embodiment 185, wherein NR$^h$R$^k$ is amino, methylamino, or dimethylamino.

Embodiment 187

A compound according to embodiment 185, wherein NR$^h$R$^k$ is methylcarbonylamino.

Embodiment 188

A compound according to embodiment 185, wherein NR$^h$R$^k$ is (dimethylamino)methylcarbonylamino, hydroxymethylcarbonylamino, or 1-hydroxyethylcarbonylamino.

Embodiment 189

A compound according to embodiment 185, wherein NR$^h$R$^k$ is methylsulfonylamino.

Embodiment 190

A compound according to embodiment 185, wherein NR$^h$R$^k$ is piperidino, 4-hydroxypiperidino, or 3-hydroxypiperidino.

Embodiment 191

A compound according to embodiment 185, wherein NR$^h$R$^k$ is piperidino, 4,4-difluoropiperidino, or 3,3-difluoropiperidino.

Embodiment 192

A compound according to embodiment 185, wherein NR$^h$R$^k$ is 2-oxo-pyrrolidino, 2-oxo-imidazolidino, or 3-oxo-piperazino.

Embodiment 193

A compound according to embodiment 185, wherein NR$^h$R$^k$ is piperazino, 4-methylpiperazino, morpholino, or 1,1-dioxo-thiomorpholino.

Embodiment 194

A compound according to embodiment 184, wherein G is —(CH$_2$)$_3$—NR$^h$R$^k$.

Embodiment 195

A compound according to embodiment 194, wherein NR$^h$R$^k$ is amino, dimethylamino, or diethylamino.

Embodiment 196

A compound according to embodiment 194, wherein NR$^h$R$^k$ is piperidino, 4-methylpiperazino, or morpholino.

Embodiment 197

A compound according to embodiment 184, wherein G is —(CH$_2$)$_4$—NR$^h$R$^k$.

Embodiment 198

A compound according to embodiment 197, wherein NR$^h$R$^k$ is amino, dimethylamino, or diethylamino.

Embodiment 199

A compound according to embodiment 133, wherein G is —C$_{1-6}$ alkylene-heterocyclyl, where the alkylene and heterocyclyl groups are optionally substituted one or more times with substituents independently selected from R$^c$.

Embodiment 200

A compound according to embodiment 199, wherein G is —CH$_2$-heterocyclyl, where the heterocyclyl group is optionally substituted once with a substituent selected from R$^c$.

Embodiment 201

A compound according to embodiment 200, wherein the heterocyclyl group is tetrahydropyran-4-yl, tetrahydrofuran-2-yl, 1,4-dioxan-2-yl, morpholin-2-yl, tetrahydropyran-2-yl, piperidin-4-yl, 1-(2-hydroxyethyl)-piperidin-4-yl, 1-(dimethylaminomethylcarbonyl)-piperidin-4-yl, piperazin-2-yl, or 1-methyl-piperazin-2-yl.

Embodiment 202

A compound according to embodiment 133, wherein G is $C_{3-10}$ cycloalkyl optionally substituted one or more times with substituents independently selected from $R^c$.

Embodiment 203

A compound according to embodiment 202, wherein G is 4-hydroxy-cyclohexyl, 4-carboxy-cyclohexyl, or 4-(dimethylaminocarbonyl)-cyclohexyl.

Embodiment 204

A compound according to embodiment 202, wherein G is 1-carboxy-cyclopropyl, 1-(ethoxycarbonyl)-cyclopropyl, or 1-(dimethylamino-carbonyl)-cyclopropyl.

Embodiment 205

A compound according to embodiment 133, wherein G is $C_{1-6}$ alkylene-$C_{3-10}$ cycloalkyl, where the alkylene and cycloalkyl groups are optionally substituted one or more times with substituents independently selected from $R^c$.

Embodiment 206

A compound according to embodiment 205, wherein G is —CH$_2$-(4-hydroxy-cyclohexyl).

Embodiment 207

A compound according to embodiment 205, wherein G is —(CH$_2$)$_2$-(4-hydroxy-cyclohexyl).

Embodiment 208

A compound according to embodiment 205, wherein G is —CH$_2$-[4-(hydroxymethyl)-cyclohexyl].

Embodiment 209

A compound according to embodiment 133, wherein G is heterocyclyl optionally substituted one or more times with substituents independently selected from $R^c$.

Embodiment 210

A compound according to embodiment 209, wherein G is piperidin-4-yl, 1-methyl-piperidin-4-yl, 1-carboxy-piperidin-4-yl, 1-(methyl sulfonyl)-piperidin-4-yl, 1-(2-hydroxyethyl)-piperidin-4-yl, 1-(dimethyl-aminocarbonyl)piperidin-4-yl, or 1-(dimethylaminomethylcarbonyl)-piperidin-4-yl.

Embodiment 211

A compound according to embodiment 209, wherein G is piperidin-3-yl or 1-(dimethylaminomethylcarbonyl)-piperidin-3-yl.

Embodiment 212

A compound according to embodiment 209, wherein G is 1,1-dioxo-tetrahydrothiophen-3-yl.

Embodiment 213

A compound according to embodiment 209, wherein G is pyrrolidin-3-yl, 1-methyl-pyrrolidin-3-yl, 1-(2-hydroxyethyl)-pyrrolidin-3-yl, 1-(2-hydroxypropyl)-pyrrolidin-3-yl, 1-(2-hydroxy-2-methylpropyl)-pyrrolidin-3-yl, 1-(1-hydroxyethylcarbonyl)-pyrrolidin-3-yl, 1-(2-carboxyethyl)-pyrrolidin-3-yl, or 1-(2-methylsulfonylamino-ethyl)-pyrrolidin-3-yl.

Embodiment 214

A compound according to embodiment 134, wherein G is —$C_{1-8}$ alkyl substituted once by —S—$R^h$.

Embodiment 215

A compound according to embodiment 214, wherein G is —(CH$_2$)$_2$—S—$R^h$.

Embodiment 216

A compound according to embodiment 215, wherein $R^h$ is methyl or ethyl.

Embodiment 217

A compound according to embodiment 215, wherein $R^h$ is 2-hydroxyethyl.

Embodiment 218

A compound according to embodiment 214, wherein G is —(CH$_2$)$_3$—S—$R^h$.

Embodiment 219

A compound according to embodiment 218, wherein $R^h$ is methyl.

Embodiment 220

A compound according to embodiment 134, wherein G is —$C_{1-8}$ alkyl substituted once by —SO$_2$—$R^h$.

Embodiment 221

A compound according to embodiment 220, wherein G is —(CH$_2$)$_2$—SO$_2$—$R^h$.

Embodiment 222

A compound according to embodiment 221, wherein $R^h$ is methyl or ethyl.

Embodiment 223

A compound according to embodiment 221, wherein $R^h$ is 2-hydroxyethyl.

Embodiment 224

A compound according to embodiment 220, wherein G is —(CH$_2$)$_3$—SO$_2$—$R^h$.

Embodiment 225

A compound according to embodiment 224, wherein $R^h$ is methyl.

Embodiment 226

A compound according to embodiment 133 wherein
G is —CH(CH$_3$)—NR$^h$R$^k$, where NR$^h$R$^k$ is pyrrolidino, piperidino, 4-methyl-piperazino, morpholino, or dimethylamino.

Embodiment 227

A compound according to embodiment 133 wherein
G is 1-(2-hydroxypropyl)-pyrrolidin-3-yl or 1-(1-hydroxyethylcarbonyl)-pyrrolidin-3-yl.

Embodiment 228

A compound according to embodiment 133 wherein
G is 1-(dimethylaminomethylcarbonyl)-piperidin-4-yl.

Embodiment 229

A compound according to embodiment 133 wherein
G is —(CH$_2$)$_{3-5}$—OH.

Embodiment 230

A compound according to embodiment 133 wherein
G is 4-hydroxy-cyclohexylmethyl.

Embodiment 231

A compound according to embodiment 133 wherein
G is —(CH$_2$)$_2$—NHC(O)—CH$_2$—N(CH$_3$)$_2$.

Embodiment 232

A compound according to embodiment 133 wherein
G is 4-hydroxy-cyclohexylmethyl.

Embodiment 233

A compound according to embodiment 133 wherein
G is —CH$_2$—C(O)—NR$^h$R$^k$, where NR$^h$R$^k$ is 3-hydroxy-pyrrolidino or 3-(dimethyl-amino)-pyrrolidino.

Embodiment 234

A compound according to embodiment 133 wherein
G is —CH$_2$—C(O)—NR$^h$R$^k$, where NR$^h$R$^k$ is morpholino.

Embodiment 235

A compound according to embodiment 133 wherein
G is —CH$_2$—C(O)—NR$^h$R$^k$, where NR$^h$R$^k$ is 4-hydroxy-piperidino, 4-methoxy-piperidino, 4-(hydroxymethyl)-piperidino, 3-hydroxy-piperidino, 3-methoxy-piperidino, 3-(hydroxymethyl)-piperidino, or 4,4-difluoropiperidino.

Embodiment 236

A compound according to embodiment 133 wherein
G is —CH$_2$—C(O)—NR$^h$R$^k$, where NR$^h$R$^k$ is dimethylamino.

Embodiment 237

A compound according to embodiment 133 wherein
G is —(CH$_2$)$_2$—O—(CH$_2$)$_2$—OH.

Embodiment 238

A compound according to embodiment 133 wherein
G is —(CH$_2$)$_2$—O—(CH$_2$)$_2$—OCH$_3$.

Embodiment 239

A compound according to embodiment 133 wherein
G is —CH$_2$—CH(CH$_3$)—OH.

Embodiment 240

A compound according to any one of embodiments 66 to 112, wherein
L is C(O)NH, and G is C$_{1-8}$ alkyl substituted once by a heteroaryl group, where the heteroaryl group is optionally substituted one or more times with substituents independently selected from R$^x$.

Embodiment 241

A compound according to embodiment 240, wherein
G is —CH$_2$-(2-furyl), —CH$_2$-(2-thienyl), —CH$_2$-(2-oxazolyl), or —CH$_2$-(2-thiazolyl).

Embodiment 242

A compound according to embodiment 240, wherein
G is —(CH$_2$)$_{2-3}$-(1-pyrrolyl), —(CH$_2$)$_{2-3}$-(1-pyrazolyl), or —(CH$_2$)$_{2-3}$-(1-imidazolyl).

Embodiment 243

A compound according to any one of embodiments 66 to 112, wherein
L is C(O)NH, and G is C$_{1-8}$ alkyl substituted once by a phenyl group, where the phenyl group is optionally substituted one or more times with substituents independently selected from R$^x$.

Embodiment 244

A compound according to embodiment 243, wherein
G is —(—CH$_2$)$_{1-2}$-(4-hydroxyphenyl) or —(—CH$_2$)$_{1-2}$-(4-methoxy-3-hydroxyphenyl).

Embodiment 245

A compound according to any one of embodiments 66 to 112, wherein
L is C(O)NH, and G is —CH$_2$—C(O)NH—CH$_2$-(4-hydroxyphenyl).

Embodiment 246

A compound according to any one of embodiments 66 to 112, wherein
L is C(O)NH, and G is —CH$_2$—C(O)[4-(pyrimidin-2-yloxy)-piperidino].

Embodiment 247

A compound according to any one of embodiments 1 to 246, wherein the compound is in the form of a free acid or a free base.

Embodiment 248

A compound according to any one of embodiments 1 to 246, wherein the compound is in the form of a pharmaceutically acceptable salt.

Embodiment 249

A compound according to embodiment 1, wherein the compound is a compound from Table A or a pharmaceutically acceptable salt thereof.

In another embodiment, a Bach1 Inhibitor may be any single compound listed in Table 1 below.

TABLE A

| No. | Name |
|---|---|
| 1 | 1-Methyl-2-(6-trifluoromethoxy-benzothiazol-2-ylamino)-1H-benzoimidazole-5-carboxylic acid methyl amide |
| 2 | 1-Methyl-2-(6-trifluoromethoxy-benzothiazol-2-ylamino)-1H-benzoimidazole-5-carboxylic acid methyl ester |
| 3 | 1-Methyl-2-(6-trifluoromethoxy-benzothiazol-2-ylamino)-1H-benzoimidazole-5-carboxylic acid |
| 4 | 1-Methyl-2-(6-trifluoromethoxy-benzothiazol-2-ylamino)-1H-benzoimidazole-5-carboxylic acid (2-ethoxy-ethyl)-amide |
| 5 | 1-Methyl-2-(6-trifluoromethoxy-benzothiazol-2-ylamino)-1H-benzoimidazole-5-carboxylic acid cyclopropylmethyl-amide |
| 6 | 1-Methyl-2-(6-trifluoromethoxy-benzothiazol-2-ylamino)-1H-benzoimidazole-5-carboxylic acid ethylamide |
| 7 | [1-Methyl-2-(6-trifluoromethoxy-benzothiazol-2-ylamino)-1H-benzoimidazol-5-yl]-pyrrolidin-1-yl-methanone |
| 8 | 1-Methyl-2-(6-trifluoromethoxy-benzothiazol-2-ylamino)-1H-benzoimidazole-5-carboxylic acid (2-methoxy-ethyl)-amide |
| 9 | 1-Methyl-2-(6-trifluoromethoxy-benzothiazol-2-ylamino)-1H-benzoimidazole-5-carboxylic acid (2-fluoro-ethyl)-amide |
| 10 | 1-Methyl-2-(6-trifluoromethoxy-benzothiazol-2-ylamino)-1H-benzoimidazole-5-carboxylic acid (2-hydroxy-ethyl)-amide |
| 11 | 1-Methyl-2-(6-trifluoromethoxy-benzothiazol-2-ylamino)-1H-benzoimidazole-5-carboxylic acid (3-pyrazol-1-yl-propyl)-amide |
| 12 | 1-Methyl-2-(6-trifluoromethoxy-benzothiazol-2-ylamino)-1H-benzoimidazole-5-carboxylic acid propylamide |
| 13 | 1-Methyl-2-(6-trifluoromethoxy-benzothiazol-2-ylamino)-1H-benzoimidazole-5-carboxylic acid (3-hydroxy-propyl)-amide |
| 14 | 1-Methyl-2-(6-trifluoromethoxy-benzothiazol-2-ylamino)-1H-benzoimidazole-5-carboxylic acid (3-ethoxy-propyl)-amide |
| 15 | 1-Methyl-2-(6-trifluoromethoxy-benzothiazol-2-ylamino)-1H-benzoimidazole-5-carboxylic acid morpholin-4-ylamide |
| 16 | 1-Methyl-2-(6-trifluoromethoxy-benzothiazol-2-ylamino)-1H-benzoimidazole-5-carboxylic acid (2,2,2-trifluoro-ethyl)-amide |
| 17 | 1-Methyl-2-(6-trifluoromethoxy-benzothiazol-2-ylamino)-1H-benzoimidazole-5-carboxylic acid (tetrahydro-pyran-4-ylmethyl)-amide |
| 18 | 1-Methyl-2-(6-trifluoromethoxy-benzothiazol-2-ylamino)-1H-benzoimidazole-5-carboxylic acid (tetrahydro-furan-2-ylmethyl)-amide |
| 19 | 1-Methyl-2-(6-trifluoromethoxy-benzothiazol-2-ylamino)-1H-benzoimidazole-5-carboxylic acid (3-methoxy-propyl)-amide |
| 20 | 1-Methyl-2-(6-trifluoromethoxy-benzothiazol-2-ylamino)-1H-benzoimidazole-5-carboxylic acid (2-methoxy-1-methyl-ethyl)-amide |
| 21 | 1-Methyl-2-(6-trifluoromethoxy-benzothiazol-2-ylamino)-1H-benzoimidazole-5-carboxylic acid (2-hydroxy-propyl)-amide |
| 22 | 1-Methyl-2-(6-trifluoromethoxy-benzothiazol-2-ylamino)-1H-benzoimidazole-5-carboxylic acid (2-methoxy-2-methyl-propyl)-amide |
| 23 | 1-Methyl-2-(6-trifluoromethyl-benzothiazol-2-ylamino)-1H-benzoimidazole-5-carboxylic acid methyl ester |
| 24 | 1-Methyl-2-(6-trifluoromethyl-benzothiazol-2-ylamino)-1H-benzoimidazole-5-carboxylic acid |
| 25 | 1-Methyl-2-(6-trifluoromethyl-benzothiazol-2-ylamino)-1H-benzoimidazole-5-carboxylic acid (2-methoxy-ethyl)-amide |
| 26 | 1-Methyl-2-(6-trifluoromethyl-benzothiazol-2-ylamino)-1H-benzoimidazole-5-carboxylic acid ethylamide |
| 27 | 1-Methyl-2-(6-trifluoromethyl-benzothiazol-2-ylamino)-1H-benzoimidazole-5-carboxylic acid (2-hydroxy-ethyl)-amide |
| 28 | 2-(6-Chloro-benzothiazol-2-ylamino)-1-methyl-1H-benzoimidazole-5-carboxylic acid methyl ester |
| 29 | 2-(6-Chloro-benzothiazol-2-ylamino)-1-methyl-1H-benzoimidazole-5-carboxylic acid |
| 30 | 2-(6-Chloro-benzothiazol-2-ylamino)-1-methyl-1H-benzoimidazole-5-carboxylic acid (2-hydroxy-ethyl)-amide |
| 31 | 2-(6-Chloro-benzothiazol-2-ylamino)-1-methyl-1H-benzoimidazole-5-carboxylic acid (2-methoxy-ethyl)-amide |

TABLE A-continued

| No. | Name |
|---|---|
| 32 | 2-(6-Chloro-benzothiazol-2-ylamino)-1-methyl-1H-benzoimidazole-5-carboxylic acid ethylamide |
| 33 | 2-(5,6-Difluoro-benzothiazol-2-ylamino)-1-methyl-1H-benzoimidazole-5-carboxylic acid methyl ester |
| 34 | 2-(5,6-Difluoro-benzothiazol-2-ylamino)-1-methyl-1H-benzoimidazole-5-carboxylic acid |
| 35 | 2-(5,6-Difluoro-benzothiazol-2-ylamino)-1-methyl-1H-benzoimidazole-5-carboxylic acid ethylamide |
| 36 | 2-(5,6-Difluoro-benzothiazol-2-ylamino)-1-methyl-1H-benzoimidazole-5-carboxylic acid (2-hydroxy-ethyl)-amide |
| 37 | 2-(5,6-Difluoro-benzothiazol-2-ylamino)-1-methyl-1H-benzoimidazole-5-carboxylic acid (2-methoxy-ethyl)-amide |
| 38 | 3-Methyl-2-(6-trifluoromethoxy-benzothiazol-2-ylamino)-3H-benzoimidazole-5-carboxylic acid methylamide |
| 39 | 6-Fluoro-1-methyl-2-(6-trifluoromethoxy-benzothiazol-2-ylamino)-1H-benzoimidazole-5-carboxylic acid (2-methoxy-ethyl)-amide |
| 40 | 6-Fluoro-1-methyl-2-(6-trifluoromethoxy-benzothiazol-2-ylamino)-1H-benzoimidazole-5-carboxylic acid methyl ester |
| 41 | 6-Fluoro-1-methyl-2-(6-trifluoromethoxy-benzothiazol-2-ylamino)-1H-benzoimidazole-5-carboxylic acid |
| 42 | 6-Fluoro-1-methyl-2-(6-trifluoromethoxy-benzothiazol-2-ylamino)-1H-benzoimidazole-5-carboxylic acid ethylamide |
| 43 | 1-Methyl-2-(6-trifluoromethoxy-benzothiazol-2-ylamino)-1H-benzoimidazole-5-carboxylic acid (2-morpholin-4-yl-ethyl)-amide |
| 44 | 1-Methyl-2-(6-trifluoromethoxy-benzothiazol-2-ylamino)-1H-benzoimidazole-5-carboxylic acid (2-trifluoromethoxy-ethyl)-amide |
| 45 | 1-Methyl-2-(6-trifluoromethoxy-benzothiazol-2-ylamino)-1H-benzoimidazole-5-carboxylic acid (2-hydroxy-2-methyl-propyl)-amide |
| 46 | 1-Methyl-2-(6-trifluoromethoxy-benzothiazol-2-ylamino)-1H-benzoimidazole-5-carboxylic acid [2-(2-hydroxy-ethoxy)-ethyl]-amide |
| 47 | 1-Methyl-2-(6-trifluoromethoxy-benzothiazol-2-ylamino)-1H-benzoimidazole-5-carboxylic acid [2-(2-fluoro-ethoxy)-ethyl]-amide |
| 48 | 1-Methyl-2-(6-trifluoromethoxy-benzothiazol-2-ylamino)-1H-benzoimidazole-5-carboxylic acid (furan-2-ylmethyl)-amide |
| 49 | 1-Methyl-2-(6-trifluoromethoxy-benzothiazol-2-ylamino)-1H-benzoimidazole-5-carboxylic acid ([1,4]dioxan-2-ylmethyl)-amide |
| 50 | 1-Methyl-2-(6-trifluoromethoxy-benzothiazol-2-ylamino)-1H-benzoimidazole-5-carboxylic acid ((S)-2-hydroxy-propyl)-amide |
| 51 | 1-Methyl-2-(6-trifluoromethoxy-benzothiazol-2-ylamino)-1H-benzoimidazole-5-carboxylic acid ((R)-2-hydroxy-propyl)-amide |
| 52 | 1-Methyl-2-(6-trifluoromethoxy-benzothiazol-2-ylamino)-1H-benzoimidazole-5-carboxylic acid (trans-4-hydroxy-cyclohexyl)-amide |
| 53 | 1-Methyl-2-(6-trifluoromethoxy-benzothiazol-2-ylamino)-1H-benzoimidazole-5-carboxylic acid [2-(tetrahydro-furan-2-ylmethoxy)-ethyl]-amide |
| 54 | 1-Methyl-2-(6-trifluoromethoxy-benzothiazol-2-ylamino)-1H-benzoimidazole-5-carboxylic acid (2-ethoxy-propyl)-amide |
| 55 | 2-({[1-Methyl-2-(6-trifluoromethoxy-benzothiazol-2-ylamino)-1H-benzoimidazole-5-carbonyl]-amino}-methyl)-morpholine-4-carboxylic acid tert-butyl ester |
| 56 | 1-Methyl-2-(6-trifluoromethoxy-benzothiazol-2-ylamino)-1H-benzoimidazole-5-carboxylic acid (morpholin-2-ylmethyl)-amide hydrochloride |
| 57 | 6-Fluoro-1-methyl-2-(6-trifluoromethoxy-benzothiazol-2-ylamino)-1H-benzoimidazole-5-carboxylic acid (2-ethoxy-ethyl)-amide |
| 58 | 6-Fluoro-1-methyl-2-(6-trifluoromethoxy-benzothiazol-2-ylamino)-1H-benzoimidazole-5-carboxylic acid dimethylcarbamoylmethyl-amide |
| 59 | 6-Fluoro-1-methyl-2-(6-trifluoromethoxy-benzothiazol-2-ylamino)-1H-benzoimidazole-5-carboxylic acid (2-morpholin-4-yl-ethyl)-amide |
| 60 | 6-Fluoro-1-methyl-2-(6-trifluoromethoxy-benzothiazol-2-ylamino)-1H-benzoimidazole-5-carboxylic acid (2-hydroxy-propyl)-amide |
| 61 | 6-Methoxy-1-methyl-2-(6-trifluoromethoxy-benzothiazol-2-ylamino)-1H-benzoimidazole-5-carboxylic acid methyl ester |
| 62 | 6-Methoxy-1-methyl-2-(6-trifluoromethoxy-benzothiazol-2-ylamino)-1H-benzoimidazole-5-carboxylic acid |
| 63 | 6-Methoxy-1-methyl-2-(6-trifluoromethoxy-benzothiazol-2-ylamino)-1H-benzoimidazole-5-carboxylic acid dimethylcarbamoyl-methyl-amide |
| 64 | 6-Methoxy-1-methyl-2-(6-trifluoromethoxy-benzothiazol-2-ylamino)-1H-benzoimidazole-5-carboxylic acid ethylamide |
| 65 | 6-Methoxy-1-methyl-2-(6-trifluoromethoxy-benzothiazol-2-ylamino)-1H-benzoimidazole-5-carboxylic acid (2-ethoxy-ethyl)-amide |
| 66 | 6-Methoxy-1-methyl-2-(6-trifluoromethoxy-benzothiazol-2-ylamino)-1H-benzoimidazole-5-carboxylic acid (2-morpholin-4-yl-ethyl)-amide |
| 67 | 6-Methoxy-1-methyl-2-(6-trifluoromethoxy-benzothiazol-2-ylamino)-1H-benzoimidazole-5-carboxylic acid (2-methoxy-ethyl)-amide |
| 68 | 6-Methoxy-1-methyl-2-(6-trifluoromethoxy-benzothiazol-2-ylamino)-1H-benzoimidazole-5-carboxylic acid (2-hydroxy-propyl)-amide |
| 69 | 6-Diethylamino-1-methyl-2-(6-trifluoromethoxy-benzothiazol-2-ylamino)-1H-benzoimidazole-5-carboxylic acid methyl ester |
| 70 | 6-Diethylamino-1-methyl-2-(6-trifluoromethoxy-benzothiazol-2-ylamino)-1H-benzoimidazole-5-carboxylic acid |

TABLE A-continued

| No. | Name |
|---|---|
| 71 | 3-Methyl-2-(6-trifluoromethoxy-benzothiazol-2-ylamino)-3H-imidazo[4,5-b]pyridine-6-carboxylic acid ethyl ester |
| 72 | 3-Methyl-2-(6-trifluoromethoxy-benzothiazol-2-ylamino)-3H-imidazo[4,5-b]pyridine-6-carboxylic acid |
| 73 | 3-Methyl-2-(6-trifluoromethoxy-benzothiazol-2-ylamino)-3H-imidazo[4,5-b]pyridine-6-carboxylic acid (2-methoxy-ethyl)-amide |
| 74 | 3-Methyl-2-(6-trifluoromethoxy-benzothiazol-2-ylamino)-3H-imidazo[4,5-b]pyridine-6-carboxylic acid dimethylcarbamoylmethyl-amide |
| 75 | 3-Methyl-2-(6-trifluoromethoxy-benzothiazol-2-ylamino)-3H-imidazo[4,5-b]pyridine-6-carboxylic acid (2-ethoxy-ethyl)-amide |
| 76 | 3-Methyl-2-(6-trifluoromethoxy-benzothiazol-2-ylamino)-3H-imidazo[4,5-b]pyridine-6-carboxylic acid ethylamide |
| 77 | 3-Methyl-2-(6-trifluoromethoxy-benzothiazol-2-ylamino)-3H-imidazo[4,5-b]pyridine-6-carboxylic acid (2-morpholin-4-yl-ethyl)-amide |
| 78 | 3-Methyl-2-(6-trifluoromethoxy-benzothiazol-2-ylamino)-3H-imidazo[4,5-b]pyridine-6-carboxylic acid (2-hydroxy-propyl)-amide |
| 79 | {[1-Methyl-2-(6-trifluoromethoxy-benzothiazol-2-ylamino)-1H-benzoimidazole-5-carbonyl]-amino}-acetic acid methyl ester |
| 80 | 1-Methyl-2-(6-trifluoromethoxy-benzothiazol-2-ylamino)-1H-benzoimidazole-5-carboxylic acid dimethylcarbamoylmethyl-amide |
| 81 | 1-Methyl-2-(6-trifluoromethoxy-benzothiazol-2-ylamino)-1H-benzoimidazole-5-carboxylic acid ((S)-1-ethylcarbamoyl-ethyl)-amide |
| 82 | 1-Methyl-2-(6-trifluoromethoxy-benzothiazol-2-ylamino)-1H-benzoimidazole-5-carboxylic acid (2-dimethylamino-ethyl)-amide |
| 83 | {[1-Methyl-2-(6-trifluoromethoxy-benzothiazol-2-ylamino)-1H-benzoimidazole-5-carbonyl]-amino}-acetic acid |
| 84 | 1-Methyl-2-(6-trifluoromethyl-benzothiazol-2-ylamino)-1H-benzoimidazole-5-carboxylic acid methylamide |
| 85 | 1-Methyl-2-(6-trifluoromethyl-benzothiazol-2-ylamino)-1H-benzoimidazole-5-carboxylic acid (2-ethoxy-ethyl)-amide |
| 86 | 2-(5,6-Difluoro-benzothiazol-2-ylamino)-1-methyl-1H-benzoimidazole-5-carboxylic acid methylamide |
| 87 | 2-(5,6-Difluoro-benzothiazol-2-ylamino)-1-methyl-1H-benzoimidazole-5-carboxylic acid (2-ethoxy-ethyl)-amide |
| 88 | 2-(6-Chloro-benzothiazol-2-ylamino)-1-methyl-1H-benzoimidazole-5-carboxylic acid methylamide |
| 89 | 2-(6-Chloro-benzothiazol-2-ylamino)-1-methyl-1H-benzoimidazole-5-carboxylic acid (2-ethoxy-ethyl)-amide |
| 90 | 1-Methyl-2-(6-trifluoromethoxy-benzothiazol-2-ylamino)-1H-benzoimidazole-5-carboxylic acid (1-methanesulfonyl-piperidin-4-yl)-amide |
| 91 | {[1-Methyl-2-(6-trifluoromethoxy-benzothiazol-2-ylamino)-1H-benzoimidazole-5-carbonyl]-amino}-acetic acid tert-butyl ester |
| 92 | 4-{[1-Methyl-2-(6-trifluoromethoxy-benzothiazol-2-ylamino)-1H-benzoimidazole-5-carbonyl]-amino}-piperidine-1-carboxylic acid tert-butyl ester |
| 93 | 1-Methyl-2-(6-trifluoromethoxy-benzothiazol-2-ylamino)-1H-benzoimidazole-5-carboxylic acid piperidin-4-ylamide hydrochloride |
| 94 | 3-{[1-Methyl-2-(6-trifluoromethoxy-benzothiazol-2-ylamino)-1H-benzoimidazole-5-carbonyl]-amino}-piperidine-1-carboxylic acid tert-butyl ester |
| 95 | 1-Methyl-2-(6-trifluoromethoxy-benzothiazol-2-ylamino)-1H-benzoimidazole-5-carboxylic acid piperidin-3-ylamide hydrochloride |
| 96 | 1-Methyl-2-(6-trifluoromethoxy-benzothiazol-2-ylamino)-1H-benzoimidazole-5-carboxylic acid (thiazol-2-ylmethyl)-amide |
| 97 | 3-{[1-Methyl-2-(6-trifluoromethoxy-benzothiazol-2-ylamino)-1H-benzoimidazole-5-carbonyl]-amino}-propionic acid methyl ester |
| 98 | 3-{[2-(6-Trifluoromethoxy-benzothiazol-2-ylamino)-1-methyl-1H-benzimidazole-5-carbonyl]-amino}-propionic acid |
| 99 | 1-Methyl-2-(5-trifluoromethoxy-benzothiazol-2-ylamino)-1H-benzoimidazole-5-carboxylic acid methyl ester |
| 100 | 1-Methyl-2-(6-trifluoromethoxy-benzothiazol-2-ylamino)-1H-benzoimidazole-5-carboxylic acid (2-acetylamino-ethyl)-amide |
| 101 | 1-Methyl-2-(6-trifluoromethoxy-benzothiazol-2-ylamino)-1H-benzoimidazole-5-carboxylic acid (2-methylsulfanyl-ethyl)-amide |
| 102 | 1-Methyl-2-(6-trifluoromethoxy-benzothiazol-2-ylamino)-1H-benzoimidazole-5-carboxylic acid (2-methanesulfonyl-ethyl)-amide |
| 103 | (2-{[1-Methyl-2-(6-trifluoromethoxy-benzothiazol-2-ylamino)-1H-benzoimidazole-5-carbonyl]-amino}-ethyl)-carbamic acid tert-butyl ester |
| 104 | 1-Methyl-2-(6-trifluoromethoxy-benzothiazol-2-ylamino)-1H-benzoimidazole-5-carboxylic acid (2-amino-ethyl)-amide hydrochloride |
| 105 | 1-Methyl-2-(6-trifluoromethoxy-benzothiazol-2-ylamino)-1H-benzoimidazole-5-carboxylic acid (2-methylamino-ethyl)-amide |
| 106 | 1-Methyl-2-(6-trifluoromethoxy-benzothiazol-2-ylamino)-1H-benzimidazole-5-carboxylic acid trimethylhydrazide |
| 107 | 1-Methyl-2-(6-trifluoromethoxy-benzothiazol-2-ylamino)-1H-benzoimidazole-5-carboxylic acid (2-ethylsulfanyl-ethyl)-amide |
| 108 | 1-Methyl-2-(6-trifluoromethoxy-benzothiazol-2-ylamino)-1H-benzoimidazole-5-carboxylic acid (3-methylsulfanyl-propyl)-amide |
| 109 | 1-Methyl-2-(6-trifluoromethoxy-benzothiazol-2-ylamino)-1H-benzimidazole-5-carboxylic acid (2-ethanesulfonyl-ethyl)-amide |

TABLE A-continued

| No. | Name |
|---|---|
| 110 | 1-Methyl-2-(6-trifluoromethoxy-benzothiazol-2-ylamino)-1H-benzimidazole-5-carboxylic acid (3-methanesulfonyl-propyl)-amide |
| 111 | 2-(5-Fluoro-benzothiazol-2-ylamino)-1-methyl-1H-benzoimidazole-5-carboxylic acid methyl ester |
| 112 | 2-(6-Fluoro-benzothiazol-2-ylamino)-1-methyl-1H-benzoimidazole-5-carboxylic acid methyl ester |
| 113 | 2-(6-Methanesulfonyl-benzothiazol-2-ylamino)-1-methyl-1H-benzoimidazole-5-carboxylic acid methyl ester |
| 114 | 1-Methyl-2-(6-methyl-benzothiazol-2-ylamino)-1H-benzoimidazole-5-carboxylic acid methyl ester |
| 115 | 1-Methyl-2-(5-trifluoromethoxy-benzothiazol-2-ylamino)-1H-benzimidazole-5-carboxylic acid methylamide |
| 116 | 1-Methyl-2-(5-trifluoromethoxy-benzothiazol-2-ylamino)-1H-benzimidazole-5-carboxylic acid (2-methoxy-ethyl)-amide |
| 117 | 2-(5-Fluoro-benzothiazol-2-ylamino)-1-methyl-1H-benzimidazole-5-carboxylic acid |
| 118 | 2-(6-Fluoro-benzothiazol-2-ylamino)-1-methyl-1H-benzimidazole-5-carboxylic acid |
| 119 | 2-(6-Methanesulfonyl-benzothiazol-2-ylamino)-1-methyl-1H-benzimidazole-5-carboxylic acid |
| 120 | 1-Methyl-2-(6-methyl-benzothiazol-2-ylamino)-1H-benzimidazole-5-carboxylic acid |
| 121 | 1-Methyl-2-(6-trifluoromethoxy-benzothiazol-2-ylamino)-1H-benzimidazole-5-carboxylic acid (1,1-dioxo-tetrahydro-1$\lambda^6$-thiophen-3-yl)-amide |
| 122 | 2-(5-Fluoro-benzothiazol-2-ylamino)-1-methyl-1H-benzimidazole-5-carboxylic acid methylamide |
| 123 | 2-(5-Fluoro-benzothiazol-2-ylamino)-1-methyl-1H-benzimidazole-5-carboxylic acid (2-methoxy-ethyl)-amide |
| 124 | 2-(6-Fluoro-benzothiazol-2-ylamino)-1-methyl-1H-benzimidazole-5-carboxylic acid methylamide |
| 125 | 2-(6-Fluoro-benzothiazol-2-ylamino)-1-methyl-1H-benzimidazole-5-carboxylic acid (2-methoxy-ethyl)-amide |
| 126 | 2-(6-Methanesulfonyl-benzothiazol-2-ylamino)-1-methyl-1H-benzimidazole-5-carboxylic acid methylamide |
| 127 | 2-(6-Methanesulfonyl-benzothiazol-2-ylamino)-1-methyl-1H-benzimidazole-5-carboxylic acid (2-methoxy-ethyl)-amide |
| 128 | 2-(6-Methyl-benzothiazol-2-ylamino)-1-methyl-1H-benzimidazole-5-carboxylic acid methylamide |
| 129 | 2-(6-Methyl-benzothiazol-2-ylamino)-1-methyl-1H-benzimidazole-5-carboxylic acid (2-methoxy-ethyl)-amide |
| 130 | 2-(6-Methanesulfonyl-benzothiazol-2-ylamino)-1-methyl-1H-benzimidazole-5-carboxylic acid (2-methylsulfanyl-ethyl)-amide |
| 131 | 2-(6-Methanesulfonyl-benzothiazol-2-ylamino)-1-methyl-1H-benzimidazole-5-carboxylic acid (2-methylsulfonyl-ethyl)-amide |
| 132 | 1-Methyl-2-(6-trifluoromethylsulfanyl-benzothiazol-2-ylamino)-1H-benzoimidazole-5-carboxylic acid methyl ester |
| 133 | 2-(6-Chloro-benzothiazol-2-ylamino)-1-methyl-1H-benzimidazole-5-carboxylic acid dimethylcarbamoylmethyl-amide |
| 134 | 1-Methyl-2-(6-trifluoromethyl-benzothiazol-2-ylamino)-1H-benzimidazole-5-carboxylic acid dimethylcarbamoylmethyl-amide |
| 135 | 1-Methyl-2-(6-trifluoromethoxy-benzothiazol-2-ylamino)-1H-benzimidazole-5-carboxylic acid (2-dimethylcarbamoyl-ethyl)-amide |
| 136 | 3-{[1-Methyl-2-(6-trifluoromethoxy-benzothiazol-2-ylamino)-1H-benzimidazole-5-carbonyl]-amino}-propionic acid tert-butyl ester |
| 137 | 1-Methyl-2-(6-trifluoromethoxy-benzothiazol-2-ylamino)-1H-benzimidazole-5-carboxylic acid [2-(4-methyl-piperazin-1-yl)-2-oxo-ethyl]-amide |
| 138 | 1-Methyl-2-(6-trifluoromethoxy-benzothiazol-2-ylamino)-1H-benzimidazole-5-carboxylic acid (2-morpholin-4-yl-2-oxo-ethyl)-amide |
| 139 | 1-Methyl-2-(6-trifluoromethoxy-benzothiazol-2-ylamino)-1H-benzimidazole-5-carboxylic acid methylcarbamoylmethyl-amide |
| 140 | 1-Methyl-2-(6-trifluoromethoxy-benzothiazol-2-ylamino)-1H-benzimidazole-5-carboxylic acid diethylcarbamoylmethyl-amide |
| 141 | 1-Methyl-2-(6-trifluoromethoxy-benzothiazol-2-ylamino)-1H-benzimidazole-5-carboxylic acid (2-oxo-2-pyrrolidin-1-yl-ethyl)-amide |
| 142 | 4-(2-{[1-Methyl-2-(6-trifluoromethoxy-benzothiazol-2-ylamino)-1H-benzimidazole-5-carbonyl]-amino}-acetyl)-piperazine-1-carboxylic acid tert-butyl ester |
| 143 | (S)-2-{[1-Methyl-2-(6-trifluoromethoxy-benzothiazol-2-ylamino)-1H-benzoimidazole-5-carbonyl]-amino}-propionic acid methyl ester |
| 144 | 1-{[1-Methyl-2-(6-trifluoromethoxy-benzothiazol-2-ylamino)-1H-benzimidazole-5-carbonyl]-amino}-cyclopropanecarboxylic acid ethyl ester |
| 145 | 2-Methyl-2-{[1-methyl-2-(6-trifluoromethoxy-benzothiazol-2-ylamino)-1H-benzimidazole-5-carbonyl]-amino}-propionic acid methyl ester |
| 146 | (S)-2-{[1-Methyl-2-(6-trifluoromethoxy-benzothiazol-2-ylamino)-1H-benzoimidazole-5-carbonyl]-amino}-propionic acid |
| 147 | 1-{[1-Methyl-2-(6-trifluoromethoxy-benzothiazol-2-ylamino)-1H-benzimidazole-5-carbonyl]-amino}-cyclopropanecarboxylic acid |
| 148 | 2-Methyl-2-{[1-methyl-2-(6-trifluoromethoxy-benzothiazol-2-ylamino)-1H-benzimidazole-5-carbonyl]-amino}-propionic acid |
| 149 | 1-Methyl-2-(6-trifluoromethoxy-benzothiazol-2-ylamino)-1H-benzoimidazole-5-carboxylic acid ((S)-1-dimethylcarbamoyl-ethyl)-amide |

TABLE A-continued

| No. | Name |
|---|---|
| 150 | 1-Methyl-2-(6-trifluoromethoxy-benzothiazol-2-ylamino)-1H-benzimidazole-5-carboxylic acid (1-dimethylcarbamoyl-cyclopropyl)-amide |
| 151 | 1-Methyl-2-(6-trifluoromethoxy-benzothiazol-2-ylamino)-1H-benzimidazole-5-carboxylic acid (1-dimethylcarbamoyl-1-methyl-ethyl)-amide |
| 152 | 1-Methyl-2-(6-trifluoromethoxy-benzothiazol-2-ylamino)-1H-benzimidazole-5-carboxylic acid (2-oxo-2-piperazin-1-yl-ethyl)-amide hydrochloride |
| 153 | 1-Ethyl-2-(6-trifluoromethoxy-benzothiazol-2-ylamino)-1H-benzoimidazole-5-carboxylic acid methyl ester |
| 154 | 1-Ethyl-2-(6-trifluoromethoxy-benzothiazol-2-ylamino)-1H-benzoimidazole-5-carboxylic acid |
| 155 | 1-Ethyl-2-(6-trifluoromethoxy-benzothiazol-2-ylamino)-1H-benzoimidazole-5-carboxylic acid methylamide |
| 156 | 1-Ethyl-2-(6-trifluoromethoxy-benzothiazol-2-ylamino)-1H-benzoimidazole-5-carboxylic acid ethylamide |
| 157 | 1-Ethyl-2-(6-trifluoromethoxy-benzothiazol-2-ylamino)-1H-benzoimidazole-5-carboxylic acid (2-ethoxy-ethyl)-amide |
| 158 | 1-Isopropyl-2-(6-trifluoromethoxy-benzothiazol-2-ylamino)-1H benzoimidazole-5-carboxylic acid methyl ester |
| 159 | 1-Isopropyl-2-(6-trifluoromethoxy-benzothiazol-2-ylamino)-1H-benzoimidazole-5-carboxylic acid |
| 160 | 1-Isopropyl-2-(6-trifluoromethoxy-benzothiazol-2-ylamino)-1H-benzoimidazole-5-carboxylic acid methylamide |
| 161 | 1-Isopropyl-2-(6-trifluoromethoxy-benzothiazol-2-ylamino)-1H-benzoimidazole-5-carboxylic acid ethylamide |
| 162 | 1-Isobutyl-2-(6-trifluoromethoxy-benzothiazol-2-ylamino)-1H-benzoimidazole-5-carboxylic acid methyl ester |
| 163 | 1-Isobutyl-2-(6-trifluoromethoxy-benzothiazol-2-ylamino)-1H-benzoimidazole-5-carboxylic acid |
| 164 | 1-Isobutyl-2-(6-trifluoromethoxy-benzothiazol-2-ylamino)-1H-benzoimidazole-5-carboxylic acid methylamide |
| 165 | 1-Isobutyl-2-(6-trifluoromethoxy-benzothiazol-2-ylamino)-1H-benzoimidazole-5-carboxylic acid ethylamide |
| 166 | 1-(2-Methoxy-ethyl)-2-(6-trifluoromethoxy-benzothiazol-2-ylamino)-1H-benzoimidazole-5-carboxylic acid |
| 167 | 1-(2-Methoxy-ethyl)-2-(6-trifluoromethoxy-benzothiazol-2-ylamino)-1H-benzoimidazole-5-carboxylic acid methylamide |
| 168 | 1-(2-Methoxy-ethyl)-2-(6-trifluoromethoxy-benzothiazol-2-ylamino)-1H-benzoimidazole-5-carboxylic acid (2-methoxy-ethyl)-amide |
| 169 | 1-(2-Methoxy-ethyl)-2-(6-trifluoromethoxy-benzothiazol-2-ylamino)-1H-benzoimidazole-5-carboxylic acid (2-ethoxy-ethyl)-amide |
| 170 | 1-(2-Fluoro-ethyl)-2-(6-trifluoromethoxy-benzothiazol-2-ylamino)-1H-benzoimidazole-5-carboxylic acid methylamide |
| 171 | 1-(2-Fluoro-ethyl)-2-(6-trifluoromethoxy-benzothiazol-2-ylamino)-1H-benzoimidazole-5-carboxylic acid (2-methoxy-ethyl)-amide |
| 172 | 1-(2-Fluoro-ethyl)-2-(6-trifluoromethoxy-benzothiazol-2-ylamino)-1H-benzoimidazole-5-carboxylic acid (2-ethoxy-ethyl)-amide |
| 173 | 1-(2-Amino-ethyl)-2-(6-trifluoromethoxy-benzothiazol-2-ylamino)-1H-benzoimidazole-5-carboxylic acid methylamide hydrochloride |
| 174 | 2-(6-Chloro-benzothiazol-2-ylamino)-1-ethyl-1H-benzoimidazole-5-carboxylic acid methylamide |
| 175 | 2-(6-Chloro-benzothiazol-2-ylamino)-1-ethyl-1H-benzoimidazole-5-carboxylic acid ethylamide |
| 176 | 2-(6-Chloro-benzothiazol-2-ylamino)-1-ethyl-1H-benzoimidazole-5-carboxylic acid (2-fluoro-ethyl)-amide |
| 177 | 2-(6-Chloro-benzothiazol-2-ylamino)-1-ethyl-1H-benzoimidazole-5-carboxylic acid (2-methoxy-ethyl)-amide |
| 178 | 2-(6-Chloro-benzothiazol-2-ylamino)-1-ethyl-1H-benzoimidazole-5-carboxylic acid (2-methoxy-2-methyl-propyl)-amide |
| 179 | 2-(6-Chloro-benzothiazol-2-ylamino)-1-ethyl-1H-benzoimidazole-5-carboxylic acid (2-ethoxy-ethyl)-amide |
| 180 | 1-Ethyl-2-(6-trifluoromethyl-benzothiazol-2-ylamino)-1H-benzoimidazole-5-carboxylic acid methylamide |
| 181 | 1-Ethyl-2-(6-trifluoromethyl-benzothiazol-2-ylamino)-1H-benzoimidazole-5-carboxylic acid ethylamide |
| 182 | 1-Ethyl-2-(6-trifluoromethyl-benzothiazol-2-ylamino)-1H-benzoimidazole-5-carboxylic acid (2-methoxy-ethyl)-amide |
| 183 | 1-Ethyl-2-(6-trifluoromethyl-benzothiazol-2-ylamino)-1H-benzoimidazole-5-carboxylic acid (2-ethoxy-ethyl)-amide |
| 184 | 1-Ethyl-2-(6-trifluoromethyl-benzothiazol-2-ylamino)-1H-benzoimidazole-5-carboxylic acid (2-methoxy-2-methyl-propyl)-amide |
| 185 | 1-Ethyl-2-(6-trifluoromethyl-benzothiazol-2-ylamino)-1H-benzoimidazole-5-carboxylic acid (2-methylsulfanyl-ethyl)-amide |
| 186 | 1-Ethyl-2-(6-trifluoromethoxy-benzothiazol-2-ylamino)-1H-benzoimidazole-5-carboxylic acid dimethylcarbamoylmethyl-amide |
| 187 | 1-Ethyl-2-(6-trifluoromethyl-benzothiazol-2-ylamino)-1H-benzoimidazole-5-carboxylic acid dimethylcarbamoylmethyl-amide |
| 188 | 1-(2-Methoxy-ethyl)-2-(6-trifluoromethoxy-benzothiazol-2-ylamino)-1H-benzoimidazole-5-carboxylic acid dimethylcarbamoylmethyl-amide |

TABLE A-continued

| No. | Name |
|---|---|
| 189 | 1-(2-Methoxy-ethyl)-2-(6-trifluoromethoxy-benzothiazol-2-ylamino)-1H-benzoimidazole-5-carboxylic acid [2-(4-methyl-piperazin-1-yl)-2-oxo-ethyl]-amide |
| 190 | 1-Ethyl-2-(6-trifluoromethoxy-benzothiazol-2-ylamino)-1H-benzoimidazole-5-carboxylic acid [2-(4-methyl-piperazin-1-yl)-2-oxo-ethyl]-amide |
| 191 | 1-Ethyl-2-[6-(pyridin-3-yloxy)-benzothiazol-2-ylamino]-1H-benzoimidazole-5-carboxylic acid (2-methoxy-ethyl)-amide |
| 192 | 1-Methyl-2-(6-trifluoromethoxy-benzothiazol-2-ylamino)-1H-benzoimidazole-5-carboxylic acid [2-(4-hydroxy-piperidin-1-yl)-ethyl]-amide |
| 193 | 1-Methyl-2-(6-trifluoromethoxy-benzothiazol-2-ylamino)-1H-benzoimidazole-5-carboxylic acid [2-(3-hydroxy-piperidin-1-yl)-ethyl]-amide |
| 194 | 1-Methyl-2-(6-trifluoromethoxy-benzothiazol-2-ylamino)-1H-benzoimidazole-5-carbonitrile |
| 195 | 1-Methyl-2-(6-trifluoromethoxy-benzothiazol-2-ylamino)-1H-benzoimidazole-6-carbonitrile |
| 196 | [5-(1H-Imidazol-2-yl)-1-methyl-1H-benzimidazol-2-yl]-(6-trifluoromethoxy-benzothiazol-2-yl)-amine |
| 197 | [1-Methyl-6-(1H-1,2,4-triazol-3-yl)-1H-benzimidazol-2-yl]-(6-trifluoromethoxy-benzothiazol-2-yl)-amine |
| 198 | [1-Methyl-6-(5-methyl-1H-1,2,4-triazol-3-yl)-1H-benzimidazol-2-yl]-(5-trifluoromethoxy-benzothiazol-2-yl)-amine |
| 199 | (1-Ethyl-5-trifluoromethanesulfonyl-1H-benzoimidazol-2-yl)-(6-trifluoromethoxy-benzothiazol-2-yl)-amine |
| 200 | 1-[1-Methyl-2-(6-trifluoromethoxy-benzothiazol-2-ylamino)-1H-benzoimidazol-5-yl]-ethanone |
| 201 | (5-Methanesulfonyl-1-methyl-1H-benzoimidazol-2-yl)-(6-trifluoromethoxy-benzothiazol-2-yl)-amine |
| 202 | 2-[1-Methyl-2-(6-trifluoromethoxy-benzothiazol-2-ylamino)-1H-benzoimidazol-6-yl]-acetamide |
| 203 | 2-(6-Chloro-benzothiazol-2-ylamino)-1-methyl-1H-benzoimidazole-5-carboxylic acid ((R)-2-hydroxy-propyl)-amide |
| 204 | 2-(6-Chloro-benzothiazol-2-ylamino)-1-methyl-1H-benzoimidazole-5-carboxylic acid ((S)-2-hydroxy-propyl)-amide |
| 205 | 1-Methyl-2-(6-trifluoromethyl-benzothiazol-2-ylamino)-1H-benzoimidazole-5-carboxylic acid ((R)-2-hydroxy-propyl)-amide |
| 206 | 1-Methyl-2-(6-trifluoromethyl-benzothiazol-2-ylamino)-1H-benzoimidazole-5-carboxylic acid ((S)-2-hydroxy-propyl)-amide |
| 207 | 2-(6-Chloro-benzothiazol-2-ylamino)-1-methyl-1H-benzoimidazole-5-carboxylic acid (2-methoxy-2-methyl-propyl)-amide |
| 208 | 1-Methyl-2-(6-trifluoromethyl-benzothiazol-2-ylamino)-1H-benzoimidazole-5-carboxylic acid (2-methoxy-2-methyl-propyl)-amide |
| 209 | 2-(6-Chloro-benzothiazol-2-ylamino)-1-methyl-1H-benzoimidazole-5-carboxylic acid (2-fluoro-ethyl)-amide |
| 210 | 1-Methyl-2-(6-trifluoromethyl-benzothiazol-2-ylamino)-1H-benzoimidazole-5-carboxylic acid (2-fluoro-ethyl)-amide |
| 211 | 1-Methyl-2-(6-trifluoromethoxy-benzothiazol-2-ylamino)-1H-benzoimidazole-5-carboxylic acid cyanomethyl-amide |
| 212 | 1-Methyl-2-(6-trifluoromethoxy-benzothiazol-2-ylamino)-1H-benzoimidazole-5-carboxylic acid (2-cyano-ethyl)-amide |
| 213 | 2-(6-Chloro-benzothiazol-2-ylamino)-1-methyl-1H-benzoimidazole-5-carboxylic acid (2-cyano-ethyl)-amide |
| 214 | 2-(6-Chloro-benzothiazol-2-ylamino)-1-methyl-1H-benzoimidazole-5-carboxylic acid (3-hydroxy-propyl)-amide |
| 215 | 2-(6-Chloro-benzothiazol-2-ylamino)-1-methyl-1H-benzoimidazole-5-carboxylic acid (3-hydroxy-butyl)-amide |
| 216 | 1-Methyl-2-(6-trifluoromethyl-benzothiazol-2-ylamino)-1H-benzoimidazole-5-carboxylic acid (3-hydroxy-butyl)-amide |
| 217 | 1-Methyl-2-(6-trifluoromethyl-benzothiazol-2-ylamino)-1H-benzoimidazole-5-carboxylic acid (3-hydroxy-2,2-dimethyl-propyl)-amide |
| 218 | 2-(6-Chloro-benzothiazol-2-ylamino)-1-methyl-1H-benzoimidazole-5-carboxylic acid (3-hydroxy-2,2-dimethyl-propyl)-amide |
| 219 | 1-Methyl-2-(6-trifluoromethoxy-benzothiazol-2-ylamino)-1H-benzoimidazole-5-carboxylic acid (4-hydroxy-butyl)-amide |
| 220 | 2-(6-Chloro-1H-benzoimidazol-2-ylamino)-1-methyl-1H-benzoimidazole-5-carboxylic acid (4-hydroxy-butyl)-amide |
| 221 | 1-Methyl-2-(6-trifluoromethyl-benzothiazol-2-ylamino)-1H-benzoimidazole-5-carboxylic acid (4-hydroxy-butyl)-amide |
| 222 | 6-Fluoro-1-methyl-2-(6-trifluoromethoxy-benzothiazol-2-ylamino)-1H-benzoimidazole-5-carboxylic acid (4-hydroxy-butyl)-amide |
| 223 | 1-Methyl-2-(6-trifluoromethoxy-benzothiazol-2-ylamino)-1H-benzoimidazole-5-carboxylic acid ((R)-4-hydroxy-3-methyl-butyl)-amide |
| 224 | 2-(6-Chloro-benzothiazol-2-ylamino)-1-methyl-1H-benzoimidazole-5-carboxylic acid ((R)-4-hydroxy-3-methyl-butyl)-amide |
| 225 | 2-(6-Chloro-benzothiazol-2-ylamino)-1-methyl-1H-benzoimidazole-5-carboxylic acid (trans-4-hydroxy-cyclohexyl)-amide |
| 226 | 1-Methyl-2-(6-trifluoromethoxy-benzothiazol-2-ylamino)-1H-benzoimidazole-5-carboxylic acid (5-hydroxy-pentyl)-amide |
| 227 | 2-(6-Chloro-benzothiazol-2-ylamino)-1-methyl-1H-benzoimidazole-5-carboxylic acid (5-hydroxy-pentyl)-amide |

TABLE A-continued

| No. | Name |
|---|---|
| 228 | 1-Methyl-2-(6-trifluoromethyl-benzothiazol-2-ylamino)-1H-benzoimidazole-5-carboxylic acid (5-hydroxy-pentyl)-amide |
| 229 | 1-Methyl-2-(6-trifluoromethoxy-benzothiazol-2-ylamino)-1H-benzoimidazole-5-carboxylic acid (5-hydroxy-4,4-dimethyl-pentyl)-amide |
| 230 | 1-Methyl-2-(6-trifluoromethoxy-benzothiazol-2-ylamino)-1H-benzoimidazole-5-carboxylic acid 4-hydroxy-benzylamide |
| 231 | 1-Methyl-2-(6-trifluoromethoxy-benzothiazol-2-ylamino)-1H-benzoimidazole-5-carboxylic acid 3-hydroxy-4-methoxy-benzylamide |
| 232 | 1-Methyl-2-(6-trifluoromethoxy-benzothiazol-2-ylamino)-1H-benzoimidazole-5-carboxylic acid (trans-4-hydroxy-cyclohexylmethyl)-amide |
| 233 | 2-(6-Chloro-benzothiazol-2-ylamino)-1-methyl-1H-benzoimidazole-5-carboxylic acid (trans-4-hydroxy-cyclohexylmethyl)-amide |
| 234 | 1-Methyl-2-(6-trifluoromethyl-benzothiazol-2-ylamino)-1H-benzoimidazole-5-carboxylic acid (trans-4-hydroxy-cyclohexylmethyl)-amide |
| 235 | 2-(6-Chloro-benzothiazol-2-ylamino)-1-methyl-1H-benzoimidazole-5-carboxylic acid [2-(2-hydroxy-ethoxy)-ethyl]-amide |
| 236 | 1-Methyl-2-(6-trifluoromethyl-benzothiazol-2-ylamino)-1H-benzoimidazole-5-carboxylic acid [2-(2-hydroxy-ethoxy)-ethyl]-amide |
| 237 | 6-Fluoro-1-methyl-2-(6-trifluoromethoxy-benzothiazol-2-ylamino)-1H-benzoimidazole-5-carboxylic acid [2-(2-hydroxy-ethoxy)-ethyl]-amide |
| 238 | 3-Methyl-2-(6-trifluoromethoxy-benzothiazol-2-ylamino)-3H-imidazo[4,5-b]pyridine-6-carboxylic acid [2-(2-hydroxy-ethoxy)-ethyl]-amide |
| 239 | 1-(2-Methylamino-ethyl)-2-(6-trifluoromethoxy-benzothiazol-2 ylamino)-1H-benzoimidazole-5-carboxylic acid[2-(2-hydroxy-ethoxy)-ethyl]-amide hydrochloride |
| 240 | 2-(6-Chloro-benzothiazol-2-ylamino)-1-(2-methylamino-ethyl)-1H-benzoimidazole-5-carboxylic acid [2-(2-hydroxy-ethoxy)-ethyl]-amide hydrochloride |
| 241 | 1-(2-Methoxy-ethyl)-2-(6-trifluoromethoxy-benzothiazol-2-ylamino)-1H-benzoimidazole-5-carboxylic acid [2-(2-hydroxy-ethoxy)-ethyl]-amide |
| 242 | 1-Methyl-2-(6-trifluoromethoxy-benzothiazol-2-ylamino)-1H-benzoimidazole-5-carboxylic acid [2-((R)-2-hydroxy-1-methyl-ethoxy)-ethyl]-amide |
| 243 | 2-(6-Chloro-benzothiazol-2-ylamino)-1-methyl-1H-benzoimidazole-5-carboxylic acid [2-((R)-2-hydroxy-1-methyl-ethoxy)-ethyl]-amide |
| 244 | 1-Methyl-2-(6-trifluoromethoxy-benzothiazol-2-ylamino)-1H-benzoimidazole-5-carboxylic acid [2-(2-hydroxy-propoxy)-ethyl]-amide |
| 245 | 1-Methyl-2-(6-trifluoromethoxy-benzothiazol-2-ylamino)-1H-benzoimidazole-5-carboxylic acid [2-(2-hydroxy-2-methyl-propoxy)-ethyl]-amide |
| 246 | 1-Methyl-2-(6-trifluoromethoxy-benzothiazol-2-ylamino)-1H-benzoimidazole-5-carboxylic acid [2-(3-hydroxy-propoxy)-ethyl]-amide |
| 247 | 1-Methyl-2-(6-trifluoromethoxy-benzothiazol-2-ylamino)-1H-benzoimidazole-5-carboxylic acid [2-(3-fluoro-propoxy)-ethyl]-amide |
| 248 | 2-(6-Chloro-benzothiazol-2-ylamino)-1-methyl-1H-benzoimidazole-5-carboxylic acid [2-(3-hydroxy-propoxy)-ethyl]-amide |
| 249 | 2-(6-Chloro-benzothiazol-2-ylamino)-1-methyl-1H-benzoimidazole-5-carboxylic acid [2-(3-fluoro-propoxy)-ethyl]-amide |
| 250 | 1-Methyl-2-(6-trifluoromethoxy-benzothiazol-2-ylamino)-1H-benzoimidazole-5-carboxylic acid [3-(2-hydroxy-ethoxy)-propyl]-amide |
| 251 | 1-Methyl-2-(6-trifluoromethoxy-benzothiazol-2-ylamino)-1H-benzoimidazole-5-carboxylic acid [2-(4-hydroxy-phenyl)-ethyl]-amide |
| 252 | 1-Methyl-2-(6-trifluoromethoxy-benzothiazol-2-ylamino)-1H-benzoimidazole-5-carboxylic acid [2-(3-hydroxy-phenyl)-ethyl]-amide |
| 253 | 1-Methyl-2-(6-trifluoromethoxy-benzothiazol-2-ylamino)-1H-benzoimidazole-5-carboxylic acid [2-(4-hydroxy-cyclohexyl)-ethyl]-amide |
| 254 | 1-Methyl-2-(6-trifluoromethoxy-benzothiazol-2-ylamino)-1H-benzoimidazole-5-carboxylic acid (trans-4-hydroxymethyl-cyclohexylmethyl)-amide |
| 255 | 2-(6-Chloro-benzothiazol-2-ylamino)-1-methyl-1H-benzoimidazole-5-carboxylic acid (trans-4-hydroxymethyl-cyclohexylmethyl)-amide |
| 256 | 1-Methyl-2-(6-trifluoromethoxy-benzothiazol-2-ylamino)-1H-benzoimidazole-5-carboxylic acid {2-[2-(2-hydroxy-ethoxy)-ethoxy]-ethyl}-amide |
| 257 | 1-Methyl-2-(6-trifluoromethyl-benzothiazol-2-ylamino)-1H-benzoimidazole-5-carboxylic acid [2-(2-fluoro-ethoxy)-ethyl]-amide |
| 258 | 1-Methyl-2-(6-trifluoromethoxy-benzothiazol-2-ylamino)-1H-benzoimidazole-5-carboxylic acid [2-(2,2-difluoro-ethoxy)-ethyl]-amide |
| 259 | 2-(6-Chloro-benzothiazol-2-ylamino)-1-methyl-1H-benzoimidazole-5-carboxylic acid [2-(2,2-difluoro-ethoxy)-ethyl]-amide |
| 260 | 1-Methyl-2-(6-trifluoromethoxy-benzothiazol-2-ylamino)-1H-benzoimidazole-5-carboxylic acid [2-(2-methoxy-ethoxy)-ethyl]-amide |
| 261 | 2-(6-Chloro-benzothiazol-2-ylamino)-1-methyl-1H-benzoimidazole-5-carboxylic acid [2-(2-methoxy-ethoxy)-ethyl]-amide |
| 262 | 1-Methyl-2-(6-trifluoromethyl-benzothiazol-2-ylamino)-1H-benzoimidazole-5-carboxylic acid [2-(2-methoxy-ethoxy)-ethyl]-amide |
| 263 | 1-Methyl-2-(6-trifluoromethoxy-benzothiazol-2-ylamino)-1H-benzoimidazole-5-carboxylic acid [2-(tetrahydro-pyran-2-yl)-ethyl]-amide |
| 264 | 1-Methyl-2-(6-trifluoromethoxy-benzothiazol-2-ylamino)-1H-benzoimidazole-5-carboxylic acid [2-(tetrahydro-pyran-4-yl)-ethyl]-amide |
| 265 | 1-Methyl-2-(6-trifluoromethoxy-benzothiazol-2-ylamino)-1H-benzoimidazole-5-carboxylic acid [2-(2-cyano-ethoxy)-ethyl]-amide |
| 266 | 2-(6-Chloro-benzothiazol-2-ylamino)-1-methyl-1H-benzoimidazole-5-carboxylic acid [2-(2-cyano-ethoxy)-ethyl]-amide |

TABLE A-continued

| No. | Name |
|---|---|
| 267 | 1-Methyl-2-(6-trifluoromethoxy-benzothiazol-2-ylamino)-1H-benzoimidazole-5-carboxylic acid (2-carbamoylmethoxy-ethyl)-amide |
| 268 | 1-Methyl-2-(6-trifluoromethoxy-benzothiazol-2-ylamino)-1H benzoimidazole-5-carboxylic acid [2-(2-amino-ethoxy)-ethyl]-amide |
| 269 | 2-(6-Chloro-benzothiazol-2-ylamino)-1-methyl-1H-benzoimidazole-5-carboxylic acid [2-(2-amino-ethoxy)-ethyl]-amide |
| 270 | 2-(4-Chloro-benzothiazol-2-ylamino)-1-methyl-1H benzoimidazole-5-carboxylic acid [2-(2-amino-ethoxy)-ethyl]-amide |
| 271 | 1-Methyl-2-(6-trifluoromethoxy-benzothiazol-2-ylamino)-1H-benzoimidazole-5-carboxylic acid [2-(2-methylamino-ethoxy)-ethyl]-amide hydrochloride |
| 272 | 2-(6-Chloro-benzothiazol-2-ylamino)-1-methyl-1H-benzoimidazole-5-carboxylic acid [2-(2-methylamino-ethoxy)-ethyl]-amide hydrochloride |
| 273 | 1-Methyl-2-(6-trifluoromethoxy-benzothiazol-2-ylamino)-1H-benzoimidazole-5-carboxylic acid [2-(2-dimethylamino-ethoxy)-ethyl]-amide |
| 274 | 2-(6-Chloro-benzothiazol-2-ylamino)-1-methyl-1H-benzoimidazole-5-carboxylic acid [2-(2-dimethylamino-ethoxy)-ethyl]-amide |
| 275 | 1-Methyl-2-(6-trifluoromethoxy-benzothiazol-2-ylamino)-1H-benzoimidazole-5-carboxylic acid [2-(2-acetylamino-ethoxy)-ethyl]-amide |
| 276 | 1-Methyl-2-(6-trifluoromethoxy-benzothiazol-2-ylamino)-1H-benzoimidazole-5-carboxylic acid [2-(2-methanesulfonylamino-ethoxy)-ethyl]-amide |
| 277 | 2-(6-Chloro-benzothiazol-2-ylamino)-1-methyl-1H-benzoimidazole-5-carboxylic acid (2-ethanesulfonyl-ethyl)-amide |
| 278 | 2-(6-Chloro-benzothiazol-2-ylamino)-1-methyl-1H-benzoimidazole-5-carboxylic acid [2-(2-hydroxy-ethanesulfonyl)-ethyl]-amide |
| 279 | 2-(6-Chloro-benzothiazol-2-ylamino)-1-methyl-1H-benzoimidazole-5-carboxylic acid [2-(2-fluoro-ethylamino)-ethyl]-amide hydrochloride |
| 280 | 1-Methyl-2-(6-trifluoromethoxy-benzothiazol-2-ylamino)-1H-benzoimidazole-5-carboxylic acid ((S)-2,3-dihydroxy-propyl)-amide |
| 281 | 1-Methyl-2-(6-trifluoromethoxy-benzothiazol-2-ylamino)-1H-benzoimidazole-5-carboxylic acid ((R)-2,3-dihydroxy-propyl)-amide |
| 282 | 1-Methyl-2-(6-trifluoromethoxy-benzothiazol-2-ylamino)-1H-benzoimidazole-5-carboxylic acid ((1R,2S,3R,4R)-2,3-dihydroxy-4-hydroxymethyl-cyclopentyl)-amide |
| 283 | 1-Methyl-2-(6-trifluoromethoxy-benzothiazol-2-ylamino)-1H-benzoimidazole-5-carboxylic acid ((2S,3R,4R,5S,6R)-2,4,5-trihydroxy-6-hydroxymethyl-tetrahydro-pyran-3-yl)-amide |
| 284 | 1-Methyl-2-(6-trifluoromethoxy-benzothiazol-2-ylamino)-1H-benzoimidazole-5-carboxylic acid bis-(2-hydroxy-ethyl)-amide |
| 285 | 1-Methyl-2-(6-trifluoromethoxy-benzothiazol-2-ylamino)-1H-benzoimidazole-5-carboxylic acid (4-hydroxy-butyl)-amide |
| 286 | 1-Methyl-2-(6-trifluoromethoxy-benzothiazol-2-ylamino)-1H-benzoimidazole-5-carboxylic acid [2-(2-hydroxy-ethoxy)-ethyl]-amide |
| 287 | 2-(6-Chloro-benzothiazol-2-ylamino)-1-methyl-1H-benzoimidazole-5-carboxylic acid (4-hydroxy-butyl)-amide |
| 288 | 2-(6-Chloro-benzothiazol-2-ylamino)-1-methyl-1H-benzoimidazole-5-carboxylic acid [2-(2-hydroxy-ethoxy)-ethyl]-amide |
| 289 | 1-Methyl-2-(6-trifluoromethoxy-benzothiazol-2-ylamino)-1H-benzoimidazole-5-carboxylic acid pyrrolidin-3-ylamide hydrochloride |
| 290 | 2-(6-Chloro-benzothiazol-2-ylamino)-1-methyl-1H-benzoimidazole-5-carboxylic acid (R)-pyrrolidin-3-ylamide hydrochloride |
| 291 | 2-(6-Chloro-benzothiazol-2-ylamino)-1-methyl-1H-benzoimidazole-5-carboxylic acid (S)-pyrrolidin-3-ylamide hydrochloride |
| 292 | 2-(6-Chloro-benzothiazol-2-ylamino)-1-methyl-1H-benzoimidazole-5-carboxylic acid [(R)-1-(2-hydroxy-ethyl)-pyrrolidin-3-yl]-amide |
| 293 | 2-(6-Chloro-benzothiazol-2-ylamino)-1-methyl-1H-benzoimidazole-5-carboxylic acid [(S)-1-(2-hydroxy-ethyl)-pyrrolidin-3-yl]-amide |
| 294 | 1-Methyl-2-(6-trifluoromethoxy-benzothiazol-2-ylamino)-1H-benzoimidazole-5-carboxylic acid [1-((R)-2-hydroxy-propyl)-pyrrolidin-3-yl]-amide |
| 295 | 2-(6-Chloro-benzothiazol-2-ylamino)-1-methyl-1H-benzoimidazole-5-carboxylic acid [(R)-1-((S)-2-hydroxy-propionyl)-pyrrolidin-3-yl]-amide |
| 296 | 2-(6-Chloro-benzothiazol-2-ylamino)-1-methyl-1H-benzoimidazole-5-carboxylic acid [(R)-1-((R)-2-hydroxy-propyl)-pyrrolidin-3-yl]-amide |
| 297 | 1-Methyl-2-(6-trifluoromethyl-benzothiazol-2-ylamino)-1H-benzoimidazole-5-carboxylic acid [(R)-1-((R)-2-hydroxy-propyl)-pyrrolidin-3-yl]-amide |
| 298 | 1-Methyl-2-(6-trifluoromethoxy-benzothiazol-2-ylamino)-1H-benzoimidazole-5-carboxylic acid [1-(2-hydroxy-2-methyl-propyl)-pyrrolidin-3-yl]-amide |
| 299 | 3-(3-{[2-(6-Chloro-benzothiazol-2-ylamino)-1-methyl-1H-benzoimidazole-5-carbonyl]-amino}-pyrrolidin-1-yl)-propionic acid |
| 300 | 2-(6-Chloro-benzothiazol-2-ylamino)-1-methyl-1H-benzoimidazole-5-carboxylic acid [1-(2-methanesulfonylamino-ethyl)-pyrrolidin-3-yl]-amide |
| 301 | 2-(6-Chloro-benzothiazol-2-ylamino)-1-(2-methoxy-ethyl)-1H-benzoimidazole-5-carboxylic acid [1-(2-hydroxy-ethyl)-piperidin-4-yl]-amide |
| 302 | 2-(6-Chloro-benzothiazol-2-ylamino)-1-methyl-1H-benzoimidazole-5-carboxylic acid (piperidin-4-ylmethyl)-amide hydrochloride |
| 303 | 2-(6-Chloro-benzothiazol-2-ylamino)-1-methyl-1H-benzoimidazole-5-carboxylic acid [1-(2-hydroxy-ethyl)-piperidin-4-ylmethyl]-amide |
| 304 | 2-(6-Chloro-benzothiazol-2-ylamino)-1-(2-methoxy-ethyl)-1H-benzoimidazole-5-carboxylic acid [1-(2-hydroxy-ethyl)-piperidin-4-ylmethyl]-amide |

TABLE A-continued

| No. | Name |
|---|---|
| 305 | [4-(2-Hydroxy-ethyl)-piperazin-1-yl]-[1-methyl-2-(6-trifluoromethoxy-benzothiazol-2-ylamino)-1H-benzoimidazol-5-yl]-methanone |
| 306 | [2-(6-Chloro-benzothiazol-2-ylamino)-1-methyl-1H-benzoimidazol-5-yl]-[4-(2-hydroxy-ethyl)-piperazin-1-yl]-methanone |
| 307 | [4-(3-Hydroxy-propyl)-piperidin-1-yl]-[1-methyl-2-(6-trifluoromethoxy-benzothiazol-2-ylamino)-1H benzoimidazol-5-yl]-methanone |
| 308 | 2-(6-Chloro-benzothiazol-2-ylamino)-1-methyl-1H-benzoimidazole-5-carboxylic acid [(R)-1-(2-dimethylamino-acetyl)-pyrrolidin-3-yl]-amide |
| 309 | 2-(6-Chloro-benzothiazol-2-ylamino)-1-methyl-1H-benzoimidazole-5-carboxylic acid (R)-piperidin-3-ylamide hydrochloride |
| 310 | 2-(6-Chloro-benzothiazol-2-ylamino)-1-methyl-1H-benzoimidazole-5-carboxylic acid (S)-piperidin-3-ylamide hydrochloride |
| 311 | 2-(6-Chloro-benzothiazol-2-ylamino)-1-methyl-1H-benzoimidazole-5-carboxylic acid [(R)-1-(2-dimethylamino-acetyl)-piperidin-3-yl]-amide |
| 312 | 2-(6-Chloro-benzothiazol-2-ylamino)-1-methyl-1H-benzoimidazole-5-carboxylic acid [(S)-1-(2-dimethylamino-acetyl)-piperidin-3-yl]-amide |
| 313 | 2-(6-Chloro-benzothiazol-2-ylamino)-1-methyl-1H-benzoimidazole-5-carboxylic acid [1-(2-dimethylamino-acetyl)-piperidin-4-yl]-amide |
| 314 | 2-(6-Chloro-benzothiazol-2-ylamino)-1-methyl-1H-benzoimidazole-5-carboxylic acid [1-(2-dimethylamino-acetyl)-piperidin-4-ylmethyl]-amide |
| 315 | 2-(6-Chloro-benzothiazol-2-ylamino)-1-(2-methoxy-ethyl)-1H-benzoimidazole-5-carboxylic acid [1-(2-dimethylamino-acetyl)-piperidin-4-ylmethyl]-amide |
| 316 | 2-(6-Chloro-benzothiazol-2-ylamino)-1-methyl-1H benzoimidazole-5-carboxylic acid ((R)-1-methyl-pyrrolidin-3-yl)-amide |
| 317 | 2-(6-Chloro-benzothiazol-2 ylamino)-1-methyl-1H-benzoimidazole-5-carboxylic acid ((S)-1-methyl-pyrrolidin-3-yl)-amide |
| 318 | 2-(6-Chloro-benzothiazol-2-ylamino)-1-methyl-1H-benzoimidazole-5-carboxylic acid (1-methyl-piperidin-2-ylmethyl)-amide |
| 319 | 2-(6-Chloro-benzothiazol-2-ylamino)-1-methyl-1H-benzoimidazole-5-carboxylic acid (1-methyl-piperidin-4-yl)-amide |
| 320 | 2-(6-Chloro-benzothiazol-2-ylamino)-1-methyl-1H-benzoimidazole-5-carboxylic acid (1-methanesulfonyl-piperidin-4-yl)-amide |
| 321 | 2-(6-Chloro-benzothiazol-2-ylamino)-1-methyl-1H-benzoimidazole-5-carboxylic acid morpholin-4-ylamide |
| 322 | 1-Methyl-2-(6-trifluoromethoxy-benzothiazol-2-ylamino)-1H-benzoimidazole-5-carboxylic acid (2-methanesulfonylamino-ethyl)-amide |
| 323 | 1-Methyl-2-(6-trifluoromethoxy-benzothiazol-2-ylamino)-1H-benzoimidazole-5-carboxylic acid [2-(2-dimethylamino-acetylamino)-ethyl]-amide |
| 324 | 2-(6-Chloro-benzothiazol-2-ylamino)-1-methyl-1H-benzoimidazole-5-carboxylic acid [2-(2-dimethylamino-acetylamino)-ethyl]-amide |
| 325 | 1-Methyl-2-(6-trifluoromethoxy-benzothiazol-2-ylamino)-1H-benzoimidazole-5-carboxylic acid [2-(2-hydroxy-acetylamino)-ethyl]-amide |
| 326 | 1-Methyl-2-(6-trifluoromethoxy-benzothiazol-2-ylamino)-1H-benzoimidazole-5-carboxylic acid [2-((S)-2-hydroxy-propionylamino)-ethyl]-amide |
| 327 | 1-Methyl-2-(6-trifluoromethoxy-benzothiazol-2-ylamino)-1H-benzoimidazole-5-carboxylic acid (2-imidazol-1-yl-ethyl)-amide |
| 328 | 1-Methyl-2-(6-trifluoromethoxy-benzothiazol-2-ylamino)-1H-benzoimidazole-5-carboxylic acid (2-pyrazol-1-yl-ethyl)-amide |
| 329 | 1-Methyl-2-(6-trifluoromethoxy-benzothiazol-2-ylamino)-1H-benzoimidazole-5-carboxylic acid [2-(2-oxo-pyrrolidin-1-yl)-ethyl]-amide |
| 330 | 1-Methyl-2-(6-trifluoromethoxy-benzothiazol-2-ylamino)-1H-benzoimidazole-5-carboxylic acid [2-(2-oxo-imidazolidin-1-yl)-ethyl]-amide |
| 331 | 2-(6-Chloro-benzothiazol-2-ylamino)-1-methyl-1H-benzoimidazole-5-carboxylic acid [2-(3-oxo-piperazin-1-yl)-ethyl]-amide |
| 332 | 2-(6-Chloro-benzothiazol-2-ylamino)-1-(2-methoxy-ethyl)-1H-benzoimidazole-5-carboxylic acid [2-(3-oxo-piperazin-1-yl)-ethyl]-amide |
| 333 | 1-Methyl-2-(6-trifluoromethoxy-benzothiazol-2-ylamino)-1H-benzoimidazole-5-carboxylic acid (2-piperidin-1-yl-ethyl)-amide |
| 334 | 2-(6-Chloro-benzothiazol-2-ylamino)-1-methyl-1H-benzoimidazole-5-carboxylic acid (2-piperidin-1-yl-ethyl)-amide |
| 335 | 2-(6-Chloro-benzothiazol-2-ylamino)-1-methyl-1H-benzoimidazole-5-carboxylic acid [2-(4,4-difluoro-piperidin-1-yl)-ethyl]-amide |
| 336 | 2-(6-Chloro-benzothiazol-2-ylamino)-1-methyl-1H-benzoimidazole-5-carboxylic acid [2-(3,3-difluoro-piperidin-1-yl)-ethyl]-amide |
| 337 | 1-Methyl-2-(6-trifluoromethoxy-benzothiazol-2-ylamino)-1H-benzoimidazole-5-carboxylic acid [2-(4-methyl-piperazin-1-yl)-ethyl]-amide |
| 338 | 2-(6-Chloro-benzothiazol-2-ylamino)-1-methyl-1H-benzoimidazole-5-carboxylic acid [2-(4-methyl-piperazin-1-yl)-ethyl]-amide |
| 339 | 2-(6-Chloro-benzothiazol-2-ylamino)-1-methyl-1H-benzoimidazole-5-carboxylic acid (2-piperazin-1-yl-ethyl)-amide hydrochloride |
| 340 | 2-(6-Chloro-benzothiazol-2-ylamino)-1-methyl-1H-benzoimidazole-5-carboxylic acid (2-morpholin-4-yl-ethyl)-amide |
| 341 | 1-Methyl-2-(6-trifluoromethyl-benzothiazol-2-ylamino)-1H-benzoimidazole-5-carboxylic acid (2-morpholin-4-yl-ethyl)-amide |
| 342 | 1-Methyl-2-(6-trifluoromethoxy-benzothiazol-2-ylamino)-1H-benzoimidazole-5-carboxylic acid [2-(1,1-dioxo-thiomorpholin-4-yl)-ethyl]-amide |
| 343 | 2-(6-Chloro-benzothiazol-2-ylamino)-1-methyl-1H-benzoimidazole-5-carboxylic acid (2-amino-ethyl)-amide hydrochloride |

TABLE A-continued

| No. | Name |
|---|---|
| 344 | 1-Methyl-2-(6-trifluoromethoxy-benzothiazol-2-ylamino)-1H-benzoimidazole-5-carboxylic acid (3-amino-propyl)-amide hydrochloride |
| 345 | 2-(6-Chloro-benzothiazol-2-ylamino)-1-methyl-1H-benzoimidazole-5-carboxylic acid (3-amino-propyl)-amide hydrochloride |
| 346 | 1-Methyl-2-(6-trifluoromethoxy-benzothiazol-2-ylamino)-1H-benzoimidazole-5-carboxylic acid (4-amino-butyl)-amide hydrochloride |
| 347 | 2-(6-Chloro-benzothiazol-2-ylamino)-1-methyl-1H-benzoimidazole-5-carboxylic acid (4-amino-butyl)-amide hydrochloride |
| 348 | 1-Methyl-2-(6-trifluoromethoxy-benzothiazol-2-ylamino)-1H-benzoimidazole-5-carboxylic acid (3-dimethylamino-propyl)-amide |
| 349 | 2-(6-Chloro-benzothiazol-2-ylamino)-1-methyl-1H-benzoimidazole-5-carboxylic acid (3-dimethylamino-propyl)-amide |
| 350 | 1-Methyl-2-(6-trifluoromethyl-benzothiazol-2-ylamino)-1H-benzoimidazole-5-carboxylic acid (3-dimethylamino-propyl)-amide |
| 351 | 1-Methyl-2-(6-trifluoromethoxy-benzothiazol-2-ylamino)-1H-benzoimidazole-5-carboxylic acid (3-diethylamino-propyl)-amide |
| 352 | 2-(6-Chloro-benzothiazol-2-ylamino)-1-methyl-1H-benzoimidazole-5-carboxylic acid (3-diethylamino-propyl)-amide |
| 353 | 1-Methyl-2-(6-trifluoromethyl-benzothiazol-2-ylamino)-1H-benzoimidazole-5-carboxylic acid (3-diethylamino-propyl)-amide |
| 354 | 2-(6-Chloro-benzothiazol-2-ylamino)-1-methyl-1H-benzoimidazole-5-carboxylic acid (3-pyrrolidin-1-yl-propyl)-amide |
| 355 | 1-Methyl-2-(6-trifluoromethoxy-benzothiazol-2-ylamino)-1H-benzoimidazole-5-carboxylic acid [3-(4-methyl-piperazin-1-yl)-propyl]-amide |
| 356 | 2-(6-Chloro-benzothiazol-2-ylamino)-1-methyl-1H-benzoimidazole-5-carboxylic acid [3-(4-methyl-piperazin-1-yl)-propyl]-amide |
| 357 | 1-Methyl-2-(6-trifluoromethyl-benzothiazol-2-ylamino)-1H-benzoimidazole-5-carboxylic acid [3-(4-methyl-piperazin-1-yl)-propyl]-amide |
| 358 | 1-Methyl-2-(6-trifluoromethoxy-benzothiazol-2-ylamino)-1H-benzoimidazole-5-carboxylic acid (3-morpholin-4-yl-propyl)-amide |
| 359 | 2-(6-Chloro-benzothiazol-2-ylamino)-1-methyl-1H-benzoimidazole-5-carboxylic acid (3-morpholin-4-yl-propyl)-amide |
| 360 | 1-Methyl-2-(6-trifluoromethoxy-benzothiazol-2-ylamino)-1H-benzoimidazole-5-carboxylic acid (4-diethylamino-butyl)-amide |
| 361 | 6-Diethylamino-1-methyl-2-(6-trifluoromethoxy-benzothiazol-2-ylamino)-1H-benzoimidazole-5-carboxylic acid dimethylcarbamoylmethyl-amide |
| 362 | 6-Diethylamino-1-methyl-2-(6-trifluoromethoxy-benzothiazol-2-ylamino)-1H-benzoimidazole-5-carboxylic acid (2-morpholin-4-yl-ethyl)-amide |
| 363 | 1-Methyl-2-(6-methyl-benzothiazol-2-ylamino)-1H-benzoimidazole-5-carboxylic acid dimethylcarbamoylmethyl-amide |
| 364 | 2-(6-Ethoxy-benzothiazol-2-ylamino)-1-methyl-1H-benzoimidazole-5-carboxylic acid dimethylcarbamoylmethyl-amide |
| 365 | 2-(6-Isopropyl-benzothiazol-2-ylamino)-1-methyl-1H-benzoimidazole-5-carboxylic acid dimethylcarbamoylmethyl-amide |
| 366 | 2-(6-Chloro-benzothiazol-2-ylamino)-1-(2-methoxy-ethyl)-1H-benzoimidazole-5-carboxylic acid dimethylcarbamoylmethyl-amide |
| 367 | 2-(6-Chloro-benzothiazol-2-ylamino)-1-(2-methylamino-ethyl)-1H-benzoimidazole-5-carboxylic acid dimethylcarbamoylmethyl-amide hydrochloride |
| 368 | 1-Methyl-2-(6-trifluoromethoxy-benzothiazol-2-ylamino)-1H-benzoimidazole-5-carboxylic acid ((S)-1-dimethylcarbamoyl-2-hydroxy-ethyl)-amide |
| 369 | 1-Methyl-2-(6-trifluoromethyl-benzothiazol-2-ylamino)-1H-benzoimidazole-5-carboxylic acid ((S)-5-amino-1-dimethylcarbamoyl-pentyl)-amide hydrochloride |
| 370 | 1-Methyl-2-(6-trifluoromethyl-benzothiazol-2-ylamino)-1H-benzoimidazole-5-carboxylic acid ((S)-5-dimethylamino-1-dimethylcarbamoyl-pentyl)-amide |
| 371 | 2-(6-Chloro-benzothiazol-2-ylamino)-1-methyl-1H-benzoimidazole-5-carboxylic acid (2-dimethylcarbamoyl-ethyl)-amide |
| 372 | 1-Methyl-2-(6-trifluoromethyl-benzothiazol-2-ylamino)-1H-benzoimidazole-5-carboxylic acid (2-dimethylcarbamoyl-ethyl)-amide |
| 373 | 2-(6-Chloro-benzothiazol-2-ylamino)-1-methyl-1H-benzoimidazole-5-carboxylic acid (3-morpholin-4-yl-3-oxo-propyl)-amide |
| 374 | 1-Methyl-2-(6-trifluoromethyl-benzothiazol-2-ylamino)-1H-benzoimidazole-5-carboxylic acid (3-morpholin-4-yl-3-oxo-propyl)-amide |
| 375 | 1-Methyl-2-(6-trifluoromethyl-benzothiazol-2-ylamino)-1H-benzoimidazole-5-carboxylic acid [3-(4-methyl-piperazin-1-yl)-3-oxo-propyl]-amide |
| 376 | 2-(6-Chloro-benzothiazol-2-ylamino)-1-methyl-1H-benzoimidazole-5-carboxylic acid (3-dimethylcarbamoyl-propyl)-amide |
| 377 | 2-(6-Chloro-benzothiazol-2-ylamino)-1-methyl-1H-benzoimidazole-5-carboxylic acid [4-(4-methyl-piperazin-1-yl)-4-oxo-butyl]-amide |
| 378 | 4-{[2-(6-Chloro-benzothiazol-2-ylamino)-1-methyl-1H-benzoimidazole-5-carbonyl]-amino}-trans-cyclohexanecarboxylic acid |
| 379 | 2-(6-Chloro-benzothiazol-2-ylamino)-1-methyl-1H-benzoimidazole-5-carboxylic acid (4-trans-dimethylcarbamoyl-cyclohexyl)-amide |
| 380 | 2-(6-Chloro-benzothiazol-2-ylamino)-1-methyl-1H-benzoimidazole-5-carboxylic acid methylcarbamoylmethyl-amide |
| 381 | 1-Methyl-2-(6-trifluoromethyl-benzothiazol-2-ylamino)-1H-benzoimidazole-5-carboxylic acid methylcarbamoylmethyl-amide |
| 382 | 2-(6-Chloro-benzothiazol-2-ylamino)-1-methyl-1H-benzoimidazole-5-carboxylic acid [((R)-2-hydroxy-propylcarbamoyl)-methyl]-amide |

TABLE A-continued

| No. | Name |
|---|---|
| 383 | 2-(6-Chloro-benzothiazol-2-ylamino)-1-methyl-1H-benzoimidazole-5-carboxylic acid [(2-methanesulfonyl-ethylcarbamoyl)-methyl]-amide |
| 384 | 2-(6-Chloro-benzothiazol-2-ylamino)-1-methyl-1H-benzoimidazole-5-carboxylic acid [(tetrahydro-furan-3-ylcarbamoyl)-methyl]-amide |
| 385 | 2-(6-Chloro-benzothiazol-2-ylamino)-1-methyl-1H-benzoimidazole-5-carboxylic acid [(tetrahydro-pyran-4-ylcarbamoyl)-methyl]-amide |
| 386 | 2-(6-Chloro-benzothiazol-2-ylamino)-1-methyl-1H-benzoimidazole-5-carboxylic acid [(1-methyl-piperidin-4-ylcarbamoyl)-methyl]-amide |
| 387 | 2-(6-Chloro-benzothiazol-2-ylamino)-1-methyl-1H-benzoimidazole-5-carboxylic acid ((R)-piperidin-3-ylcarbamoylmethyl)-amide hydrochloride |
| 388 | 2-(6-Chloro-benzothiazol-2-ylamino)-1-methyl-1H-benzoimidazole-5-carboxylic acid [((R)-1-methyl-piperidin-3-ylcarbamoyl)-methyl]-amide |
| 389 | 1-Methyl-2-(6-trifluoromethoxy-benzothiazol-2-ylamino)-1H-benzoimidazole-5-carboxylic acid [(4-hydroxy-benzylcarbamoyl)-methyl]-amide |
| 390 | 1-Methyl-2-(6-trifluoromethoxy-benzothiazol-2-ylamino)-1H-benzoimidazole-5-carboxylic acid {[(2-hydroxy-ethyl)-methyl-carbamoyl]-methyl}-amide |
| 391 | 2-(6-Chloro-benzothiazol-2-ylamino)-1-methyl-1H-benzoimidazole-5-carboxylic acid {[(2-hydroxy-ethyl)-methyl-carbamoyl]-methyl}-amide |
| 392 | 1-Methyl-2-(6-trifluoromethoxy-benzothiazol-2-ylamino)-1H-benzoimidazole-5-carboxylic acid {[bis-(2-hydroxy-ethyl)-carbamoyl]-methyl}-amide |
| 393 | 2-(6-Chloro-benzothiazol-2-ylamino)-1-methyl-1H-benzoimidazole-5-carboxylic acid {[methyl-(tetrahydro-pyran-4-yl)-carbamoyl]-methyl}-amide |
| 394 | 2-(6-Chloro-benzothiazol-2-ylamino)-1-methyl-1H-benzoimidazole-5-carboxylic acid [(methyl-pyrrolidin-3-yl-carbamoyl)-methyl]-amide hydrochloride |
| 395 | 2-(6-Chloro-benzothiazol-2-ylamino)-1-methyl-1H-benzoimidazole-5-carboxylic acid {[methyl-(1-methyl-pyrrolidin-3-yl)-carbamoyl]-methyl}-amide |
| 396 | 2-(6-Chloro-benzothiazol-2-ylamino)-1-methyl-1H-benzoimidazole-5-carboxylic acid [(methyl-piperidin-3-yl-carbamoyl)-methyl]-amide hydrochloride |
| 397 | 2-(6-Chloro-benzothiazol-2-ylamino)-1-methyl-1H-benzoimidazole-5-carboxylic acid (2-oxo-2-pyrrolidin-1-yl-ethyl)-amide |
| 398 | 1-Methyl-2-(6-trifluoromethoxy-benzothiazol-2-ylamino)-1H-benzoimidazole-5-carboxylic acid [2-(3-hydroxy-pyrrolidin-1-yl)-2-oxo-ethyl]-amide |
| 399 | 2-(6-Chloro-benzothiazol-2-ylamino)-1-methyl-1H-benzoimidazole-5-carboxylic acid [2-(3-hydroxy-pyrrolidin-1-yl)-2-oxo-ethyl]-amide |
| 400 | 2-(6-Chloro-benzothiazol-2-ylamino)-1-methyl-1H-benzoimidazole-5-carboxylic acid [2-((R)-3-hydroxy-pyrrolidin-1-yl)-2-oxo-ethyl]-amide |
| 401 | 2-(6-Chloro-benzothiazol-2-ylamino)-1-methyl-1H-benzoimidazole-5-carboxylic acid [2-((S)-3-hydroxy-pyrrolidin-1-yl)-2-oxo-ethyl]-amide |
| 402 | 1-Methyl-2-(6-trifluoromethyl-benzothiazol-2-ylamino)-1H-benzoimidazole-5-carboxylic acid [2-((R)-3-hydroxy-pyrrolidin-1-yl)-2-oxo-ethyl]-amide |
| 403 | 1-Methyl-2-(6-trifluoromethyl-benzothiazol-2-ylamino)-1H-benzoimidazole-5-carboxylic acid [2-((S)-3-hydroxy-pyrrolidin-1-yl)-2-oxo-ethyl]-amide |
| 404 | 2-(6-Chloro-benzothiazol-2-ylamino)-1-(2-methoxy-ethyl)-1H-benzoimidazole-5-carboxylic acid [2-((R)-3-hydroxy-pyrrolidin-1-yl)-2-oxo-ethyl]-amide |
| 405 | 2-(6-Chloro-benzothiazol-2-ylamino)-1-(2-methoxy-ethyl)-1H-benzoimidazole-5-carboxylic acid [2-((S)-3-hydroxy-pyrrolidin-1-yl)-2-oxo-ethyl]-amide |
| 406 | 1-Methyl-2-(6-trifluoromethoxy-benzothiazol-2-ylamino)-1H-benzoimidazole-5-carboxylic acid [2-((S)-2-hydroxymethyl-pyrrolidin-1-yl)-2-oxo-ethyl]-amide |
| 407 | 1-Methyl-2-(6-trifluoromethoxy-benzothiazol-2-ylamino)-1H-benzoimidazole-5-carboxylic acid [2-((3S,4S)-3,4-dihydroxy-pyrrolidin-1-yl)-2-oxo-ethyl]-amide |
| 408 | 2-(6-Chloro-benzothiazol-2-ylamino)-1-methyl-1H-benzoimidazole-5-carboxylic acid [2-((R)-3-methoxy-pyrrolidin-1-yl)-2-oxo-ethyl]-amide |
| 409 | 2-(6-Chloro-benzothiazol-2-ylamino)-1-methyl-1H-benzoimidazole-5-carboxylic acid [2-((S)-3-methoxy-pyrrolidin-1-yl)-2-oxo-ethyl]-amide |
| 410 | 1-Methyl-2-(6-trifluoromethyl-benzothiazol-2-ylamino)-1H-benzoimidazole-5-carboxylic acid [2-((S)-3-methoxy-pyrrolidin-1-yl)-2-oxo-ethyl]-amide |
| 411 | 2-(6-Chloro-benzothiazol-2-ylamino)-1-methyl-1H-benzoimidazole-5-carboxylic acid [2-((S)-3-amino-pyrrolidin-1-yl)-2-oxo-ethyl]-amide hydrochloride |
| 412 | 1-Methyl-2-(6-trifluoromethoxy-benzothiazol-2-ylamino)-1H-benzoimidazole-5-carboxylic acid [2-((S)-3-amino-pyrrolidin-1-yl)-2-oxo-ethyl]-amide hydrochloride |
| 413 | 1-Methyl-2-(6-trifluoromethoxy-benzothiazol-2-ylamino)-1H-benzoimidazole-5-carboxylic acid [2-((R)-3-methylamino-pyrrolidin-1-yl)-2-oxo-ethyl]-amide hydrochloride |
| 414 | 1-Methyl-2-(6-trifluoromethoxy-benzothiazol-2-ylamino)-1H-benzoimidazole-5-carboxylic acid [2-((S)-3-methylamino-pyrrolidin-1-yl)-2-oxo-ethyl]-amide hydrochloride |
| 415 | 1-Methyl-2-(6-trifluoromethoxy-benzothiazol-2-ylamino)-1H-benzoimidazole-5-carboxylic acid [2-((R)-3-dimethylamino-pyrrolidin-1-yl)-2-oxo-ethyl]-amide |
| 416 | 1-Methyl-2-(6-trifluoromethoxy-benzothiazol-2-ylamino)-1H-benzoimidazole-5-carboxylic acid [2-((S)-3-dimethylamino-pyrrolidin-1-yl)-2-oxo-ethyl]-amide |
| 417 | 2-(6-Chloro-benzothiazol-2-ylamino)-1-methyl-1H-benzoimidazole-5-carboxylic acid [2-((R)-3-dimethylamino-pyrrolidin-1-yl)-2-oxo-ethyl]-amide |
| 418 | 2-(6-Chloro-benzothiazol-2-ylamino)-1-methyl-1H-benzoimidazole-5-carboxylic acid [2-((S)-3-dimethylamino-pyrrolidin-1-yl)-2-oxo-ethyl]-amide |
| 419 | 2-(6-Chloro-benzothiazol-2-ylamino)-1-methyl-1H-benzoimidazole-5-carboxylic acid [2-((S)-2-dimethylcarbamoyl-pyrrolidin-1-yl)-2-oxo-ethyl]-amide |
| 420 | 3-Methyl-2-(6-trifluoromethoxy-benzothiazol-2-ylamino)-3H-imidazo[4,5-b]pyridine-6-carboxylic acid (2-morpholin-4-yl-2-oxo-ethyl)-amide |

TABLE A-continued

| No. | Name |
|---|---|
| 421 | 2-(6-Chloro-benzothiazol-2-ylamino)-1-methyl-1H-benzoimidazole-5-carboxylic acid (2-morpholin-4-yl-2-oxo-ethyl)-amide |
| 422 | 1-Methyl-2-(6-trifluoromethyl-benzothiazol-2-ylamino)-1H-benzoimidazole-5-carboxylic acid (2-morpholin-4-yl-2-oxo-ethyl)-amide |
| 423 | 2-(6-Chloro-benzothiazol-2-ylamino)-1-methyl-1H-benzoimidazole-5-carboxylic acid (2-oxo-2-thiomorpholin-4-yl-ethyl)-amide |
| 424 | 2-(6-Chloro-benzothiazol-2-ylamino)-1-methyl-1H-benzoimidazole-5-carboxylic acid [2-(1,1-dioxo-thiomorpholin-4-yl)-2-oxo-ethyl]-amide |
| 425 | 2-(6-Chloro-benzothiazol-2-ylamino)-1-methyl-1H-benzoimidazole-5-carboxylic acid (2-oxo-2-piperazin-1-yl-ethyl)-amide hydrochloride |
| 426 | 2-(6-Chloro-benzothiazol-2-ylamino)-1-methyl-1H-benzoimidazole-5-carboxylic acid [2-(4-methyl-piperazin-1-yl)-2-oxo-ethyl]-amide |
| 427 | 1-Methyl-2-(6-trifluoromethyl-benzothiazol-2-ylamino)-1H-benzoimidazole-5-carboxylic acid [2-(4-methyl-piperazin-1-yl)-2-oxo-ethyl]-amide |
| 428 | 2-(6-Chloro-benzothiazol-2-ylamino)-1-(2-methoxy-ethyl)-1H-benzoimidazole-5-carboxylic acid [2-(4-methyl-piperazin-1-yl)-2-oxo-ethyl]-amide |
| 429 | 2-(6-Chloro-benzothiazol-2-ylamino)-1-methyl-1H-benzoimidazole-5-carboxylic acid [2-(4-methanesulfonyl-piperazin-1-yl)-2-oxo-ethyl]-amide |
| 430 | 2-(6-Chloro-benzothiazol-2-ylamino)-1-methyl-1H-benzoimidazole-5-carboxylic acid [2-(4-dimethylsulfamoyl-piperazin-1-yl)-2-oxo-ethyl]-amide |
| 431 | 1-Methyl-2-(6-trifluoromethoxy-benzothiazol-2-ylamino)-1H-benzoimidazole-5-carboxylic acid [2-(3-hydroxy-piperidin-1-yl)-2-oxo-ethyl]-amide |
| 432 | 1-Methyl-2-(6-trifluoromethoxy-benzothiazol-2-ylamino)-1H-benzoimidazole-5-carboxylic acid [2-((R)-3-hydroxy-piperidin-1-yl)-2-oxo-ethyl]-amide |
| 433 | 2-(6-Chloro-benzothiazol-2-ylamino)-1-methyl-1H-benzoimidazole-5-carboxylic acid [2-((S)-3-hydroxy-piperidin-1-yl)-2-oxo-ethyl]-amide |
| 434 | 1-Methyl-2-(6-trifluoromethyl-benzothiazol-2-ylamino)-1H-benzoimidazole-5-carboxylic acid [2-((S)-3-hydroxy-piperidin-1-yl)-2-oxo-ethyl]-amide |
| 435 | 1-Methyl-2-(6-trifluoromethoxy-benzothiazol-2-ylamino)-1H-benzoimidazole-5-carboxylic acid [2-(4-hydroxy-piperidin-1-yl)-2-oxo-ethyl]-amide |
| 436 | 2-(6-Chloro-benzothiazol-2-ylamino)-1-methyl-1H-benzoimidazole-5-carboxylic acid [2-(4-hydroxy-piperidin-1-yl)-2-oxo-ethyl]-amide |
| 437 | 1-Methyl-2-(6-trifluoromethyl-benzothiazol-2-ylamino)-1H-benzoimidazole-5-carboxylic acid [2-(4-hydroxy-piperidin-1-yl)-2-oxo-ethyl]-amide |
| 438 | 2-(6-Chloro-benzothiazol-2-ylamino)-1-(2-methoxy-ethyl)-1H-benzoimidazole-5-carboxylic acid [2-(4-hydroxy-piperidin-1-yl)-2-oxo-ethyl]-amide |
| 439 | 1-Methyl-2-(6-trifluoromethoxy-benzothiazol-2-ylamino)-1H-benzoimidazole-5-carboxylic acid [2-(2-hydroxymethyl-piperidin-1-yl)-2-oxo-ethyl]-amide |
| 440 | 1-Methyl-2-(6-trifluoromethoxy-benzothiazol-2-ylamino)-1H-benzoimidazole-5-carboxylic acid [2-(3-hydroxymethyl-piperidin-1-yl)-2-oxo-ethyl]-amide |
| 441 | 1-Methyl-2-(6-trifluoromethoxy-benzothiazol-2-ylamino)-1H-benzoimidazole-5-carboxylic acid [2-(4-hydroxymethyl-piperidin-1-yl)-2-oxo-ethyl]-amide |
| 442 | 2-(6-Chloro-benzothiazol-2-ylamino)-1-methyl-1H-benzoimidazole-5-carboxylic acid [2-(4-hydroxymethyl-piperidin-1-yl)-2-oxo-ethyl]-amide |
| 443 | 2-(6-Chloro-benzothiazol-2-ylamino)-1-(2-methoxy-ethyl)-1H-benzoimidazole-5-carboxylic acid [2-(4-hydroxymethyl-piperidin-1-yl)-2-oxo-ethyl]-amide |
| 444 | 2-(6-Chloro-benzothiazol-2-ylamino)-1-methyl-1H-benzoimidazole-5-carboxylic acid [2-((S)-3-methoxy-piperidin-1-yl)-2-oxo-ethyl]-amide |
| 445 | 1-Methyl-2-(6-trifluoromethyl-benzothiazol-2-ylamino)-1H-benzoimidazole-5-carboxylic acid [2-((S)-3-methoxy-piperidin-1-yl)-2-oxo-ethyl]-amide |
| 446 | 1-Methyl-2-(6-trifluoromethyl-benzothiazol-2-ylamino)-1H-benzoimidazole-5-carboxylic acid [2-((R)-3-methoxy-piperidin-1-yl)-2-oxo-ethyl]-amide |
| 447 | 1-Methyl-2-(6-trifluoromethoxy-benzothiazol-2-ylamino)-1H-benzoimidazole-5-carboxylic acid [2-(4-methoxymethyl-piperidin-1-yl)-2-oxo-ethyl]-amide |
| 448 | 1-Methyl-2-(6-trifluoromethoxy-benzothiazol-2-ylamino)-1H-benzoimidazole-5-carboxylic acid [2-(4-fluoromethyl-piperidin-1-yl)-2-oxo-ethyl]-amide |
| 449 | 1-Methyl-2-(6-trifluoromethoxy-benzothiazol-2-ylamino)-1H-benzoimidazole-5-carboxylic acid [2-oxo-2-(4-trifluoromethyl-piperidin-1-yl)-ethyl]-amide |
| 450 | 1-Methyl-2-(6-trifluoromethoxy-benzothiazol-2-ylamino)-1H-benzoimidazole-5-carboxylic acid [2-(4-cyano-piperidin-1-yl)-2-oxo-ethyl]-amide |
| 451 | 1-Methyl-2-(6-trifluoromethoxy-benzothiazol-2-ylamino)-1H-benzoimidazole-5-carboxylic acid [2-(4-carbamoyl-piperidin-1-yl)-2-oxo-ethyl]-amide |
| 452 | 1-Methyl-2-(6-trifluoromethoxy-benzothiazol-2-ylamino)-1H-benzoimidazole-5-carboxylic acid {2-oxo-2-[4-(pyrimidin-2-yloxy)-piperidin-1-yl]-ethyl}-amide |
| 453 | 1-Methyl-2-(6-trifluoromethoxy-benzothiazol-2-ylamino)-1H-benzoimidazole-5-carboxylic acid [2-(4-methylamino-piperidin-1-yl)-2-oxo-ethyl]-amide hydrochloride |
| 454 | 2-(6-Chloro-benzothiazol-2-ylamino-1-methyl-1H-benzoimidazole-5-carboxylic acid [2-(4-methylamino-piperidin-1-yl)-2-oxo-ethyl]-amide hydrochloride |
| 455 | 1-Methyl-2-(6-trifluoromethoxy-benzothiazol-2-ylamino)-1H-benzoimidazole-5-carboxylic acid [2-(4-dimethylamino-piperidin-1-yl)-2-oxo-ethyl]-amide |
| 456 | 2-(6-Chloro-benzothiazol-2-ylamino)-1-methyl-1H-benzoimidazole-5-carboxylic acid [2-(4-dimethylamino-piperidin-1-yl)-2-oxo-ethyl]-amide |
| 457 | 2-(6-Chloro-benzothiazol-2-ylamino)-1-methyl-1H-benzoimidazole-5-carboxylic acid [2-(4-methylaminomethyl-piperidin-1-yl)-2-oxo-ethyl]-amide hydrochloride |
| 458 | 1-Methyl-2-(6-trifluoromethoxy-benzothiazol-2-ylamino)-1H-benzoimidazole-5-carboxylic acid [2-(4-dimethylaminomethyl-piperidin-1-yl)-2-oxo-ethyl]-amide |
| 459 | 2-(6-Chloro-benzothiazol-2-ylamino)-1-methyl-1H-benzoimidazole-5-carboxylic acid [2-(4-dimethylaminomethyl-piperidin-1-yl)-2-oxo-ethyl]-amide |

TABLE A-continued

| No. | Name |
|---|---|
| 460 | 2-(6-Chloro-benzothiazol-2-ylamino)-1-methyl-1H-benzoimidazole-5-carboxylic acid [2-(3-methylaminomethyl-piperidin-1-yl)-2-oxo-ethyl]-amid hydrochloride |
| 461 | 2-(6-Chloro-benzothiazol-2-ylamino)-1-methyl-1H-benzoimidazole-5-carboxylic acid [2-(3-dimethylaminomethyl-piperidin-1-yl)-2-oxo-ethyl]-amide |
| 462 | 2-(6-Chloro-benzothiazol-2-ylamino)-1-methyl-1H-benzoimidazole-5-carboxylic acid ((S)-1-dimethylcarbamoyl-ethyl)-amide |
| 463 | 1-Methyl-2-(6-trifluoromethyl-benzothiazol-2-ylamino)-1H-benzoimidazole-5-carboxylic acid ((S)-1-dimethylcarbamoyl-ethyl)-amide |
| 464 | 2-(6-Chloro-benzothiazol-2-ylamino)-1-methyl-1H-benzoimidazole-5-carboxylic acid [(S)-1-methyl-2-(4-methyl-piperazin-1-yl)-2-oxo-ethyl]-amide |
| 465 | 2-(6-Chloro-benzothiazol-2-ylamino)-1-methyl-1H-benzoimidazole-5-carboxylic acid ((S)-1-methyl-2-morpholin-4-yl-2-oxo-ethyl)-amide |
| 466 | 1-Methyl-2-(6-trifluoromethyl-benzothiazol-2-ylamino)-1H-benzoimidazole-5-carboxylic acid ((S)-1-methyl-2-morpholin-4-yl-2-oxo-ethyl)-amide |
| 467 | 2-(6-Chloro-benzothiazol-2-ylamino)-1-methyl-1H-benzoimidazole-5-carboxylic acid ((R)-1-dimethylcarbamoyl-ethyl)-amide |
| 468 | 1-Methyl-2-(6-trifluoromethyl-benzothiazol-2-ylamino)-1H-benzoimidazole-5-carboxylic acid ((R)-1-dimethylcarbamoyl-ethyl)-amide |
| 469 | 2-(6-Chloro-benzothiazol-2-ylamino)-1-methyl-1H-benzoimidazole-5-carboxylic acid [(R)-1-methyl-2-(4-methyl-piperazin-1-yl)-2-oxo-ethyl]-amide |
| 470 | 1-Methyl-2-(6-trifluoromethyl-benzothiazol-2-ylamino)-1H-benzoimidazole-5-carboxylic acid [(R)-1-methyl-2-(4-methyl-piperazin-1-yl)-2-oxo-ethyl]-amide |
| 471 | 2-(6-Chloro-benzothiazol-2-ylamino)-1-methyl-1H-benzoimidazole-5-carboxylic acid ((R)-1-methyl-2-morpholin-4-yl-2-oxo-ethyl)-amide |
| 472 | 1-Methyl-2-(6-trifluoromethyl-benzothiazol-2-ylamino)-1H-benzoimidazole-5-carboxylic acid ((R)-1-methyl-2-morpholin-4-yl-2-oxo-ethyl)-amide |

Compounds in Table A and within the genus of Formula (I) may be prepared as described in WO '018 or other methods apparent to one of skill in the art.

For each use of the term Bach1 Inhibitor in this disclosure, a compound of any one of Embodiments 1 to 249 or one or more compounds in Table A may be substituted therein.

Nrf2 Activator

As used herein, the term "Nrf2 Activator" means an agent that after administration results in a stimulated and/or increased nuclear translocation of Nrf2 protein and causes the subsequent increases in expression of one or more ARE-regulated genes by acting directly on Nrf2, Keap1, and or the Nrf2-Keap1 complex.

Nrf2 Activators may comprise a Michael addition acceptor, one or more fumaric acid esters, i.e. fumaric acid mono- and/or diesters which may be selected from the group of monoalkyl hydrogen fumarate and dialkyl fumarate, such as monomethyl hydrogen fumarate, dimethyl fumarate, monoethyl hydrogen fumarate, and diethyl fumarate, furthermore ethacrynic acid, bardoxolone methyl (methyl 2-cyano-3,12-dioxooleana-1,9(11)dien-28-oate), isothiocyanate such as sulforaphane, 1,2-dithiole-3-thione such as oltipraz, 3,5-di-tert-butyl-4-hydroxytoluene, 3-hydroxycoumarin, or a pharmacologically active derivative or analog of the aforementioned agents. In an embodiment, Nrf2 Activators for use in combination with Bach Inhibitors are bardoxolone methyl and fumaric acid esters.

Fumaric acid esters ("FAEs") and other fumaric acid derivatives have been proposed for use in treating a wide-variety of diseases and conditions involving immunological, autoimmune, and/or inflammatory processes including psoriasis; asthma and chronic obstructive pulmonary diseases; cardiac insufficiency including left ventricular insufficiency, myocardial infarction and angina pectoris; mitochondrial and neurodegenerative diseases such as Parkinson's disease, Alzheimer's disease, Huntington's disease, retinopathia pigmentosa and mitochondrial encephalomyopathy; transplantation; autoimmune diseases including multiple sclerosis (MS); ischemia and reperfusion injury; Advanced Glycation End-product (AGE) induced genome damage; inflammatory bowel diseases such as Crohn's disease and ulcerative colitis; arthritis; and others. All these indications and diseases may be treated with the combination treatment of the present invention.

Nrf2 Activators compounds may be classified based on their chemical structures: Diphenols, Michael reaction acceptors, isothiocyanates, thiocarbamates, trivalent arsenicals, 1,2-dithiole-3-thiones, hydroperoxides, vicinal dimercaptans, heavy metals, and polyenes. In general, Nrf2 Activators are chemically reactive in that they may be electrophiles, substrates for glutathione transferases, and/or can modify sulfhydryl groups by alkylation, oxidation, or reduction.

In an embodiment, Nrf2 Activators are compounds without significant Bach1 inhibitory effect. In this embodiment, the Nrf2 Activator may or may not bind to Bach1 or may or may not covalently bond to Bach1, but are not able to significantly inhibit Bach1 repression of Nrf2 dependent gene transcription.

In another embodiment, Nrf2 Activators are compounds that bond covalently to Keap1 protein, such as by a sulfur atom of an amino acid residue of Keap1.

In another embodiment, the Nrf2 Activators are bardoxolone methyl and dialkyl fumarate such as dimethyl fumarate and diethyl fumarate.

In another embodiment, Nrf2 activators are selected from: Chalcone derivatives such as 2-trifluoromethyl-2'-methoxy-chalcone, auranofin, ebselen, 1,2-naphthoquinone, cynnamic aldehyde, caffeic acid and its esters, curcumin, resveratrol, artesunate, tert-butylhydroquinone, and -quinone, (tBHQ, tBQ), vitamins K1, K2 and K3, menadione, fumaric acid esters, i.e. fumaric acid mono- and/or diester which may be selected from the group of monoalkyl hydrogen fumarate and dialkyl fumarate, such as monomethyl hydrogen fumarate, dimethyl fumarate (DMF), monoethyl hydrogen fumarate, and diethyl fumarate, 2-cyclopentenones, ethacrynic acid and its alkyl esters, bardoxolone methyl (methyl 2-cyano-3,12-dioxooleana-1,9(11)dien-28-oate) (CDDO-Me, RTA 402), ethyl 2-cyano-3,12-dioxooleana-1,9(11)

dien-28-oate, 2-cyano-3,12-dioxooleana-1,9(11)dien-28-oic acid (CDDO), 1[2-Cyano-3,12-dioxooleana-1,9(11)-dien-28-oyl]imidazole (CDDO-Im), (2-cyano-N-methyl-3,12-dioxooleana-1,9(11)-dien-28 amide (CDDO-methyl amide, CDDO-MA), isothiocyanate such as sulforaphane, 1,2-dithiole-3-thione such as oltipraz, 3,5-di-tert-butyl-4-hydroxytoluene, 3-hydroxycoumarin, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, corticosteroids, such as dexamethasone, 8-iso prostaglandin A2, alkyl pyruvate, such as methyl and ethyl pyruvate, diethyl or dimethyl oxalopropionate, 2-acetamidoacrylate, methyl or ethyl-2-acetamidoacrylate, hypoestoxide, parthenolide, eriodictyol, 4-hydroxy-2-nonenal, 4-oxo-2nonenal, geranial, zerumbone, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(methylthio)-3-butenyl isothiocyanate and 6-methylsulfinylhexyl isothiocyanate, ferulic acid and its esters, such as ferulic acid ethyl ester, and ferulic acid methyl ester, sofalcone, 4-methyl daphnetin, imperatorin, auraptene, poncimarin, bis[2-hydroxybenzylidene]acetones, alicylcurcuminoid, 4-bromo flavone, .beta.-naphthoflavone, sappanone A, aurones and its corresponding indole derivatives such as benzylidene-indolin-2-ones, perillaldehyde, quercetin, fisetin, koparin, genistein, tanshinone HA, BHA, BHT, PMX-290, AL-1, avicin D, gedunin, fisetin, andrographolide, and tricyclic bis(cyano enone) TBE-31 [(+/−)-(4bS,8aR,10aS)-10a-ethynyl-4-b,8,8-trimethyl-3,7-dioxo-3,4-b,7,8,-8a,9,10,10a-octahydrophenanthrene-2,6-dicarbonitrile].

In another embodiment, Nrf2 activators are selected from: carnosic acid, 2-naphthoquinone, cynnamic aldehyde, caffeic acid and its esters, curcumin, reservatrol, artesunate, tert-butylhydroquinone, vitamins K1, K2 and K3, fumaric acid esters, i.e. fumaric acid mono- and/or diester which is preferably selected from the group of monoalkyl hydrogen fumarate and dialkyl fumarate, such as monomethyl hydrogen fumarate, dimethyl fumarate, monoethyl hydrogen fumarate, and diethyl fumarate, isothiocyanate such as sulforaphane, 1,2-dithiole-3-thione such as oltipraz, 3,5-di-tert-butyl-4-hydroxytoluene, 3-hydroxycoumarin, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, 8-iso prostaglandin A2, alkyl pyruvate, such as methyl and ethyl pyruvate, diethyl or dimethyl oxalopropionate, 2-acetamidoacrylate, methyl or ethyl-2-acetamidoacrylate, hypoestoxide, parthenolide, eriodictyol, 4-Hydroxy-2-nonenal, 4-oxo-2nonenal, geranial, zerumbone, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(Methylthio)-3-butenyl isothiocyanate and 6-methylsulfinylhexyl isothiocyanate and the respective quinone or hydroquinone forms of the aforementioned quinone and hydroquinone derivatives.

In another embodiment, Nrf2 Activators may be Michael reaction acceptors such as dimethylfumarate, monomethyl hydrogen fumarate isothiocyanates and 1,2-dithiole-3-thiones. In another embodiment, Nrf2 Activators are selected from monomethyl hydrogen fumarate, dimethyl fumarate, oltipraz, 1,2-naphthoquinone, tert-butylhydroquinone, methyl or ethyl pyruvate, 3,5-di-tert-butyl-4-hydroxytoluene, diethyl and dimethyl oxalopropionate, hypoestoxide, parthenolide, eriodictyol, 4-Hydroxy-2-nonenal, 4-oxo-2nonenal, geranial, zerumbone, aurone, isoliquiritigenin, xanthohumol, [10]-Shogaol, eugenol, 1'-acetoxychavicol acetate, allyl isothiocyanate, benzyl isothiocyanate, phenethyl isothiocyanate, 4-(Methylthio)-3-butenyl isothiocyanate and 6-Methylsulfinylhexyl isothiocyanate.

II. Combinations

As defined herein, the Bach1 Inhibitors and the Nrf2 Activators may have complementary mechanisms of action. Administration of each agent alone may result in upregulation of one or more ARE-regulated genes, but, because each agent may cause this upregulation through separate mechanisms, one agent may increase the baseline sensitivity of the system to the other agent. Thus, agents with complimentary mechanisms of action may act such that the therapeutically effective dose of either agent or both may be reduced relative to mono-therapy doses. Further, the combined therapeutically effective dose of both agents may be less than an additive substitution of one agent for the other. Put another way, the therapeutic effect when the Bach1 Inhibitor and the Nrf2 Activator are used together may be more than additive, i.e. greater than the sum of the effects that result from using each agent alone. For example, administering a Bach1 Inhibitor may reduce the amount of Bach1 available to repress expression of ARE-regulated genes in a system, and thereby increase the sensitivity of the system to Nrf2. This increase in sensitivity may reduce the amount of an Nrf2 Activator necessary to achieve a therapeutic effect.

In an embodiment, the combined use of a Bach1 Inhibitor and an Nrf2 Activator may eliminate, reduced incidence, or reduce severity of adverse effect(s) associated with use of the Bach1 Inhibitor or the Nrf2 Activator as mono-therapies. In another embodiment, the combined use of a Bach1 Inhibitor and an Nrf2 Activator may reduce the dose of one or both of the agents employed in the combination treatment, and, the side effect(s) that may be observed in mono-therapy with the agents may be avoided or reduced. For example, dimethyl fumarate may potentially cause reduction in white cell count, flushing, redness, itching, skin rash, nausea, vomiting, diarrhea, stomach or abdominal pain, indigestion, and/or dyspepsia when administered in therapeutically effective amounts, such as 240 mg BID. The combined use of a Bach1 Inhibitor and dimethyl fumarate may reduce the dose of dimethyl fumarate needed to achieve a therapeutic benefit for a subject, such as an individual suffering from multiple sclerosis. As a result of reduction in dose, the likelihood and/or severity of any one of the side effects associated with administering dimethyl fumarate may be reduced. In another example, administration of bardoxolone methyl may be associated with fluid retention, heart failure, and/or muscle spasm when administered in therapeutically effective amounts, such as about 20 mg/day. The combined use of a Bach1 Inhibitor and bardoxolone methyl may reduce the dose of bardoxolone methyl needed to achieve a therapeutic benefit for a subject, such as an individual suffering from chronic kidney disease. As a result of reduction in dose, the likelihood and/or severity of any one of the side effects associated with administering bardoxolone methyl may be reduced.

The combination treatment of the present invention may be further combined with treatments and medicaments that are generally used in the various indications as a standard treatment. For example, in the treatment of multiple sclerosis, the combination treatment of the present invention may be further combined with interferon, such as interferon beta 1b or interferon beta 1a (Rebif, Avonex) or glatiramer acetate (Copaxone), a sphingosine 1-phosphate receptor modulator, such as Fingolimod (Gilenya) and/or methotrexate. The combination treatment of the present invention can be further combined with RXR specific ligands, such as 9-cis-retinoic acid (RA) such as in the treatment of psoriasis.

As used herein, a combination therapy may be administered as a simultaneous or sequential regimen, also referred to as co-administration. When administered sequentially, the combination may be administered in two or more administrations. It is also possible to combine a Bach1 Inhibitor with an Nrf2 Activator in a unitary dosage form for simultaneous administration to a subject. Co-administration of a Bach1 Inhibitor with an Nrf2 Activator refers to simultaneous or sequential administration of a Bach1 Inhibitor and an Nrf2 Activator, such that therapeutically effective amounts of the Bach1 Inhibitor and the Nrf2 Activator are both present at the same time in the body of the subject. Co-administration includes simultaneous administration and administration of an agent before or after administration of the other agent, for example, administration of both agents within seconds, minutes, or hours of each other. In one embodiment, the first agent is administered, followed, after a period of hours, e.g., 0.25-12 hours, or 0.5 to 3 hours, or 1 to 2 hours, by administration of the second agent.

A. Dosage Forms

In an embodiment, the Bach1 Inhibitors and Nrf2 Activators may used for preparing oral preparations in the form of tablets, micro-tablets, pellets or granulates, optionally in capsules or sachets. Discrete or separate preparation of the Bach1 Inhibitor and the Nrf2 Activator may be used. Further, the route of administration of the separate preparation may be the same or different. For example, the Bach1 Inhibitor may be prepared for oral administration, while the Nrf2 Activator may be prepared for topical administration.

Preparations in the form of micro-tablets or pellets, optionally filled in capsules or sachets may be used and are also a subject matter of the invention. The oral preparations may be provided with an enteric coating. Capsules may be soft or hard gelatine capsules. The dialkyl fumarates used according to the invention may be used alone or as a mixture of several compounds, optionally in combination with the customary carriers and excipients.

In an embodiment, the Bach1 Inhibitors and Nrf2 Activators may be combined into a fixed-dose combination, such as a tablet. In embodiments where the Bach1 Inhibitor and the Nrf2 Activator are combined, the amount of the Bach1 Inhibitor may be a therapeutically effective amount. In another embodiment, the amount of the Bach1 Inhibitor may be a suboptimal amount. In an embodiment, the amount of the Nrf2 Activator may be a therapeutically effective amount. In another embodiment, the amount of the Nrf2 Activator may be a suboptimal amount. In another embodiment, the amount of the Bach1 Inhibitor and the Nrf2 Activator are both suboptimal amounts.

In another embodiment, pharmaceutical compositions provided by the present disclosure may comprise a Bach1 Inhibitor and an Nrf2 Activator and a pharmaceutically acceptable carrier so as to provide a composition for proper administration to a subject.

In certain embodiments, a Bach1 Inhibitor and an Nrf2 Activator may together be incorporated into a pharmaceutical composition to be administered orally. In another embodiment, a topical formulation is provided, containing a Bach1 Inhibitor, and an Nrf2 Activator. In an embodiment, the Nrf2 Activator is one that does not or only rarely cause an allergic skin reaction, such as bardoxolone methyl (CDDO-Me), CDDO, CDDO-IM, CDDO-MA, TP-225, menadione, vitamin K1, BHA, BHT, tBHQ, tBQ, curcumin, reservatrol, cynnamic aldehyde or oltipraz. The topical formulation may used in the treatment of psoriasis, acne, rosacea and skin rash such as skin rash caused by EGFR inhibitors like cetuximab, zalutumumab, nimotuzumab, and matuzumab, gefitinib, erlotinib, and lapatinib. The formulations are prepared with customary ingredients and processes known in the art and/or disclosed herein.

Pharmaceutical compositions comprising a Bach Inhibitor and an Nrf2 Activator may be manufactured by means of conventional mixing, dissolving, granulating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of the Bach1 Inhibitor and the Nrf2 Activator into formulations that can be used pharmaceutically. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a subject. Pharmaceutical compositions provided by the present disclosure may be formulated in a unit dosage form. A unit dosage form refers to a physically discrete unit suitable as a unitary dose for subjects undergoing treatment, with each unit containing a predetermined quantity of Bach1 Inhibitor and an Nrf2 Activator calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a subject at a single point in time or during a time interval.

Pharmaceutical compositions comprising a Bach1 Inhibitor and an Nrf2 Activator may be formulated for immediate release or controlled or sustained or delayed release.

In certain embodiments, an oral dosage form provided may be a controlled release dosage form. Controlled delivery technologies may improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the agent with a particular release profile in the gastrointestinal tract. Examples of controlled release dosage forms include dissolution controlled systems, diffusion controlled systems, ion exchange resins, osmotically controlled systems, erodable matrix systems, pH independent formulations, gastric retention systems, and the like.

In certain embodiments, pharmaceutical compositions may be practiced with dosage forms adapted to provide sustained release of a Bach1 Inhibitor and an Nrf2 Activator upon oral administration. Sustained release oral dosage forms may be used to release the Bach1 Inhibitor and/or the Nrf2 Activator over a prolonged time period and are useful when it is desired that an agent be delivered to the lower gastrointestinal tract. Sustained release oral dosage forms include diffusion-controlled systems such as reservoir devices and matrix devices, dissolution-controlled systems, osmotic systems, and erosion-controlled systems.

In each of the above dosage forms, the Bach1 Inhibitor may be formulated together in admixture or separately from the Nrf2 Activator. The Bach1 Inhibitor and Nrf2 Activator may be contained in separate form within the dosage form, such as an oral dosage form, which is a tablet or capsule. In such oral dosage form, wherein the Bach1 Inhibitor and the Nrf2 Activator are separated, each agent may be formulated with different excipients. The Bach1 Inhibitor and the Nrf2 Activator may also be each contained in formulations with different release profiles, i.e. with immediate, controlled or delayed release.

In an embodiment, a pharmaceutical composition is provided comprising a Bach1 Inhibitor and a fumaric acid mono- and/or diester and a pharmaceutically acceptable carrier.

In a further embodiment, the fumaric acid mono- and/or diester is selected from the group of monomethyl hydrogen fumarate, dimethyl fumarate, monoethyl hydrogen fumarate and diethyl fumarate. In a further embodiment, the pharmaceutical composition is a solid oral dosage form. In a further embodiment, a solid oral dosage form is provided characterized in that the Bach1 Inhibitor and the fumaric acid mono- and/or diester are each contained in the dosage form in a separate composition.

In another embodiment, a pharmaceutical composition is provided comprising a Bach1 Inhibitor and bardoxolone alkyl and a pharmaceutically acceptable carrier. In a further embodiment, the bardoxolone alkyl is bardoxolone methyl. In a further embodiment, the pharmaceutical composition is a solid oral dosage form. In a further embodiment, a solid oral dosage form is provided characterized in that the Bach1 Inhibitor and the bardoxolone alkyl are each contained in the dosage form in a separate composition.

In any of the previous embodiments of pharmaceutical compositions, the Bach1 Inhibitor may be a compound of Embodiment 1 to 249 or a compound in Table A described above.

B. Dosage Amounts

An appropriate dose of a Bach1 Inhibitor and an Nrf2 Activator or pharmaceutical composition comprising a Bach1 Inhibitor and an Nrf2 Activator for use in the present invention, may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

i. Bach1 Inhibitors

In an embodiment, a Bach1 Inhibitor may be administered in combination with an Nrf2 Activator according to the invention, such as orally, in daily dosages of between 0.1 mg and 15 mg per kg, dependent on the activity and safety of the respective Bach1 Inhibitor. In another embodiment, where the subject is a human the daily dose of the Bach1 Inhibitor may be between 1 mg and 1000 mg. In another embodiment, the Bach1 Inhibitor is administered to a subject in combination with an Nrf2 Activator, wherein the amount of the Bach1 Inhibitor administered is from 10 mg/day to 1000 mg/day, or from 25 mg/day to 800 mg/day, or from 37 mg/day to 750 mg/day, or from 75 mg/day to 700 mg/day, or from 100 mg/day to 600 mg/day, or from 150 mg/day to 500 mg/day, or from 200 mg/day to 400 mg/day. In some further embodiments, the Bach1 Inhibitor is administered to a subject (e.g., a human), in combination with an Nrf2 Activator, in an amount of less than 100 mg/day, or less than 200 mg/day, or less than 300 mg/day, or less than 400 mg/day, or less than 500 mg/day. If not indicated otherwise, the dosages given above and below reflect the amount of free base of the Bach1 Inhibitor, even if used in form of a salt.

In another embodiment, the amount of the Bach1 Inhibitor administered in combination with the Nrf2 Activator may be a suboptimal amount of Bach1 Inhibitor, where a suboptimal amount of Bach1 Inhibitor is an amount that is below the therapeutically effective amount as a monotherapy in a typical subjection (such as a human subject that suffers from one of the relevant indications like multiple sclerosis). In some such embodiments, the suboptimal amount of the Bach1 Inhibitor may be from 10 mg/day to 1000 mg/day, or from 25 mg/day to 800 mg/day, or from 37 mg/day to 750 mg/day, or from 75 mg/day to 700 mg/day, or from 100 mg/day to 600 mg/day, or from 150 mg/day to 500 mg/day, or from 200 mg/day to 400 mg/day. In a further embodiment, the suboptimal amount of Bach1 Inhibitor administered to a subject (e.g., a human) may be an amount of less than 100 mg/day, or less than 200 mg/day, or less than 300 mg/day, or less than 400 mg/day, or less than 500 mg/day.

ii. Nrf2 Activators

In an embodiment, a daily dosage of 0.1 mg to 20 mg per kg body weight, dependent on the activity and safety of the respective Nrf2 activator may be used.

In another embodiment, preparations may contain a total amount of 10 to 300 mg of dimethyl fumarate and/or diethyl fumarate. In another embodiment, dimethyl fumarate may be administered according to the invention in daily dosages of 1 to 20 mg per kg body weight, or in daily dosages of 2 to 15 mg per kg body weight, or in daily dosages of 3 mg to 12 mg per kg body weight, or in daily dosages of about 3.4 mg, about 7 mg or about 10 mg per kg body weight. Daily oral dosages of about 240 mg, about 480 mg and about 720 mg dimethyl fumarate per subject may be used. If the Nrf2 activator is dimethyl fumarate, once or twice daily dosing is preferred.

In another embodiment, bardoxolone methyl is may be administered according to the invention in daily dosages of 0.1 to 3 mg per kg body weight, or in daily dosages of 0.2 to 2.5 mg per kg body weight, or in daily dosages of 0.3 mg to 2.2 mg per kg body weight, or in daily dosages of about 0.35 mg, about 1.1 mg or about 2 mg per kg body weight. Daily oral dosages of about 25 mg, about 75 mg, and about 150 mg or bardoxolone methyl per subject may be used.

In another embodiment, the amount of the Nrf2 Activator administered in combination with the Bach1 Inhibitor may be a suboptimal amount of Nrf2 Activator, where a suboptimal amount of Nrf2 Activator is an amount that is below the therapeutically effective amount as a mono-therapy in a typical subject (such as a human subject that suffers from one of the relevant indications like multiple sclerosis). In some such embodiments, the suboptimal amount of the Nrf2 Activator is from 10 mg/day to 1000 mg/day, or from 25 mg/day to 800 mg/day, or from 37 mg/day to 750 mg/day, or from 75 mg/day to 700 mg/day, or from 100 mg/day to 600 mg/day, or from 150 mg/day to 500 mg/day, or from 200 mg/day to 400 mg/day. In a further embodiment, the suboptimal amount of Nrf2 Activator administered to a subject (e.g., a human) is an amount of less than 100 mg/day, or less than 200 mg/day, or less than 300 mg/day, or less than 400 mg/day, or less than 500 mg/day. If the Nrf2 Activator is dimethyl fumarate, then a suboptimal amount may be less than 480 mg/day, or less than 240 mg/day, or less than 120 mg/day. If the Nrf2 Activator is bardoxolone, then the suboptimal amount may be less than 10 mg/day, or 25 mg/day, or 75 mg/day, or 150 mg/day.

If not indicated otherwise, the dosages given above and below reflect the amount of free base of the Nrf2 Activator, even if used in the form of a salt.

C. Kits

In another embodiment, a kit of parts is provided comprising a) a Bach1 Inhibitor and b) an Nrf2 Activator, and optionally c) instructions for a dosing regime. The Bach1 Inhibitor may be a compound of Embodiment 1 to 249 or a compound in Table A described above.

In another embodiment, a kit of parts is provided comprising a) a Bach1 Inhibitor and b) a fumaric acid mono- and/or diester and optionally c) instructions for a dosing regime. The Bach1 Inhibitor may be a compound of Embodiment 1 to 249 or a compound in Table A described above. In a further embodiment, the fumaric acid mono- and/or diester is selected from the group of monomethyl hydrogen fumarate, dimethyl fumarate, monoethyl hydrogen fumarate and diethyl fumarate.

In another embodiment, a kit of parts is provided comprising a) a Bach1 Inhibitor and b) a bardoxolone alkyl and optionally c) instructions for a dosing regime. The Bach1 Inhibitor may be a compound of Embodiment 1 to 249 or a compound in Table A described above. In a further embodiment, the bardoxolone alkyl is bardoxolone methyl.

In another embodiment, a kit of parts is provided comprising a) a Bach1 Inhibitor and b) an Nrf2 Activator, where the Nrf2 Activator has no significant Bach1 inhibitory effect, and optionally c) instructions for a dosing regime. The Bach1 Inhibitor may be a compound of Embodiment 1 to 249 or a compound in Table A described above. In a further embodiment, the bardoxolone alkyl is bardoxolone methyl.

III. Methods of Treatment and Methods of Use

In one embodiment, the invention provides a combination of an Nrf2 Activator and a Bach1 Inhibitor for use in the treatment of inflammatory diseases, autoimmune diseases, and/or oxidative stress. In another embodiment, the invention provides methods of treating an autoimmune disease, an inflammatory disease, or oxidative stress associated with the disease, comprising administering an Nrf2 Activator and a Bach1 Inhibitor to a subject in need thereof.

A combination of a Bach1 Inhibitor and an Nrf2 Activator may be administered as a treatment to a subject having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases such as Parkinson's disease, Alzheimer's disease, Huntington's disease, retinopathia pigmentosa and mitochondrial encephalomyopathy, transplantation rejection, autoimmune diseases including multiple sclerosis, ischemia and reperfusion injury, advanced glycation endproducts (AGE)-induced genome and protein damage, inflammatory bowel diseases such as Crohn's disease and ulcerative colitis, thyroid eye disease-related inflammation, fibrosis, such as lung fibrosis, chronic lymphocytic leukemia, aphthous stomatitis, such as recurrent aphthous stomatitis, acute lung injury, non-alcoholic steatohepatitis acute renal injury and aging-related progressive renal injury, diabetic cardiomyopathy and nephropathy, chronic kidney disease (CKD), atherosclerosis, hypercholesterolemia, hyperlipidemia, aortic stenosis, or acute kidney injury (AKI) after surgery. The present invention can also be used in the treatment of cardiovascular disease, for plaque stabilization, reduction of inflammation, reversal of endothelial dysfunction, and decreased thrombogenicity and wound healing in diabetes. Moreover, the combination treatment can be used in the treatment of atopic dermatitis, dementia, gastritis, fibrosis, insulin resistance, type I and type II diabetes and Syndrome X.

According to another embodiment of the invention, the administration of a Bach1 Inhibitor and an Nrf2 Activator, or co-administration of a combination of a Bach1 Inhibitor and an Nrf2 Activator may be effective for treating a member of the group of diseases consisting of a neurological disorder, an ophthalmological disorder, in a subject, including, without limitation, a human. According to another embodiment the neurological disorder, an ophthalmological disorder, or a combination thereof results from at least one member of the group consisting of trauma, ischemia, and hypoxia. According to another embodiment the neurological disorder, ophthalmological disorder, or combination thereof is selected from the group consisting of painful neuropathy, neuropathic pain, diabetic neuropathy, drug dependence, drug addition, drug withdrawal, nicotine withdrawal, opiate tolerance, opiate withdrawal, depression, anxiety, a movement disorder, tardive dyskinesia, a cerebral infection that disrupts the blood-brain barrier, meningitis, meningoencephalitis, stroke, hypoglycemia, cardiac arrest, spinal cord trauma, head trauma, perinatal hypoxia, cardiac arrest, hypoglycemic neuronal damage, glaucoma, retinal ischemia, ischemic optic neuropathy, macular degeneration, multiple sclerosis, sequalae of hyperhomocystinemia, convulsion, pain, schizophrenia, muscle spasm, migraine headache, urinary incontinence, emesis, brain edema, tardive dyskinesia, AIDS-induced dementia, ocular damage, retinopathy, a cognitive disorder, and a neuronal injury associated with HIV infection. According to another embodiment the neurological disorder, ophthalmological disorder, or combination thereof is selected from the group consisting of epilepsy, Alzheimer's disease, vascular (multi-infarct) dementia, Huntington's disease, Parkinsonism, multiple sclerosis, amyotrophic lateral sclerosis, and minimal cognitive impairment (MCI).

Psoriasis is characterized by hyperkeratosis and thickening of the epidermis as well as by increased vascularity and infiltration of inflammatory cells in the dermis. Psoriasis vulgaris manifests as silvery, scaly, erythematosus plaques on typically the scalp, elbows, knees, and buttocks. Guttate psoriasis occurs as tear-drop size lesions.

Inflammatory arthritis includes diseases such as rheumatoid arthritis, juvenile rheumatoid arthritis (juvenile idiopathic arthritis), psoriatic arthritis, and ankylosing spondylitis produce joint inflammation. The pathogenesis of immune-mediated inflammatory diseases including inflammatory arthritis is believed to involve TNF and NK-.kappa.B signaling pathways. Dimethyl fumarate has been shown to inhibit TNF and inflammatory diseases including inflammatory arthritis are believed to involve TNF and NK-.kappa.B signaling and therefore may be useful in treating inflammatory arthritis.

In an embodiment, the method of treatments and combinations can be used in the prophylaxis and treatment of neurodegenerative diseases, such as multiple sclerosis, Parkinson's disease, Alzheimer's disease, Huntington's disease, dementia, mitochondrial encephalomyopathy and amyotrophic lateral sclerosis (ALS).

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual subject exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability. The clinical course of MS can vary from individual to individual, but invariably the disease can be categorized in three forms: relapsing-remitting, secondary progressive, and primary progressive.

Studies support the efficacy of fumaric acid esters for treating MS. Assessment of MS treatment efficacy in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis) Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms. The airflow limitation is usually progressive and associated with an abnormal inflammatory response of the lungs to noxious particles and gases. COPD is characterized by a shortness of breath the last for months or years, possibly accompanied by wheezing, and a persistent cough with sputum production. COPD encompasses chronic obstructive bronchiolitis with fibrosis and obstruction of small airways, and emphysema with enlargement of airspaces and destruction of lung parenchyma, loss of lung elasticity, and closure of small airways.

Neurodegenerative diseases such as Parkinson's disease, Alzheimer's disease, Huntington's disease and amyoptrophic lateral sclerosis are characterized by progressive dysfunction and neuronal death. Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. Alzheimer's disease is a progressive loss of mental function characterized by degeneration of brain tissue, including loss of nerve cells and the development of senile plaques and neurofibrillary tangles. Huntington's disease is an autosomal dominant neurodegenerative disorder in which specific cell death occurs in the neostriatum and cortex. Amyotrophic lateral sclerosis (ALS) is a progressive neurodegenerative disorder characterized by the progressive and specific loss of motor neurons in the brain, brain stem, and spinal cord.

Myasthenia gravis (MG) is a classic autoimmune disease affecting neuromuscular junctions of striated muscle. Immunization of different animal species with acetylcholine receptor (AChR) and complete Freund's adjuvant (CFA) results in an animal model of MG named experimental autoimmune myasthenia gravis (EAMG).

Thus, diseases and conditions for which treatment with the combination of a Bach1 Inhibitor and an Nrf2 Activator may also include rheumatica, granuloma annulare, lupus, autoimmune carditis, eczema, sarcoidosis, and autoimmune diseases including acute disseminated encephalomyelitis, Addison's disease, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psoriatic arthritis, polymyositis, primary biliary cirrhosis, rheumatoid arthritis, schizophrena, scleroderma, Sjogren's syndrome, stiff person syndrome, temporal arteritis, ulcerative colitis, vasculitis, vitiligo, and Wegener's granulomatosis.

In another embodiment, the disclosure provides a Bach1 Inhibitor for use in combination with a fumaric acid mono- and/or diester. In a further embodiment, the invention provides a Bach1 Inhibitor for use in combination with a fumaric acid mono- and/or diester in the treatment of an autoimmune and/or inflammatory disease. In another embodiment, the autoimmune and/or inflammatory disease is psoriasis. In another embodiment, the autoimmune and/or inflammatory disease is selected from the group of psoriatic arthritis, multiple sclerosis, inflammatory bowel disease (IBS), colitis ulcerosa, Crohn's disease, hepatitis, effluvium, diabetic nephropathy, CKD and myasthenia gravis. In a further embodiment, the fumaric acid mono- and/or diester is selected from the group of monomethyl hydrogen fumarate, dimethyl fumarate, monoethyl hydrogen fumarate and diethyl fumarate.

In another embodiment, a method of treating cancer is provided comprising administration of a Bach1 Inhibitor and an Nrf2 Activator to a subject. In a further embodiment, the cancer is heamatological cancer such as leukemia such as acute myeloid leukaemia (AML). In a further embodiment of the foregoing method, the Nrf2 Activator is other than arsenic trioxide. In a further embodiment, the Nrf2 Activator is dimethyl fumarate, monomethyl hydrogen fumarate or bardoloxone methyl.

In another embodiment, a method of treating diabetes is provided (such as type II diabetes and its complications, such as arthritis, chronic kidney disease and syndrome x) comprising administration of a Bach1 Inhibitor and an Nrf2 Activator to a subject in need thereof. In one embodiment of the foregoing method, the Nrf2 Activator is other than bardoxolone methyl and/or a corticosteroid. In another embodiment, the Nrf2 activator is dimethyl fumarate or monomethyl hydrogen fumarate.

In another embodiment, a method of treating cardiovascular diseases is provided comprising administration of a Bach1 Inhibitor and an Nrf2 Activator to a subject.

In another embodiment, a method of treating respiratory diseases is provided, such as asthma, chronic obstructive pulmonary disorder and fibrosis, comprising administration of a Bach1 Inhibitor and an Nrf2 Activator to a subject. In a further embodiment, the Nrf2 activator is other than a corticosteroid. In a further embodiment, the Nrf2 activator is dimethyl fumarate, monomethyl hydrogen fumarate or bardoloxone methyl.

In another embodiment, a method of treating or preventing graft rejection and/or necrosis is provided, comprising administration of a Bach1 Inhibitor and an Nrf2 Activator to a subject.

In another embodiment, a method of treating psoriasis is provided, comprising administration of a Bach1 Inhibitor and an Nrf2 Activator to a subject. In another embodiment of the foregoing method, no therapeutic amounts of monomethyl hydrogen fumarate are co-administered to the subject. In another embodiment of the foregoing method, no therapeutic amounts of dimethyl fumarate are co-administered to the subject. In another embodiment of the foregoing method, the Nrf2 activator is bardoloxone methyl. In another embodiment of the foregoing method, a suboptimal amount of monomethyl hydrogen fumarate, dimethyl fumarate, or bardoloxone methyl is administered to the subject.

In another embodiment, a method of treating autoimmune and/or inflammatory diseases other than psoriasis is provided, comprising administration of a Bach1 Inhibitor and dialkyl fumarate, monoalkyl hydrogen fumarate, or bardoxolone methyl to a subject. In another embodiment of the foregoing method, the Nrf2 activator is bardoloxolone methyl. In another embodiment of the foregoing method, a suboptimal amount of monomethyl hydrogen fumarate, dimethyl fumarate, or bardoloxolone methyl is administered to the subject.

In another embodiment, a method treating cardiovascular diseases, respiratory disorders, graft rejection, cancer and diabetes and its complications is provided, comprising administration of a Bach1 Inhibitor and dimethyl fumarate, monoalkyl hydrogen fumarate, or bardoxolone methyl to a subject in need thereof. In another embodiment of the foregoing method, the Nrf2 activator is bardoloxolone methyl. In another embodiment of the foregoing method, a suboptimal amount of monomethyl hydrogen fumarate, dimethyl fumarate, or bardoloxolone methyl is administered to the subject.

In another embodiment, a method of treating neurodegenerative diseases is provided, comprising administration of a Bach1 Inhibitor and a fumaric acid monoalkyl and/or dialkyl ester to a subject.

In another embodiment, a Bach1 Inhibitor is provided for use in combination with an Nrf2 Activator selected from the group of monoalkyl hydrogen fumarate, dialkyl fumarate and bardoxolone alkyl in the treatment of an autoimmune and/or inflammatory disease. In an embodiment the autoimmune and/or inflammatory disease is multiple sclerosis. In an embodiment, multiple sclerosis includes relapsing-remitting (RR), secondary progressive (SP), primary progressive (PP) and progressive relapsing (PR) multiple sclerosis and the first demyelinating event suggestive of MS or clinically isolated syndrome (CIS). In another embodiment, autoimmune and/or inflammatory disease is psoriasis. In another embodiment, the autoimmune and/or inflammatory disease is colitis ulcerosa. In another embodiment, the autoimmune and/or inflammatory disease is Crohn's disease. In another embodiment, the autoimmune and/or inflammatory disease is diabetic nephropathy. In another embodiment, the autoimmune and/or inflammatory disease is myasthenia gravis. In any of the previous embodiments in this paragraph, the Bach1 Inhibitor may be a compound of Embodiment 1 to 249 or a compound in Table A described above. In a further embodiment, the Nrf2 Activator is selected from the group of monomethyl hydrogen fumarate, dimethyl fumarate and bardoxolone methyl. In the foregoing embodiments, wherein the Bach1 Inhibitor may be administered to a subject simultaneously with or up to 2 days before or after the Nrf2 Activator, such as those selected from the group of monoalkyl hydrogen fumarate, dialkyl fumarate and bardoxolone alkyl, is administered to said subject. In another embodiment, the Bach1 Inhibitor is administered once or twice daily. In another embodiment, the Nrf2 activator is administered once or twice daily. In an embodiment, the Nrf2 Activator is dimethyl fumarate. In another embodiment, the Nrf2 Activator is bardoxolone methyl.

In another embodiment, Bach1 Inhibitor is provided for use in combination with an Nrf2 Activator in the treatment of autoimmune and/or inflammatory diseases, such as multiple sclerosis, psoriasis or chronic kidney disease. In a further embodiment, the Nrf2 Activator has no significant Bach1 inhibitory effect.

In another embodiment, a composition is provided comprising a Bach1 Inhibitor and an Nrf2 Activator for use in the treatment of autoimmune and/or inflammatory diseases, such as multiple sclerosis, psoriasis or chronic kidney disease. In an embodiment, the Nrf2 Activator has no significant Bach1 inhibitory effect.

In another embodiment, a Bach1 Inhibitor is provided for use in combination with an Nrf2 Activator such as bardoxolone methyl, in the treatment of CKD or multiple sclerosis. In an embodiment, multiple sclerosis includes relapsing-remitting (RR), secondary progressive (SP), primary progressive (PP) and progressive relapsing (PR) multiple sclerosis and the first demyelinating event suggestive of MS or clinically isolated syndrome (CIS).

In an embodiment, the Nrf2 Activator according to any of the foregoing embodiments is characterized in that the Nrf2 Activator is selected chemical compounds belonging to the group of Michael reaction acceptors, phenols, diphenols, chalcones, isothiocyanates, thiocarbamates, quinones, naphthoquinones and 1,2 dithiole-3-thiones. In another embodiment, the Nrf2 Activator is selected from 2-naphthoquinone, cynnamic aldehyde, caffeic acid and its esters, curcumin, reservatrol, artesunate, tert-butylhydroquinone, vitamins K1, K2 and K3 and the respective quinone or hydroquinone forms of the aforementioned quinone and hydroquinone derivatives, fumaric acid esters, i.e. fumaric acid mono- and/or diester which is preferably selected from the group of monoalkyl hydrogen fumarate and dialkyl fumarate, such as monomethyl hydrogen fumarate, dimethyl fumarate, monoethyl hydrogen fumarate, and diethyl fumarate, isothiocyanate such as sulforaphane, 1,2-dithiole-3-thione such as oltipraz, 3,5-di-tert-butyl-4-hydroxytoluene, 3-hydroxycoumarin, 4-hydroxynonenal, 4-oxononenal, malondialdehyde, (E)-2-hexenal, capsaicin, allicin, allylisothiocyanate, 6-methylthiohexyl isothiocyanate, 7-methylthioheptyl isothiocyanate, sulforaphane, 8-methylthiooctyl isothiocyanate, 8-iso prostaglandin A2, alkyl pyruvate, such as methyl and ethyl pyruvate, diethyl or dimethyl oxaloproprionate, 2-acetamidoacrylate, and methyl or ethyl-2-acetamidoacrylate.

In another embodiment, the Nrf2 Activator is selected from monomethyl hydrogen fumarate, dimethyl fumarate, oltipraz, 1,2-naphthoquinone, tert-butylhydroquinone, methyl or ethyl pyruvate, 3,5-di-tert-butyl-4-hydroxytoluene, or diethyl and dimethyl oxaloproprionate.

In another embodiment, a method of treating a disease associated with oxidative stress is provided comprising: administering to a subject in need thereof a Bach1 Inhibitor and an Nrf2 Activator. In an embodiment, the amount of the amount of the Bach1 Inhibitor may be a therapeutically effective amount. In another embodiment, the amount of the Bach1 Inhibitor may be a suboptimal amount. In another embodiment, the amount of the Nrf2 Activator may be a therapeutically effective amount. In another embodiment, the amount of the Nrf2 Activator may be a suboptimal amount. In another embodiment, the amount of the Bach1 Inhibitor and the Nrf2 Activator are both suboptimal amounts. In a further embodiment, the Bach1 Inhibitor and the Nrf2 Activator are administered in separate dosage forms. In an even further embodiment, the Bach1 Inhibitor and the Nrf2 Activator are administered by separate routes. In a separate embodiment, the Bach1 Inhibitor and the Nrf2 Activator are administered in a fixed dose combination. In any of the embodiments described in this paragraph, the disease associated with oxidative stress may be any of the diseases listed in this section III.

In another embodiment, a method of reducing cellular oxidative stress is provided comprising: administering a Bach1 Inhibitor to a cell in an amount sufficient to reduce the amount of Bach1 available to repress antioxidant responsive element; and administering an Nrf2 Activator. In an embodiment, this method may raise the baseline sensitivity of the cell to Nrf2.

In another embodiment, a method of treatment is provided comprising: administering to a subject a Bach1 Inhibitor in an amount sufficient to reduce the amount of Bach1 available to repress antioxidant responsive element; and administering to the subject an Nrf2 Activator. In an embodiment, this method may raise the sensitivity of the subject to Nrf2 Activators. In another embodiment, the method may increase efficacy of the Nrf2 Activator or the Bach1 Inhibitor. In any of the embodiments described in this paragraph, the disease associated with oxidative stress may be any of the diseases listed in this section III.

In another embodiment, a method is provided that reduces the Hill slope of the dose response curve of an Nrf2 Activator comprising: administering to a subject a Bach1 Inhibitor and an Nrf2 Activator. In another embodiment, a method is provided that shifts of the dose response curve of an Nrf2 Activator comprising: administering to a subject a Bach1 Inhibitor and an Nrf2 Activator. In another embodiment, a method is provided that reduces the Hill slope and shifts the dose response curve of an Nrf2 Activator comprising: administering to a subject a Bach1 Inhibitor and an Nrf2 Activator.

In certain embodiments, the Bach1 Inhibitors and Nrf2 Activators used in the combinations herein may have complementary tissue or organ exposures. For example, certain Bach1 Inhibitors may not cross the blood-brain barrier in significant amounts at therapeutically effective doses, while certain Nrf2 Activators (or immediate and active metabolites) may readily cross the blood-brain barrier at therapeutically effective doses. In another example, certain Bach1 Inhibitors may have high exposure in the stomach or gut, whereas certain Nrf2 Activators may have broad peripheral exposure.

In an embodiment, a method of treating a disease associated with oxidative stress is provided comprising: administering an Nrf2 Activator in an amount that it or a metabolite is able to significantly cross the blood brain barrier; and administering a Bach1 Inhibitor in an amount that is not able to significantly cross the blood brain barrier. In a further embodiment, the disease is multiple sclerosis. In a further embodiment, the Nrf2 Activator is dimethyl fumarate. In a further embodiment, the Nrf2 Activator metabolite is monomethyl hydrogen fumarate. In another embodiment, the Nrf2 Activator metabolite is an immediate metabolite and/or an active metabolite. In an embodiment, the brain to plasma ratio of the Nrf2 Activator or metabolite is greater than brain to plasma ratio of the Bach1 Inhibitor. In another embodiment, the brain to plasma ratio of the Nrf2 Activator is greater than 1/1, or greater than 2/1, or greater than 4/1, or greater than 8/1, or greater than 16/1. In another embodiment, the brain to plasma ratio of the Bach1 Inhibitor is less than 1/1, or less than ½, or less than ¼, or less than ⅛, or less than 1/16.

In another embodiment, a method of treating a disease associated with oxidative stress is provided comprising: administering dialkyl fumarate or a monoalkyl hydrogen fumarate; and administering a Bach1 Inhibitor in an amount that is not able to significantly cross the blood brain barrier. In a further embodiment, the disease is multiple sclerosis.

In another embodiment, a method of treating a disease associated with oxidative stress is provided comprising: administering an Nrf2 Activator in an amount that is not able to significantly cross the blood brain barrier; and administering a Bach1 Inhibitor in an amount that is able to significantly cross the blood brain barrier. In a further embodiment, the Nrf2 Activator is bardoxolone methyl. In an embodiment, the brain to plasma ratio of the Bach1 Inhibitor is greater than the brain to plasma ratio of the Nrf2 Activator. In another embodiment, the brain to plasma ratio of the Bach1 Inhibitor is greater than 1/1, or greater than 2/1, or greater than 4/1, or greater than 8/1, or greater than 16/1. In another embodiment, the brain to plasma ratio of the Nrf2 Activator is less than 1/1, or less than ½, or less than ¼, or less than ⅛, or less than 1/16.

EXAMPLES

Cell Culture

Normal Human Lung Fibroblasts (NHLF) obtained from Lonza were cultured in T-225 flasks using conditions recommended by the vendor (FGM-2 medium supplemented with 2% fetal bovine serum (FBS), fibroblast growth factor (hFGF-B) 0.5 mL, insulin 0.5 mL, and gentamicin/amphotericin-B 0.5 mL at 37° C. in a humidified atmosphere of 5% $CO_2$). Cryovials of $5 \times 10^5$ cells per mL in fetal bovine serum containing 6% DMSO were prepared and frozen in liquid nitrogen for storage for future experiments.

HMOX1 Protein Expression

For assays, cell were thawed and placed into culture in T225 flasks, grown to be 80% confluent, and harvested as described by the vendor. NHLF cells ($2.5 \times 10^4$ cells per well)

were plated in 384 well optilux tissue culture (BD) plates and incubated overnight in media prior to exposure to compound. Cells were incubated with DMSO or various combinations of either an Nrf2 Activator (DMF (dimethyl fumarate)/CDDO-Me) or a Bach1 Inhibitor for 16-18 hr. Cells were then fixed and permeabilized prior to incubation with HMOX1 antibody (abcam; 1:300 dilution in 1% BSA in PBS) for 1 hour. Cells were then washed and incubated with a solution of fluorescently-coupled goat anti-mouse antibody (Alexa 488 1:400 dilution Invitrogen) and Hoechst nuclear stain (1:2000; Invitrogen) in PBS containing 1% BSA for 1 hr. Immunostaining was detected using a GE InCell 2000 instrument at the following wavelengths: Hoechst Ex/Em 360/535 and Alexa 488 Ex/Em 480/535. Results were analyzed using GE InCell Analyzer software and represented as the increase fold of HMOX1 induction (Fold induction/FI) or the percentage of HMOX1 positive (% positive) cells over DMSO.

Bach1 Inhibitor compounds in the examples below and in Table A above may be prepared as described in International Publication No. WO 2011/103018 or other methods apparent to one of skill in the art.

TABLE B

| Reference | Cpd. In Table A | Structure |
|---|---|---|
| HPP-A | 1 | 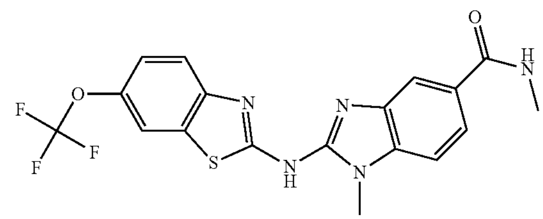 [SMILES: CNC(=O)c1ccc2c(c1)nc(Nc1nc3ccc(OC(F)(F)F)cc3s1)n2C] |
| HPP-B | 73 | 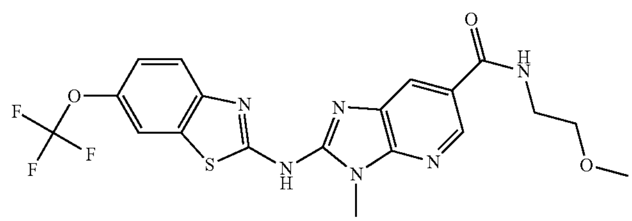 [SMILES: COCCNC(=O)c1cnc2c(c1)nc(Nc1nc3ccc(OC(F)(F)F)cc3s1)n2C] |
| HPP-C | 134 | 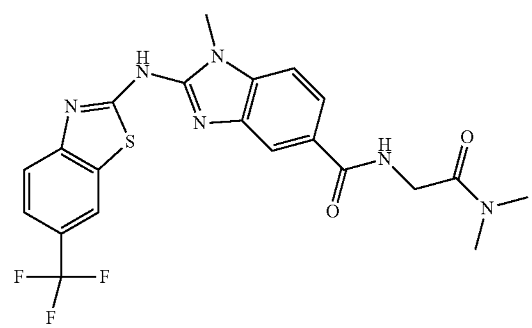 [SMILES: CN(C)C(=O)CNC(=O)c1ccc2c(c1)nc(Nc1nc3ccc(C(F)(F)F)cc3s1)n2C] |
| HPP-D | 236 | 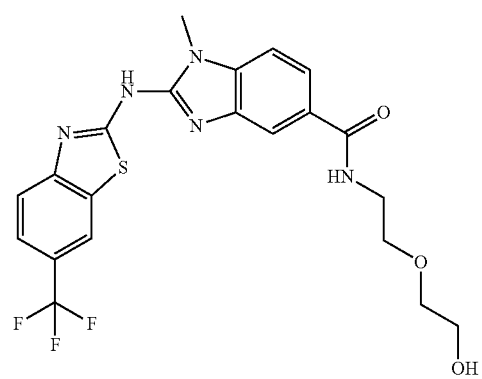 [SMILES: Cn1c(Nc2nc3ccc(C(F)(F)F)cc3s2)nc2cc(C(=O)NCCOCCO)ccc21] |

Results

Table 1 demonstrates the increase in HMOX1 induction (fold over DMSO alone) following incubation of normal human lung fibroblasts with varying concentrations of either Bach1 Inhibitor HPP-A alone, CDDO-Me alone, or the two compounds in combination. In this experiment, the maximum HMOX1 fold induction observed with HPP-A alone is 18-fold at concentrations greater than or equal to 2500 nM. Similarly, 19-fold induction of HMOX1 protein is observed with greater than or equal to 156 nM CDDO-Me.

FIG. 1 graphically demonstrates that when the two compounds are combined, significantly lower concentrations are required for similar levels of HMOX1 fold induction. FIG. 1 shows that 156 nM HPP-A and 9.7 nM CDDO-Me increase HMOX1 by 3.5 and 2.5 fold, respectively (bars A and B); however, when combined the effect on HMOX induction is greater than additive (bar C).

Likewise, Table 2 demonstrates that the combination of DMF and Bach1 Inhibitors HPP-B, HPP-C, and HPP-D at concentrations below their maximum effect are additive or greater than additive in terms of the % HMOX positive cells.

Figure 2:
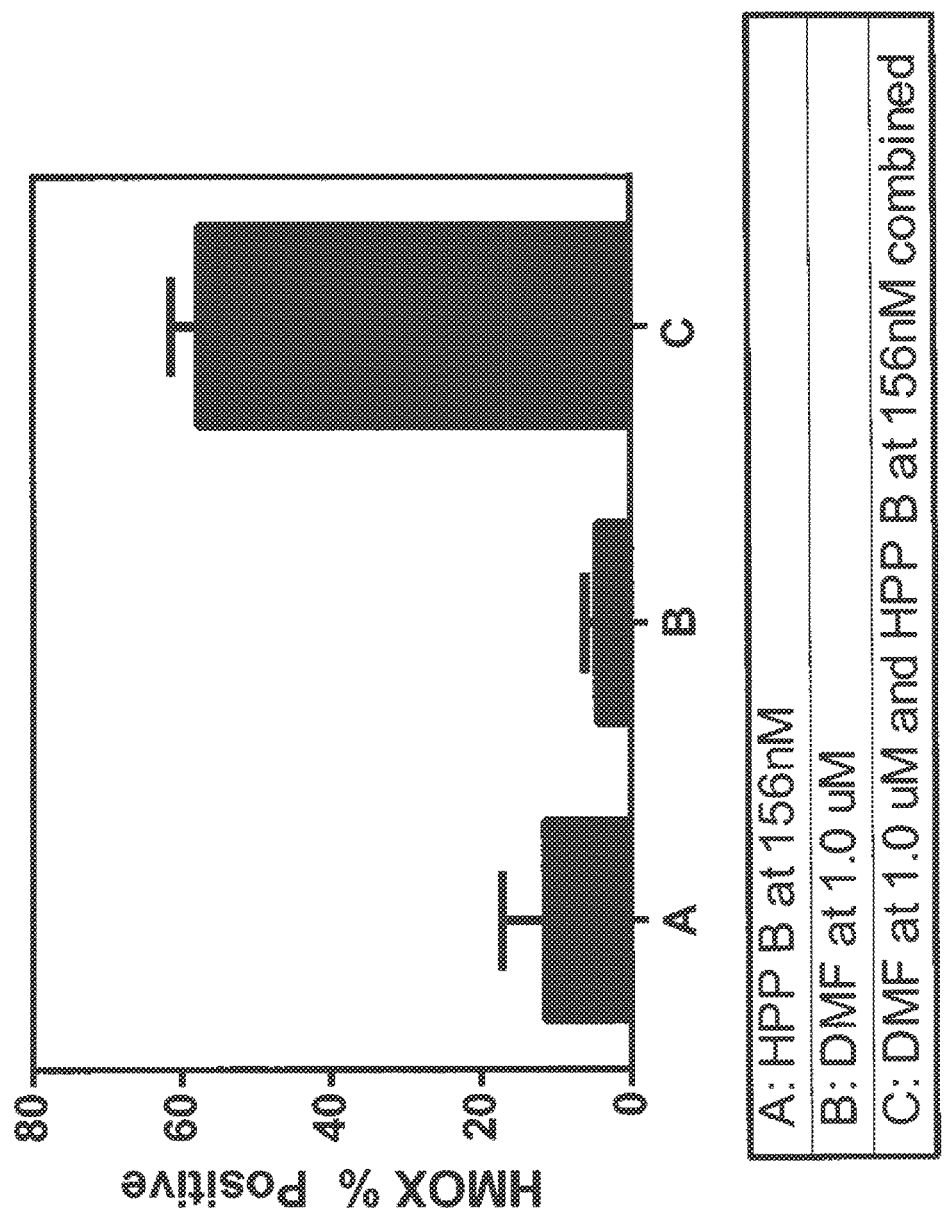
FIG. 2 shows the effect on % HMOX1 positive cells of 156 nm HPP-B (bar A); 1 uM DMF (bar B); and the combination of 156 nm HPP-B and 1 uM DMF (bar C).

FIG. 2 shows the effect on % HMOX1 positive cells of 156 nm HPP-B (bar A); 1 uM DMF (bar B); and the combination of 156 nm HPP-B and 1 uM DMF (bar C).

Figure 3:
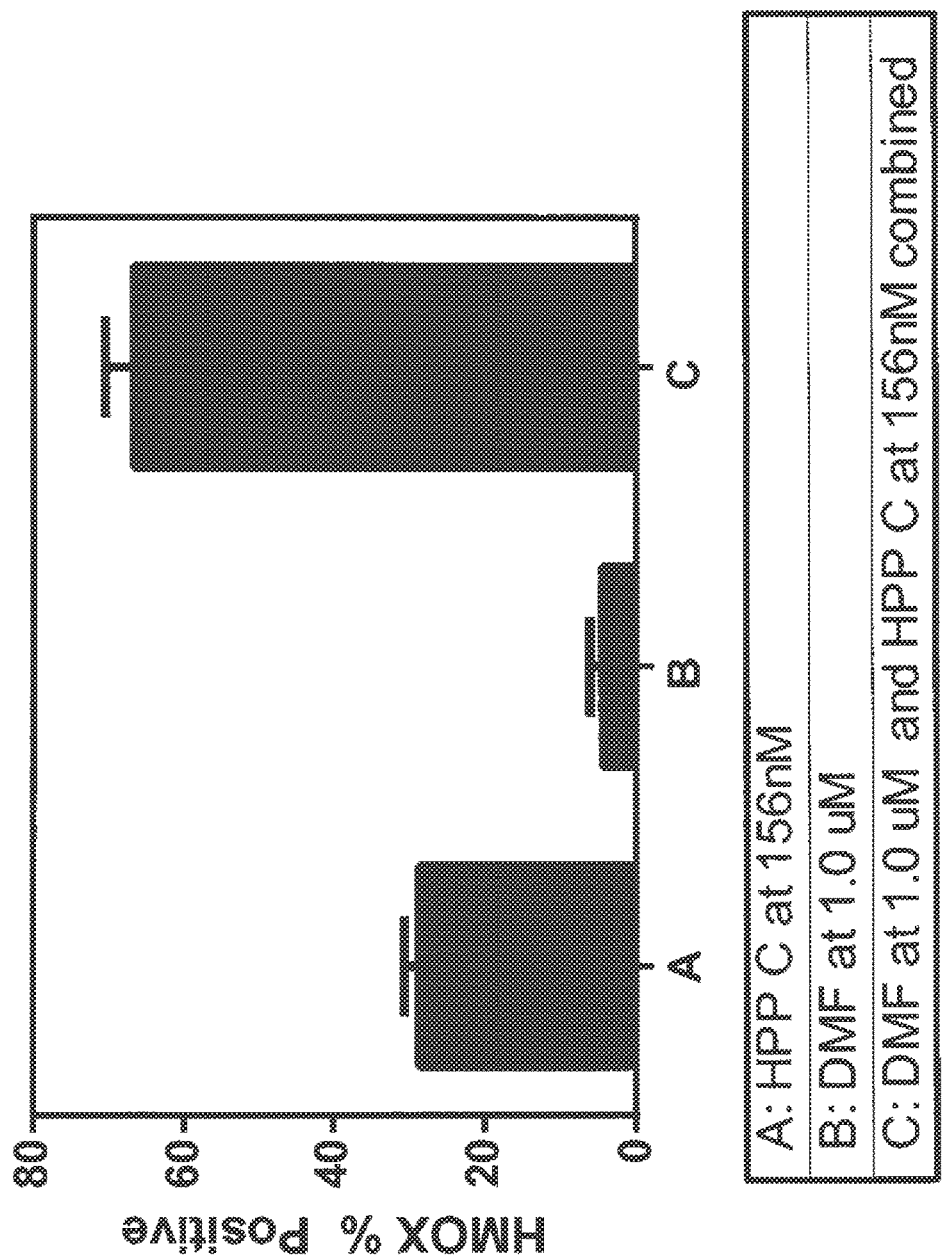
FIG. 3 shows the effect on % HMOX1 positive cells of 156 nm HPP-C (bar A); 1 uM DMF (bar B); and the combination of 156 nm HPP-C and 1 uM DMF (bar C).

FIG. 3 shows the effect on % HMOX1 positive cells of 156 nm HPP-C (bar A); 1 uM DMF (bar B); and the combination of 156 nm HPP-C and 1 uM DMF (bar C).

Figure 4:
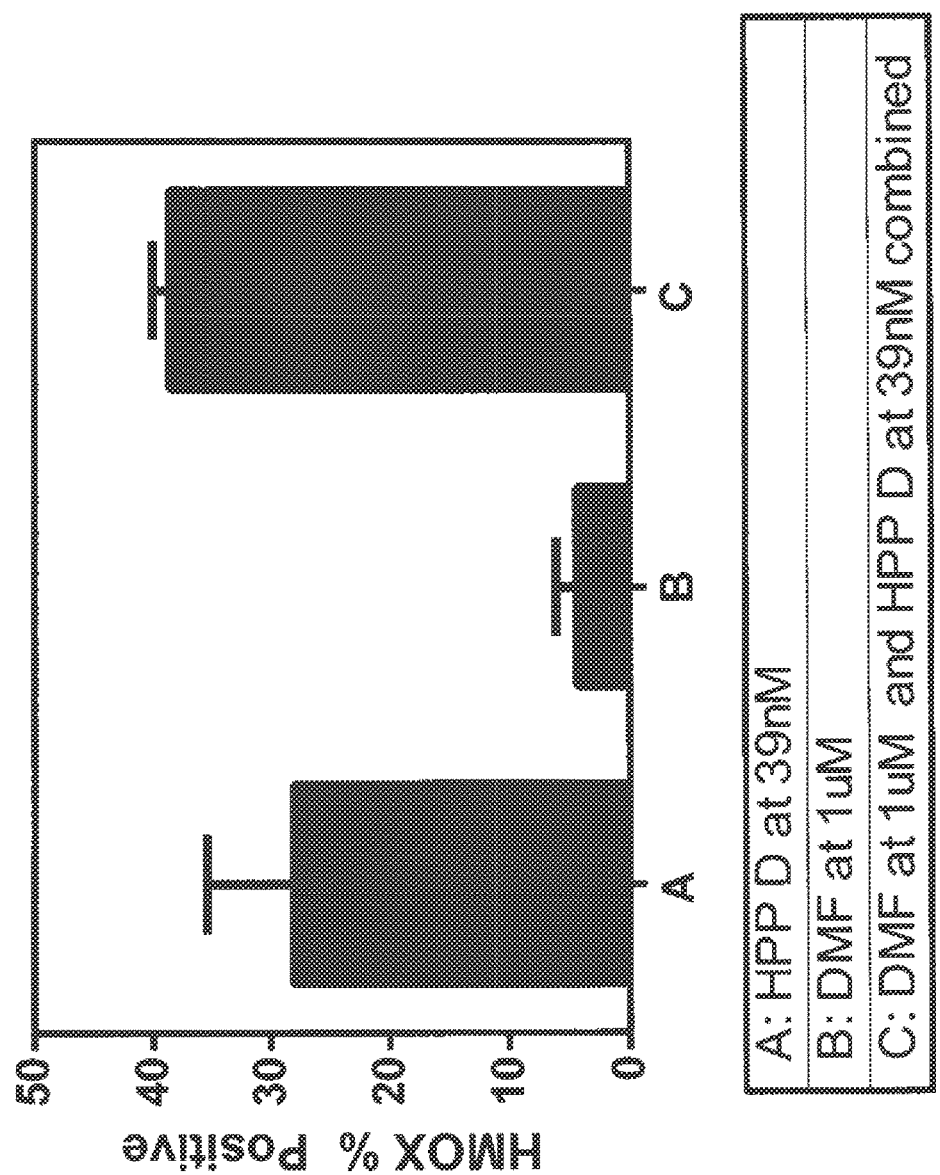
FIG. 4 shows the effect on % HMOX1 positive cells of 39 nm HPP-D (bar A); 1 uM DMF (bar B); and the combination of 39 nm HPP-D and 1 uM DMF (bar C).

FIG. 4 shows the effect on % HMOX1 positive cells of 39 nm HPP-D (bar A); 1 uM DMF (bar B); and the combination of 39 nm HPP-D and 1 uM DMF (bar C). Each of these FIGS. 2-4 indicates potential synergy between the HPP compound and DMF at these concentrations.

Table 3 provides data associated with HMOX1 induction (fold over DMSO alone) following incubation of normal human lung fibroblasts with varying concentrations of either Bach1 Inhibitor HPP-B, -C, or -D alone, DMF alone, or the two compounds in combination.

Figure 5:
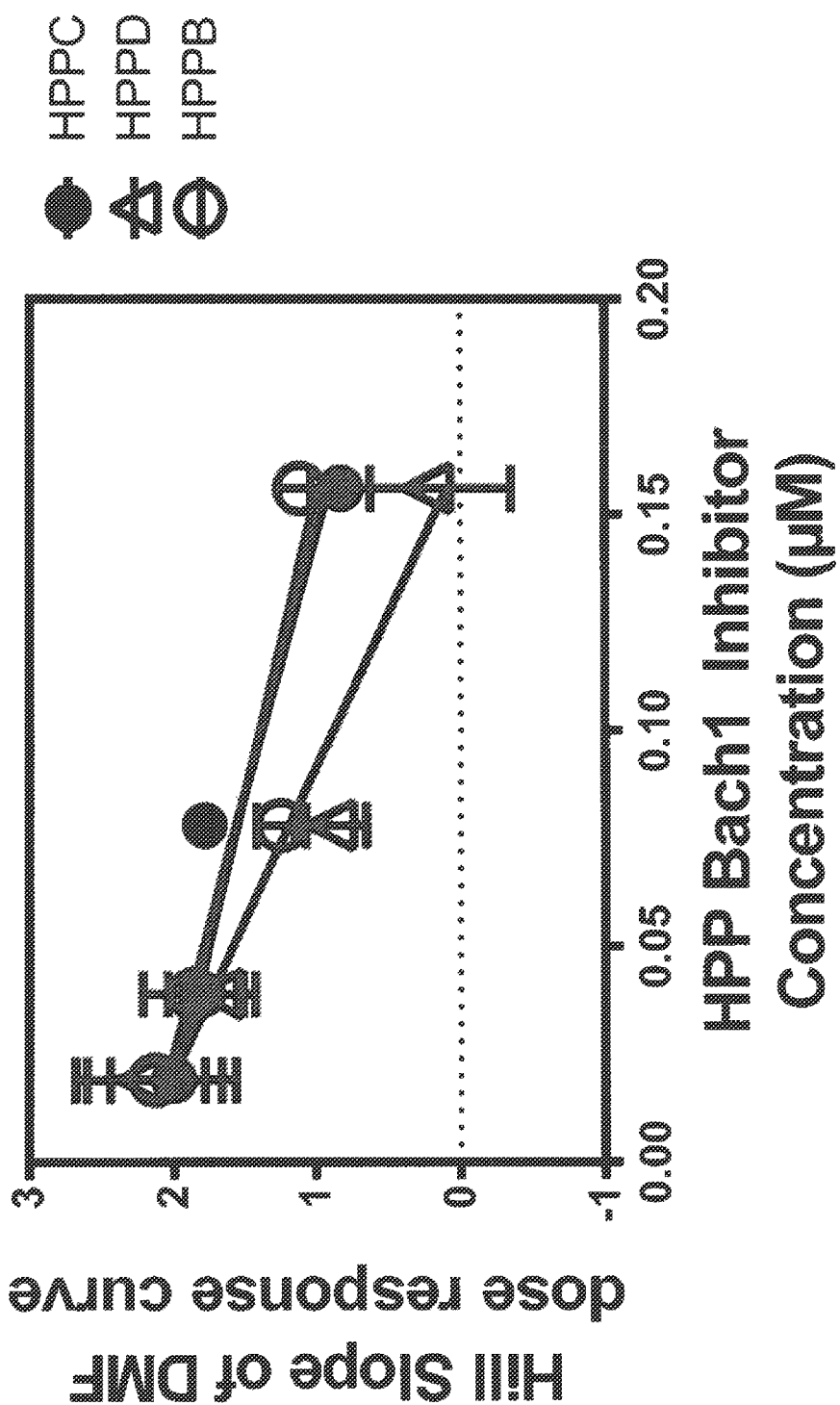
FIG. 5 shows the change in Hill slope of DMF dose response curves (% Positive HMOX) as a result of increasing amounts of either HPP-B, -C, or -D. The Hill slopes were calculated based on the data provided in Table 2.

Table 4 provides the Hill slope of the dose response curves from the data in Table 2. FIG. 5 is a graph of the data in Table 4 and shows that the Hill slope of the DMF dose response curve is reduced upon increasing amounts of either HPP-B, -C, or -D. A reduction in the Hill slope of the dose response curve may provide a greater therapeutic window for administration of the DMF.

TABLE 1

Fold Induction of HMOX

| Conc. Of HPP-A (uM) | Conc. Of Bardoxolone Methyl (uM) | | | | | | | |
|---|---|---|---|---|---|---|---|---|
| | 0 | 0.0024 | 0.0048 | 0.0097 | 0.019 | 0.039 | 0.078 | 0.156 | 0.312 |
| 0 | 0.83 | 1.31 | 1.59 | 2.53 | 5.00 | 8.48 | 12.25 | 19.01 | 16.45 |
| 0.019 | 0.97 | 3.24 | 2.88 | 7.14 | 10.00 | 15.87 | 22.27 | 22.90 | 17.20 |
| 0.039 | 1.09 | 2.32 | 3.04 | 5.31 | 8.57 | 14.73 | 18.69 | 17.24 | 17.44 |
| 0.078 | 1.92 | 4.25 | 4.72 | 8.43 | 13.21 | 17.81 | 19.51 | 17.88 | 15.33 |
| 0.156 | 3.46 | 7.32 | 8.04 | 12.05 | 15.95 | 17.59 | 18.44 | 18.30 | 15.98 |
| 0.312 | 9.82 | 11.67 | 13.59 | 16.45 | 17.74 | 19.61 | 21.13 | 19.21 | 17.40 |
| 0.625 | 15.00 | 15.70 | 17.10 | 17.18 | 16.84 | 17.24 | 18.60 | 18.68 | 12.69 |
| 1.25 | 16.17 | 16.12 | 17.26 | 16.49 | 15.93 | 15.63 | 15.15 | 16.65 | 10.53 |
| 2.5 | 17.48 | 18.81 | 19.48 | 19.42 | 17.04 | 14.71 | 14.33 | 12.49 | 10.00 |
| 5 | 17.72 | | | | | | | | |

TABLE 2

% Cells Positive HMOX

| Conc. Of Cpd. (uM) | Conc. Of DMF (uM) | | | | | | | |
|---|---|---|---|---|---|---|---|---|
| | 0 | 0.03 | 0.1 | 0.3 | 1 | 3 | 10 | 30 |
| HPP-B | | | | | | | | |
| 0 | 2.26 | 1.71 | 1.21 | 2.47 | 4.38 | 41.58 | 74.35 | 84.56 |
| 0.019 | 2.31 | 1.80 | 2.55 | 8.27 | 7.52 | 54.65 | 92.63 | 84.93 |
| 0.039 | 5.30 | 1.53 | 2.54 | 13.04 | 23.13 | 75.79 | 91.99 | 87.54 |
| 0.078 | 8.23 | 1.72 | 7.05 | 10.31 | 29.42 | 55.22 | 94.55 | 86.84 |
| 0.156 | 11.32 | 8.51 | 18.49 | 30.11 | 57.70 | 79.63 | 99.72 | 98.17 |
| HPP-C | | | | | | | | |
| 0 | 2.26 | 1.71 | 1.21 | 2.47 | 4.38 | 41.58 | 74.35 | 84.56 |
| 0.019 | 3.60 | 1.18 | 2.37 | 6.49 | 10.18 | 51.54 | 94.22 | 84.20 |
| 0.039 | 2.31 | 5.74 | 6.82 | 12.76 | 23.54 | 68.03 | 94.66 | 90.40 |
| 0.078 | 7.12 | 5.99 | 8.24 | 16.20 | 37.74 | 81.81 | 97.16 | 96.15 |
| 0.156 | 28.56 | 22.08 | 33.12 | 49.95 | 66.67 | 88.98 | 100.00 | 84.03 |
| HPP-D | | | | | | | | |
| 0 | 2.26 | 1.71 | 1.21 | 2.47 | 4.38 | 41.58 | 74.35 | 84.56 |
| 0.019 | 19.42 | 4.94 | 4.52 | 7.63 | 26.41 | 80.18 | 96.12 | 84.02 |
| 0.039 | 28.04 | 11.95 | 6.75 | 18.66 | 38.70 | 78.65 | 99.17 | 91.91 |
| 0.078 | 73.95 | 33.51 | 44.61 | 61.50 | 84.85 | 90.28 | 97.73 | 91.28 |
| 0.156 | 96.31 | 92.53 | 88.16 | 94.48 | 97.74 | 99.20 | 100.00 | 92.22 |

TABLE 3

Fold Induction of HMOX

| Conc. Of Cpd. (uM) | Conc. Of DMF (uM) | | | | | | | |
|---|---|---|---|---|---|---|---|---|
| | 0 | 0.03 | 0.1 | 0.3 | 1 | 3 | 10 | 30 |
| HPP-B | | | | | | | | |
| 0 | 1.11 | 1.04 | 1.06 | 1.14 | 1.39 | 2.76 | 4.45 | 6.19 |
| 0.019 | 1.24 | 1.17 | 1.13 | 1.43 | 1.57 | 2.98 | 4.94 | 4.23 |
| 0.039 | 1.45 | 1.07 | 1.08 | 1.59 | 1.97 | 2.84 | 4.86 | 4.82 |
| 0.078 | 1.46 | 1.12 | 1.21 | 1.43 | 2.29 | 3.12 | 5.06 | 4.52 |
| 0.156 | 1.96 | 1.46 | 1.73 | 2.06 | 2.87 | 3.63 | 5.58 | 4.99 |
| HPP-C | | | | | | | | |
| 0 | 1.11 | 1.04 | 1.06 | 1.14 | 1.39 | 2.76 | 4.45 | 6.19 |
| 0.019 | 1.29 | 1.10 | 1.15 | 1.24 | 1.68 | 2.86 | 5.75 | 4.65 |
| 0.039 | 1.37 | 1.28 | 1.35 | 1.61 | 2.10 | 3.01 | 5.13 | 4.90 |
| 0.078 | 1.59 | 1.37 | 1.48 | 1.73 | 2.53 | 4.33 | 6.46 | 6.18 |
| 0.156 | 2.66 | 1.99 | 2.54 | 3.06 | 4.08 | 4.57 | 6.55 | 5.49 |

TABLE 3-continued

Fold Induction of HMOX

| Conc. Of Cpd. (uM) | Conc. Of DMF (uM) | | | | | | |
|---|---|---|---|---|---|---|---|
| | 0 | 0.03 | 0.1 | 0.3 | 1 | 3 | 10 | 30 |

HPP-D

| 0 | 1.11 | 1.04 | 1.06 | 1.14 | 1.39 | 2.76 | 4.45 | 6.19 |
|---|---|---|---|---|---|---|---|---|
| 0.019 | 2.08 | 1.31 | 1.23 | 1.44 | 2.17 | 3.55 | 5.12 | 4.90 |
| 0.039 | 2.51 | 1.81 | 1.52 | 1.81 | 2.60 | 4.00 | 5.64 | 5.52 |
| 0.078 | 4.34 | 2.35 | 2.87 | 3.21 | 3.83 | 4.20 | 6.52 | 4.80 |
| 0.156 | 6.46 | 5.22 | 4.89 | 5.17 | 6.04 | 7.69 | 7.50 | 6.18 |

TABLE 4

Hill slope of DMF dose response curves in Table 2

| Bach1 Inhibitor Conc. (uM) | HPP-B | HPP-C | HPP-D |
|---|---|---|---|
| 0 | 1.25 | 1.26 | 1.26 |
| 0.019 | 2.14 | 2.00 | 2.23 |
| 0.039 | 1.87 | 1.80 | 1.69 |
| 0.078 | 1.25 | 1.79 | 0.90 |
| 0.156 | 1.12 | 0.83 | 0.23 |

The invention claimed is:

1. A method of treatment of a condition, comprising administering an Nrf2 activator and a Bach1 Inhibitor to a subject in need thereof,
wherein the condition is selected from the group consisting of psoriasis, scleroderma, chronic kidney disease (CKD), asthma, chronic obstructive pulmonary disorder (COPD), fibrosis, inflammatory arthritis disease, inflammatory bowel disease (IBD), multiple sclerosis, clinically isolated syndrome (CIS), amyotrophic lateral sclerosis, Alzheimer's disease, dementia, Huntington's disease, and Parkinson's disease;
wherein the Nrf2 Activator is selected from the group consisting of
a fumaric acid mono- and/or dialkyl ester, methyl 2-cyano-3,12-dioxooleana-1,9(11)dien-28-oate, ethyl 2-cyano-3,12-dioxooleana-1,9(11)dien-28-oate, 2-cyano-3,12-dioxooleana-1,9(11)dien-28-oic acid, 1[2-Cyano-3,12-dioxooleana-1,9(11)-dien-28-oyl]imidazole, and 2-cyano-N-methyl-3,12-dioxooleana-1,9(11)-dien-28 amide,
wherein the Bach1 Inhibitor is a compound of Formula (I) or a pharmaceutically acceptable salt thereof,

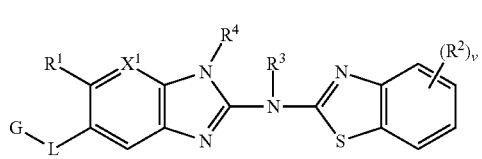

(I)

wherein
$X^1$ is =N—;
G is hydrogen, —$C_{1-8}$ alkyl, —$C_{3-10}$ cycloalkyl, —$C_{1-6}$ alkylene-$C_{3-10}$ cycloalkyl, heterocyclyl, —$C_{1-6}$ alkylene-$C_{3-10}$ heterocyclyl, phenyl, heteroaryl, or $NR^hR^k$, where the alkyl, alkylene, cycloalkyl, heterocyclyl, phenyl, and heteroaryl groups are optionally substituted one or more times with substituents independently selected from $R^c$; or G is —$CH_2Y^3$, —$CH_2CH_2Y^3$, —$CH_2CH_2CH_2Y^3$, —$CH(CH_3)CH_2Y^3$, —$CH_2CH(Y^3)CH_3$, —$CH(Y^3)CH_3$, —$CH_2C(Y^3)(CH_3)_2$, —$C(Y^3)(CH_3)_2$, or

where $Y^3$ is cyclopropyl, —$CF_3$, —$OCF_3$, —$OCH_3$, —$OCH_2CH_3$, —F, —Cl, —OH, —$O(CH_2)_2$—OH, —$O(CH_2)_2$—F, —$SCH_3$, —$S(O)_2$—$CH_3$, —$SCH_2CH_3$, —$S(O)_2CH_2CH_3$, —NH—$CH_3$, —NH—$CH_2CH_3$, —$N(CH_3)_2$, tetrahydropyran-4-yl, tetrahydrofuran-2-yl, morpholin-2-yl, morpholin-4-yl, piperidin-1-yl, 4-hydroxy-piperidin-1-yl, 3-hydroxy-piperidin-1-yl, —NH—C(O)—$CH_3$, —NH—C(O)—$CH_2CH_3$, tetrahydrofuran-2-yl-methyloxy, or —C(O)—$Y^4$, where $Y^4$ is —OH, —$OCH_3$, —$OCH_2CH_3$, —$OC(CH_3)_3$, —$NH_2$, —NH—$CH_3$, —NH—$CH_2CH_3$, —$N(CH_3)_2$, —$N(CH_2CH_3)_2$, morpholin-4-yl, 4-methyl-piperazin-1-yl, pyrrolidin-1-yl, or piperazin-1-yl;
L is —$CH_2$—C(O)N($R^6$)—, —C(O)N($R^6$)—, —C(O)—O—, —$SO_2$—, —C(O)—, heteroarylene optionally substituted one or more times with substituents independently selected from $R^x$, or heterocyclylene optionally substituted one or more times with substituents independently selected from $R^x$; or the group -L-G is -cyano;
$R^1$ is hydrogen, $R^a$, phenyl, or heteroaryl, where the phenyl and heteroaryl groups are optionally substituted one or more times with substituents independently selected from $R^x$;
$R^2$ is $R^b$;
$R^3$ is hydrogen, —$C_{1-6}$ alkyl, or —$C_{1-6}$ alkylene-$C_{3-10}$ cycloaklyl, where the alkyl, alkylene, and cycloalkyl groups are optionally substituted one or more times with substituents independently selected from $R^z$;
$R^4$ is —$C_{1-6}$ alkyl or —$C_{1-6}$ alkylene-$C_{3-10}$ cycloaklyl, where the alkyl, alkylene, and cycloalkyl groups are optionally substituted one or more times with substituents independently selected from BY;
$R^6$ is hydrogen, —$C_{1-6}$ alkyl, —$C_{1-6}$ alkylene-$C_{3-10}$ cycloaklyl, where the alkyl, alkylene, and cycloalkyl groups are optionally substituted one or more times with substituents independently selected from $R^x$;
$R^a$ is
a) -halogen,
b) —$C_{1-6}$ alkyl,
c) —$C_{3-10}$ cycloalkyl,
d) -heterocyclyl,
e) -cyano,
f) —$CF_3$,
g) —$OCF_3$,
h) —O—$R^d$,
i) —$S(O)_w$—$R^d$,
j) —$S(O)_2O$—$R^d$,
k) —$NR^dR^e$,
l) —C(O)—$R^d$,
m) —C(O)—O—$R^d$,
n) —OC(O)—$R^d$,
o) —C(O)$NR^dR^e$,
p) —C(O)-heterocyclyl,
q) —$NR^dC(O)R^e$,
r) —$OC(O)NR^dR^e$, s) —NR$^d$C(O)OR$^d$, or
t) —NR$^d$C(O)NR$^d$R$^e$,
where the alkyl, cycloalkyl, and heterocyclyl groups are optionally substituted one or more times with substituents independently selected from BY;

R$^b$ is
a) -halogen,
b) —C$_{1-6}$ alkyl,
c) —C$_{3-10}$ cycloalkyl,
d) -heterocyclyl,
e) -phenyl,
f) -heteroaryl,
g) -cyano,
h) —CF$_3$,
i) —OCF$_3$,
j) —O—R$^f$,
k) —S(O)$_w$—R$^f$,
l) —S(O)$_2$O—R$^f$,
m) —NR$^f$R$^g$,
n) —C(O)—R$^f$,
o) —C(O)—O—R$^f$,
p) —OC(O)—R$^f$,
q) —C(O)NR$^f$R$^g$,
r) —C(O)-heterocyclyl,
s) —NR$^f$C(O)R$^g$,
t) —OC(O)NR$^f$R$^g$,
u) —NR$^f$C(O)OR$^f$, or
v) —NR$^f$C(O)NR$^f$R$^g$,
where the alkyl, cycloalkyl, heterocyclyl, phenyl, and heteroaryl groups are optionally substituted one or more times with substituents independently selected from R$^z$;

R$^c$ is
a) -halogen,
b) —C$_{1-6}$ alkyl,
c) —C$_{3-10}$ cycloalkyl,
d) -heterocyclyl,
e) -cyano,
f) —CF$_3$,
g) —OCF$_3$,
h) —O—R$^h$,
i) —S(O)$_w$—R$^h$,
j) —S(O)$_2$O—R$^h$,
k) —NR$^h$R$^k$,
l) —C(O)—R$^h$,
m) —C(O)—O—R$^h$,
n) —OC(O)—R$^h$,
o) —C(O)NR$^h$R$^k$,
p) —C(O)-heterocyclyl,
q) —NR$^h$C(O)R$^k$,
r) —OC(O)NR$^h$R$^k$,
s) —NR$^h$C(O)OR$^k$,
t) —NR$^h$C(O)NR$^h$R$^k$,
u) —NR$^h$ S(O)$_w$R$^k$,
v) -phenyl,
w) -heteroaryl, or
x) —O—(C$_{1-4}$ alkylene)-O—(C$_{1-4}$ alkylene)-N(R$^h$)C(O)—OR$^k$,
where the alkylene, alkyl, cycloalkyl, heterocyclyl, phenyl, and heteroaryl groups are optionally substituted one or more times with substituents independently selected from R$^x$;

R$^d$ and R$^e$ are independently hydrogen, C$_{1-6}$ alkyl, or C$_{3-10}$ cycloalkyl, where the alkyl and cycloalkyl groups are optionally substituted one or more times with substituents independently selected from R$^y$; or, if R$^d$ and R$^e$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^y$;

R$^f$ and R$^g$ are independently hydrogen, C$_{1-6}$ alkyl, C$_{3-10}$ cycloalkyl, phenyl, or heteroaryl, where the alkyl, cycloalkyl, phenyl, and heteroaryl groups are optionally substituted one or more times with substituents independently selected from R$^z$; or, if R$^f$ and R$^g$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^z$;

R$^h$ and R$^k$ are independently hydrogen, C$_{1-6}$ alkyl, C$_{3-10}$ cycloalkyl, heterocyclyl, phenyl, or heteroaryl, where the alkyl, cycloalkyl, heterocyclyl, phenyl, and heteroaryl groups are optionally substituted one or more times with substituents independently selected from R$^x$; or, if R$^h$ and R$^k$ are both attached to the same nitrogen atom, together with that nitrogen atom may optionally form a heterocyclic ring selected from the group consisting of azetidino, pyrrolidino, pyrazolidino, imidazolidino, oxazolidino, isoxazolidino, thiazolidino, isothiazolidino, piperidino, piperazino, morpholino, thiomorpholino, and azepano, where each ring is optionally substituted one or more times with substituents independently selected from R$^x$;

R$^y$ is
a) -halogen,
b) —NH$_2$,
c) -cyano,
d) -carboxy,
e) -hydroxy,
f) -thiol,
g) —CF$_3$,
h) —OCF$_3$,
i) —C(O)—NH$_2$,
j) —S(O)$_2$—NH$_2$,
k) oxo,
l) —C$_{1-6}$ alkyl, optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
m) -heterocyclyl optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
n) —C$_{3-10}$ cycloalkyl optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$,
o) —O—C$_{1-6}$ alkyl optionally substituted one or more times with substituents selected independently from the group consisting of halogen, —OH, —O—C$_{1-6}$ alkyl, —NH$_2$, —NH—C$_{1-6}$ alkyl, and —N(C$_{1-6}$ alkyl)$_2$, p) —O—$C_{3-10}$ cycloalkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
q) —NH—$C_{1-6}$ alkyl optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
r) —N($C_{1-6}$ alkyl)$_2$ optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
s) —C(O)—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
t) —C(O)—O—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
u) —S—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
v) —S(O)$_2$—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
w) —C(O)—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
x) —C(O)—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
y) —S(O)$_2$—NH—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
z) —S(O)$_2$—N($C_{1-6}$ alkyl)$_2$, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
aa) —NH—C(O)—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$, or
bb) —NH—S(O)$_2$—$C_{1-6}$ alkyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$;

$R^x$ is
a) —$R^y$
b) -phenyl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
c) -heteroaryl, optionally substituted one or more times with substituents selected independently from the group consisting of halogen, —OH, —O—$C_{1-6}$ alkyl, —$NH_2$, —NH—$C_{1-6}$ alkyl, and —N($C_{1-6}$ alkyl)$_2$,
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

$R^z$ is
a) —$R^y$
b) -phenyl,
c) -heteroaryl;
d) —O-phenyl,
e) —O-heteroaryl,
f) —C(O)-phenyl,
g) —C(O)-heteroaryl,
h) —C(O)—O-phenyl, or
i) —C(O)—O-heteroaryl;

v is an integer from 0 to 4, and
w is an integer from 0 to 2.

2. The method of claim 1, wherein the Nrf2 activator is a selected from the group consisting of monomethyl hydrogen fumarate, dimethyl fumarate (DMF), monoethyl hydrogen fumarate, and diethyl fumarate.

3. The method of claim 1, wherein the Nrf2 activator is methyl 2-cyano-3,12-dioxooleana-1,9(11)dien-28-oate.

4. The method of claim 1, wherein the Bach1 Inhibitor is 3-Methyl-2-(6-trifluoromethoxy-benzothiazol-2-ylamino)-3H-imidazo[4,5-b]pyridine-6-carboxylic acid (2-methoxy-ethyl)-amide or a pharmaceutically acceptable salt thereof.

5. The method of claim 1, wherein the Bach1 Inhibitor is 3-Methyl-2-(6-trifluoromethoxy-benzothiazol-2-ylamino)-3H-imidazo[4,5-b]pyridine-6-carboxylic acid dimethylcarbamoylmethyl-amide or a pharmaceutically acceptable salt thereof.

6. The method of claim 1, wherein the Bach1 Inhibitor is 3-Methyl-2-(6-trifluoromethoxy-benzothiazol-2-ylamino)-3H-imidazo[4,5-b]pyridine-6-carboxylic acid (2-morpholin-4-yl-ethyl)-amide or a pharmaceutically acceptable salt thereof.

7. The method of claim 1, wherein the Bach1 Inhibitor is 3-Methyl-2-(6-trifluoromethoxy-benzothiazol-2-ylamino)-3H-imidazo[4,5-b]pyridine-6-carboxylic acid (2-hydroxy-propyl)-amide or a pharmaceutically acceptable salt thereof.

* * * * *

UNITED STATES PATENT AND TRADEMARK OFFICE
CERTIFICATE OF CORRECTION

PATENT NO. : 10,463,652 B2  
APPLICATION NO. : 16/188652  
DATED : November 5, 2019  
INVENTOR(S) : Otis Clinton Attucks Page 1 of 1

It is certified that error appears in the above-identified patent and that said Letters Patent is hereby corrected as shown below:

In the Claims

Claim 1: Column 83, Line 65: "NR$^h$R$^k$" should read -- —NR$^h$R$^k$ --.

Claim 1: Column 84, Line 44: "BY" should read -- R$^Y$ --.

Claim 1: Column 85, Line 5: "BY" should read -- R$^Y$ --.

Claim 1: Column 88, Line 33: "from 0 to 4, and" should read -- from 0 to 4; and --.

Claim 2: Column 88, Lines 36-37: "is a selected" should read -- is a compound selected --.

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*